United States Patent
Freyne et al.

(10) Patent No.: US 7,449,465 B2
(45) Date of Patent: Nov. 11, 2008

(54) TRIAZOLOPYRIMIDINE DERIVATIVES AS GLYCOGEN SYNTHASE KINASE 3 INHIBITORS

(75) Inventors: Eddy Jean Edgard Freyne, Rumst (BE); Christopher John Love, Deurne (BE); Ludwig Paul Cooymans, Beerse (BE); Nele Vandermaesen, Olmen (BE); Peter Jacobus Johannes Antonius Buijnsters, Breda (NL); Marc Willems, Vosselaar (BE); Werner Constant Johan Embrechts, Beerse (BE)

(73) Assignee: Janssen Pharmaceutica, N.V., Beerse (BE)

( * ) Notice: Subject to any disclaimer, the term of this patent is extended or adjusted under 35 U.S.C. 154(b) by 44 days.

(21) Appl. No.: 10/565,065

(22) PCT Filed: Jul. 12, 2004

(86) PCT No.: PCT/EP2004/051457

§ 371 (c)(1),
(2), (4) Date: Jan. 17, 2006

(87) PCT Pub. No.: WO2005/012304

PCT Pub. Date: Feb. 10, 2005

(65) Prior Publication Data

US 2006/0183747 A1    Aug. 17, 2006

(30) Foreign Application Priority Data

Jul. 16, 2003   (EP)   .................................. 03050314

(51) Int. Cl.
| | |
|---|---|
| *A61K 31/501* | (2006.01) |
| *A61K 31/4965* | (2006.01) |
| *A61K 31/519* | (2006.01) |
| *A01N 43/90* | (2006.01) |
| *C07D 401/00* | (2006.01) |
| *C07D 403/00* | (2006.01) |
| *C07D 405/00* | (2006.01) |
| *C07D 409/00* | (2006.01) |
| *C07D 239/00* | (2006.01) |
| *C07D 471/00* | (2006.01) |
| *C07D 487/00* | (2006.01) |
| *C07D 491/00* | (2006.01) |

(52) U.S. Cl. .................... 514/252.02; 514/255.05; 514/261.1; 544/238; 544/254

(58) Field of Classification Search ............. None
See application file for complete search history.

(56) References Cited

U.S. PATENT DOCUMENTS 6,737,085 B2 *   5/2004   Nishibe et al. ............. 424/725

FOREIGN PATENT DOCUMENTS

| JP | 59062594 A | 4/1984 |
|---|---|---|
| WO | 99/65897 A1 | 12/1999 |
| WO | 00/62778 A1 | 10/2000 |
| WO | 01/44246 A1 | 6/2001 |
| WO | 02/04450 A2 | 1/2002 |
| WO | 02/50073 A1 | 6/2002 |
| WO | 02/055082 A1 | 7/2002 |
| WO | 2004/018473 A2 | 3/2004 |

OTHER PUBLICATIONS

Dille et. al.; 1955; Journal of Organic Chemistry; vol. 20, p. 171-177.*
King, et. al.; 2001; Platinum on Carbon; Encyclopedia of Reaageants for Organic Synthesis; pp. 1-6.*
King, et. al.; 2001; Palladium on Carbon; Encyclopedia of Reaageants for Organic Synthesis; pp. 1-12.*
Mills, et. al.; 2001; Hydrochloric Acid; Encyclopedia of Reaageants for Organic Synthesis; pp. 1-13.*
Internal Medicine, 4th Edition, Editor-in-Chief Jay Stein, Chapters 71-72, pp. 699-715.*
Schiaffino et. al., J.Behav.Med., 1995, 18(6), p. 536.*
Cecil Textbook of Medicine, 21st Edition (2000), Goldman & Bennett (Editors), W.B. Saunders Company (Publisher), Chapter 198, pp. 1060-1074.*
Dille, et. al., Journal of Organic Chemistry, (1955), 20, 171-7.*

* cited by examiner

*Primary Examiner*—James O. Wilson
*Assistant Examiner*—Jeffrey H Murray
(74) *Attorney, Agent, or Firm*—Woodcock Washburn LLP

(57) ABSTRACT

This invention concerns compounds of formula

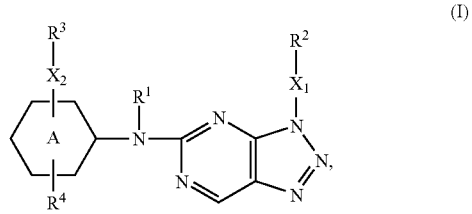

N-oxides, pharmaceutically acceptable addition salts, quaternary amines and stereochemically isomeric forms thereof, their use, pharmaceutical compositions comprising them, and processes for their preparation.

17 Claims, No Drawings

TRIAZOLOPYRIMIDINE DERIVATIVES AS GLYCOGEN SYNTHASE KINASE 3 INHIBITORS

CROSS REFERENCE TO RELATED APPLICATIONS

This application is the national stage under 35 U.S.C. 371 of Application No. PCT/EP2004/051457, filed Jul. 12, 2004, which claims priority from PCT Patent Application No. PCT/EP03/50314 filed Jul. 16, 2003, and the present application claims priority and benefit of both of the aforesaid applications which are incorporated by reference herein.

FIELD OF THE INVENTION

The present invention concerns a novel group of compounds, their use as a medicine, their use for the manufacture of a medicament for the treatment of diseases mediated through glycogen synthase kinase 3 (GSK3), in particular glycogen synthase kinase 3α and 3β; processes for their preparation and pharmaceutical compositions comprising them.

BACKGROUND OF THE INVENTION

WO 00/62778 describes cyclic protein tyrosine kinase inhibitors. In particular, it discloses thiazolyl derivatives comprising a bicyclic ring system.
WO 01/44246 describes bicyclic pyrimidine and pyridine based compounds having GSK3 inhibiting activity.
WO 99/65897 describes pyrimidine and pyridine based compounds having GSK3 inhibiting activity.
WO 02/04450 describes purine derivatives having the activity of either inhibiting the formation of amyloid beta or stimulating the formation of sbeta-amyloid precursor protein.
WO 02/50073 describes pyrazolo[3,4-c]pyridines as GSK-3 inhibitors.
WO 2004/018473 relates to di- and trisubstituted 8-aza purine derivatives as cyclin-dependent kinase inhibitors.
JP 59062594 describes 3,5-disubstituted triazolopyrimidine compounds.

SUMMARY OF THE INVENTION

The present invention relates to compounds, which are distinguishable from the prior art in structure, phanrmacological activity, potency, selectivity, solubility, permeability, metabolic stability.
The present invention concerns a compound of formula (I)

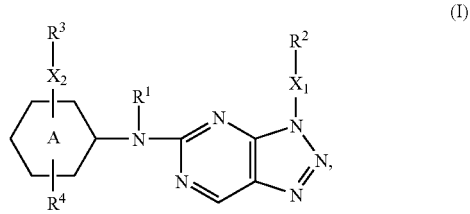

(I)

a N-oxide, a pharmaceutically acceptable addition salt, a quaternary amine and a stereochemically isomeric form thereof, wherein
ring A represents phenyl, pyridyl, pyrimidinyl, pyridazinyl or pyrazinyl;

$R^1$ represents hydrogen; aryl; formyl; $C_{1-6}$alkylcarbonyl; $C_{1-6}$alkyl; $C_{1-6}$alkyloxycarbonyl; $C_{1-6}$alkyl substituted with formyl, $C_{1-6}$alkylcarbonyl, $C_{1-6}$alkyloxycarbonyl, $C_{1-6}$alkylcarbonyloxy; or $C_{1-6}$alkyloxy$C_{1-6}$alkylcarbonyl optionally substituted with $C_{1-6}$alkyloxycarbonyl;
$X_1$ represents a direct bond; —$(CH_2)_{n3}$— or —$(CH_2)_{n4}$—$X_{1a}$—$X_{1b}$—;
with $n_3$ representing an integer with value 1, 2, 3 or 4;
with $n_4$ representing an integer with value 1 or 2;
with $X_{1a}$ representing O, C(=O) or $NR^5$; and
with $X_{1b}$ representing a direct bond or $C_{1-2}$alkyl;
$R^2$ represents $C_{3-7}$cycloalkyl; phenyl; a 4, 5, 6- or 7-membered monocyclic heterocycle containing at least one heteroatom selected from O, S or N; benzoxazolyl or a radical of formula

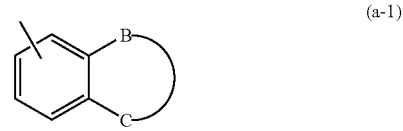

(a-1)

wherein —B—C— represents a bivalent radical of formula

—$CH_2$—$CH_2$—$CH_2$— (b-1);

—$CH_2$—$CH_2$—$CH_2$—$CH_2$— (b-2);

—$X_3$—$CH_2$—$CH_2$—$(CH_2)_n$— (b-3);

—$X_3$—$CH_2$—$(CH_2)_n$—$X_3$— (b-4);

—$X_3$—$(CH_2)_{n'}$—CH=CH— (b-5);

—CH=N—$X_3$— (b-6);

with $X_3$ representing O or $NR^5$;
n representing an integer with value 0, 1, 2 or 3;
n' representing an integer with value 0 or 1;

wherein said $R^2$ substituent, where possible, may optionally be substituted with at least one substituent selected from halo; hydroxy; $C_{1-6}$alkyl optionally substituted with at least one substituent selected from hydroxy, cyano, carboxyl, $C_{1-4}$alkyloxy, $C_{1-4}$alkyloxy$C_{1-4}$alkyloxy, $C_{1-4}$alkylcarbonyl, $C_{1-4}$alkyloxycarbonyl, $C_{1-4}$alkylcarbonyloxy, $NR^6R^7$, —C(=O)—$NR^6R^7$, —$NR^5$—C(=O)—$NR^6R^7$, —S(=O)$_{n1}$—$R^8$ or —$NR^5$—S(=O)$_{n1}$—$R^8$; $C_{2-6}$alkenyl or $C_{2-6}$alkynyl, each optionally substituted with at least one substituent selected from hydroxy, cyano, carboxyl, $C_{1-4}$alkyloxy, $C_{1-4}$alkylcarbonyl, $C_{1-4}$alkyloxycarbonyl, $C_{1-4}$alkylcarbonyloxy, $NR^6R^7$, —C(=O)—$NR^6R^7$, —$NR^5$—C(=O)—$NR^6R^7$, —S(=O)$_{n1}$—$R^8$ or —$NR^5$—S(=O)$_{n1}$—$R^8$; polyhalo-$C_{1-6}$alkyl optionally substituted with at least one substituent selected from hydroxy, cyano, carboxyl, $C_{1-4}$alkyloxy, $C_{1-4}$alkyloxy$C_{1-4}$alkyloxy, $C_{1-4}$alkylcarbonyl, $C_{1-4}$alkyloxycarbonyl, $C_{1-4}$alkylcarbonyloxy, $NR^6R^7$, —C(=O)—$NR^6R^7$, —$NR^5$—C(=O)—$NR^6R^7$, —S(=O)$^{n1}$—$R^8$ or —$NR^5$—S(=O)$_{n1}$—$R^8$; $C_{1-6}$alkyloxy optionally substituted with at least one substituent selected from hydroxy, cyano, carboxyl, $C_{1-4}$alkyloxy, $C_{1-4}$alkylcarbonyl, $C_{1-4}$alkyloxycarbonyl, $C_{1-4}$alkylcarbonyloxy, $NR^6R^7$, —C(=O)—$NR^6R^7$, —$NR^5$—C(=O)—$NR^6R^7$, —S(=O)$_{n1}$—$R^8$ or —$NR^5$—S(=O)$_{n1}$—$R^8$; polyhalo$C_{1-6}$alkyloxy optionally substituted with at least one substituent selected from hydroxy, cyano, carboxyl, $C_{1-4}$alkyloxy, $C_{1-4}$alkyloxy$C_{1-4}$alkyloxy, $C_{1-4}$alkylcarbonyl, $C_{1-4}$alkyloxycarbonyl, $C_{1-4}$alkylcarbonyloxy, $NR^6R^7$, —C(=O)—

$NR^6R^7$, $-NR^5-C(=O)-NR^6R^7$, $-S(=O)_{n1}-R^8$ or $-NR^5-S(=O)_{n1}-R^8$; $C_{1-6}$alkylthio; polyhalo$C_{1-6}$alkylthio; $C_{1-6}$alkyloxycarbonyl; $C_{1-6}$alkylcarbonyloxy; $C_{1-6}$alkylcarbonyl; polyhalo$C_{1-6}$alkylcarbonyl; cyano; carboxyl; aryloxy; arylthio; arylcarbonyl; aryl$C_{1-4}$alkyl; aryl$C_{1-4}$alkyloxy; $NR^6R^7$; $C(=O)NR^6R^7$; $-NR^5-C(=O)-NR^6R^7$; $-NR^5-C(=O)-R^5$; $-S(=O)_{n1}-R^8$; $-NR^5-S(=O)_{n1}-R^8$; $-S-CN$; $-NR^5-CN$; oxazolyl optionally substituted with $C_{1-4}$alkyl; imidazolyl optionally substituted with $C_{1-4}$alkyl; or

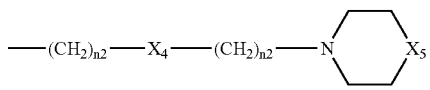

with n2 representing an integer with value 0, 1, 2, 3 or 4;
with $X_4$ representing O, $NR^5$ or a direct bond;
with $X_5$ representing O, $CH_2$, CHOH, $CH-N(R_5)_2$, $NR^5$ or $N-C(=O)-C_{1-4}$alkyl;

$X_2$ represents a direct bond; $-NR^1-$; $-NR^1-(CH_2)_{n3}-$; $-O-$; $-O-(CH_2)_{n3}-$; $-C(=O)-$; $-C(=O)-(CH_2)_{n3}-$; $-C(=O)-NR^5-(CH_2)_{n3}-$; $-C(=S)-$; $-S-$; $-S(=O)_{n1}-$; $-(CH_2)_{n3}-$; $-(CH_2)_{n4}-X_{1a}-X_{1b}-$; $-X_{1a}-X_{1b}-(CH_2)_{n4}-$; $-S(=O)_{n1}-NR^5-(CH_2)_{n3}-NR^5-$; or $-S(=O)_{n1}-NR^5-(CH_2)_{n3}-$;

$R^3$ represents a 5- or 6-membered monocyclic heterocycle containing at least one heteroatom selected from O, S or N, or a 9- or 10-membered bicyclic heterocycle containing at least one heteroatom selected from O, S or N, wherein said $R^3$ substituent, where possible, may optionally be substituted with at least one substituent selected from halo; hydroxy; $C_{1-6}$alkyl optionally substituted with at least one substituent selected from hydroxy, cyano, carboxyl, $C_{1-4}$alkyloxy, $C_{1-4}$alkyloxy$C_{1-4}$alkyloxy, $C_{1-4}$alkylcarbonyl, $C_{1-4}$alkyloxycarbonyl, $C_{1-4}$alkylcarbonyloxy, $NR^6R^7$, $-C(=O)-NR^6R^7$, $-NR^5-C(=O)-NR^6R^7$, $-S(=O)^{n1}-R^8$ or $-NR^5-S(=O)_{n1}-R^8$; $C_{2-6}$alkenyl or $C_{2-6}$alkynyl, each optionally substituted with at least one substituent selected from hydroxy, cyano, carboxyl, $C_{1-4}$alkyloxy, $C_{1-4}$alkylcarbonyl, $C_{1-4}$alkyloxycarbonyl, $C_{1-4}$alkylcarbonyloxy, $NR^6R^7$, $-C(=O)-NR^6R^7$, $-NR^5-C(=O)-NR^6R^7$, $-S(=O)_{n1}-R^8$ or $-NR^5-S(=O)_{n1}-R^8$; polyhalo$C_{1-6}$alkyl; $C_{1-6}$alkyloxy optionally substituted with at least one substituent selected from hydroxy, cyano, carboxyl, $C_{1-4}$alkyloxy, $C_{1-4}$alkylcarbonyl, $C_{1-4}$alkyloxycarbonyl, $C_{1-4}$alkylcarbonyloxy, $NR^6R^7$, $-C(=O)-NR^6R^7$, $-NR^5-C(=O)-NR^6R^7$, $-S(=O)^{n1}-R^8$ or $-NR^5-S(=O)_{n1}-R^8$; polyhalo$C_{1-6}$alkyloxy; $C_{1-6}$alkylthio; polyhalo$C_{1-6}$alkylthio; $C_{1-6}$alkyloxycarbonyl; $C_{1-6}$alkylcarbonyloxy; $C_{1-6}$alkylcarbonyl; polyhalo$C_{1-6}$alkylcarbonyl; cyano; carboxyl; $NR^6R^7$; $C(=O)NR^6R^7$; $-NR^5-C(=O)-NR^6R^7$; $-NR^5-C(=O)-R^5$; $-S(=O)_{n1}-R^8$; $-NR^5-S(=O)_{n1}-R^8$; $-S-CN$; $-NR^5-CN$; or

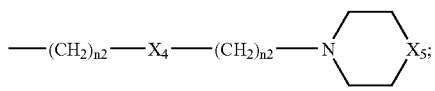

and in case $R^3$ represents a saturated or a partially saturated 5- or 6-membered monocyclic heterocycle containing at least one heteroatom selected from O, S or N, said $R^3$ may also be substituted with at least one oxo;

$R^4$ represents hydrogen; halo; hydroxy; $C_{1-4}$alkyl optionally substituted with at least one substituent selected from hydroxy, cyano, carboxyl, $C_{1-4}$alkyloxy, $C_{1-4}$alkylcarbonyl, $C_{1-4}$alkyloxycarbonyl, $C_{1-4}$alkylcarbonyloxy, $NR^9R^{10}$, $-C(=O)-NR^9R^{10}$, $-NR^5-C(=O)-NR^9R^{10}$, $-S(=O)_{n1}-R^{11}$ or $-NR^5-S(=O)_{n1}-R^{11}$; $C_{2-4}$alkenyl or $C_{2-4}$alkynyl, each optionally substituted with at least one substituent selected from hydroxy, cyano, carboxyl, $C_{1-4}$alkyloxy, $C_{1-4}$alkylcarbonyl, $C_{1-4}$alkyloxycarbonyl, $C_{1-4}$alkylcarbonyloxy, $NR^9R^{10}$, $-C(=O)-NR^9R^{10}$, $-NR^5-C(=O)-NR^9R^{10}$, $-S(=O)_{n1}-R^{11}$ or $-NR^5-S(=O)_{n1}-R^{11}$; polyhalo$C_{1-3}$alkyl; $C_{1-4}$alkyloxy optionally substituted with carboxyl; polyhalo$C_{1-3}$alkyloxy; $C_{1-4}$alkylthio; polyhalo$C_{1-3}$alkylthio; $C_{1-4}$alkyloxycarbonyl; $C_{1-4}$alkylcarbonyloxy; $C_{1-4}$alkylcarbonyl; polyhalo$C_{1-4}$alkylcarbonyl; nitro; cyano; carboxyl; $NR^9R^{10}$; $C(=O)NR^9R^{10}$; $-NR^5-C(=O)-NR^9R^{10}$; $-NR^5-C(=O)-R^5$; $-S(=O)_{n1}-R^{11}$; $-NR^5-S(=O)_{n1}-R^{11}$; $-S-CN$; or $-NR^5-CN$;

$R^5$ represents hydrogen, $C_{1-4}$alkyl or $C_{2-4}$alkenyl;

$R^6$ and $R^7$ each independently represent hydrogen; cyano; $C_{1-6}$alkylcarbonyl optionally substituted with $C_{1-4}$alkyloxy or carboxyl; $C_{1-6}$alkyloxycarbonyl; $C_{3-7}$cycloalkylcarbonyl; adamantanylcarbonyl; $C_{1-4}$alkyloxy$C_{1-4}$alkyl; $C_{1-4}$alkyl substituted with $C_{1-4}$alkyl-$NR^5-$; $C_{1-6}$alkyl optionally substituted with at least one substituent selected from halo, hydroxy, cyano, carboxyl, $C_{1-4}$alkyloxy, polyhalo$C_{1-4}$alkyl, $C_{1-4}$alkyloxy$C_{1-4}$alkyloxy, $NR^{6a}R^{7a}$, $C(=O)NR^{6a}R^{7a}$ or

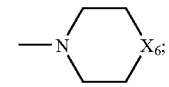

with $X_6$ representing O, $CH_2$, CHOH, $CH-N(R_5)_2$, $NR^5$ or $N-C(=O)-C_{1-4}$alkyl;

$R^{6a}$ and $R^{7a}$ each independently represent hydrogen; $C_{1-4}$alkyl or $C_{1-4}$alkylcarbonyl;

$R^8$ represents $C_{1-4}$alkyl optionally substituted with hydroxy; polyhalo$C_{1-4}$alkyl or $NR^6R^7$;

$R^9$ and $R^{10}$ each independently represent hydrogen; $C_{1-6}$alkyl; cyano; $C_{1-6}$alkylcarbonyl; $C_{1-4}$alkyloxy$C_{1-4}$alkyl; or $C_{1-4}$alkyl substituted with $C_{1-4}$alkyl-$NR^5-$;

$R^{11}$ represents $C_{1-4}$alkyl or $NR^9R^{10}$;

n1 represents an integer with value 1 or 2;

aryl represents phenyl or phenyl substituted with at least one substituent selected from halo, $C_{1-6}$alkyl, $C_{3-7}$cycloalkyl, $C_{1-6}$alkyloxy, cyano, nitro, polyhalo$C_{1-6}$alkyl or polyhalo$C_{1-6}$alkyloxy.

The present invention also relates to the use of a compound of formula (I) for the manufacture of a medicament for the prevention or the treatment of diseases mediated through GSK3.

DETAILED DESCRIPTION OF THE INVENTION

As used herein $C_{1-3}$alkyl as a group or part of a group defines straight or branched chain saturated hydrocarbon radicals having from 1 to 3 carbon atoms such as methyl, ethyl, propyl, 1-methylethyl; $C_{1-4}$alkyl as a group or part of a group defines straight or branched chain saturated hydrocarbon radicals having from 1 to 4 carbon atoms such as the groups defined for $C_{1-3}$alkyl and butyl; $C_{1-6}$alkyl as a group or part of a group defines straight or branched chain saturated hydrocarbon radicals having from 1 to 6 carbon atoms such as the groups defined for $C_{1-4}$alkyl and-pentyl, hexyl, 2-methylbutyl and the like; $C_{2-4}$alkenyl as a group or part of a group defines straight and branched chain hydrocarbon radicals having from 2 to 4 carbon atoms containing a double bond such as ethenyl, propenyl, butenyl and the like; $C_{2-6}$alkenyl as a group or part of a group defines straight and branched chain hydrocarbon radicals having from 2 to 6 carbon atoms containing a double bond such as the groups defined for $C_{2-4}$alkenyl and pentenyl, hexenyl and the like; $C_{2-4}$alkynyl as a group or part of a group defines straight and branched chain hydrocarbon radicals having from 2 to 4 carbon atoms containing a triple bond such as ethynyl, propynyl, butynyl and the like; $C_{2-6}$alkynyl as a group or part of a group defines straight and branched chain hydrocarbon radicals having from 2 to 6 carbon atoms containing a triple bond such as the group defined for $C_{2-4}$alkynyl and pentynyl, hexynyl and the like; $C_{3-7}$cycloalkyl is generic to cyclopropyl, cyclobutyl, cyclopentyl, cyclohexyl and cycloheptyl; a 4, 5, 6- or 7-membered monocyclic heterocycle containing at least one heteroatom selected from O, S or N comprises saturated, partially saturated or aromatic 4, 5, 6- or 7-membered monocyclic heterocycles containing at least one heteroatom selected from O, N or S; saturated heterocycles are heterocycles containing only single bonds; partially saturated heterocycles are heterocycles containing at least one double bond provided that the ring system is not an aromatic ring system; the term aromatic is well known to a person skilled in the art and designates cyclically conjugated systems of 4n'+2 electrons, that is with 6, 10, 14 etc. c-electrons (rule of Huckel; n' being 1, 2,3 etc.).

Particular examples of 4, 5, 6- or 7-membered saturated monocyclic heterocycles are azetidinyl, oxetanyl, tetrahydrofuranyl, pyrrolidinyl, dioxolanyl, imidazolidinyl, thiazolidinyl, tetrahydrothienyl, dihydrooxazolyl, isothiazolidinyl, isoxazolidinyl, oxadiazolidinyl, triazolidinyl, thiadiazolidinyl, pyrazolidinyl, piperidinyl, hexahydropyrimidinyl, hexahydropyridazinyl, dioxanyl, morpholinyl, dithianyl, thiomorpholinyl, piperazinyl, homopiperidinyl (azepanyl), [1,3]diazepanyl, homopiperazinyl ([1,4]diazepanyl), [1,2]diazepanyl, oxepanyl, dioxepanyl.

Particular examples of 5- or 6-membered partially saturated heterocycles are pyrrolinyl, imidazolinyl, pyrazolinyl and the like.

Particular examples of 4, 5, 6- or 7-membered aromatic monocyclic heterocycles are pyrrolyl, furyl, thienyl, imidazolyl, oxazolyl, isoxazolyl, thiazolyl, isothiazolyl, pyrazolyl, triazolyl, thiadiazolyl, oxadiazolyl, tetrazolyl, pyridyl, pyrimidinyl, pyrazinyl, pyridazinyl.

As used herein before, the term (=O) forms a carbonyl moiety when attached to a carbon atom, a sulfoxide moiety when attached to a sulfur atom and a sulfonyl moiety when two of said terms are attached to a sulfur atom.

Examples of $R^3$ representing a saturated 5- or 6-membered monocyclic heterocycle containing at least one heteroatom selected from O, S or N, wherein said $R^3$ is substituted with at least one oxo are e.g. cyclohexanone or tetrahydro-1,1-dioxide-2H-thiopyran.

The term halo is generic to fluoro, chloro, bromo and iodo. As used in the foregoing and hereinafter, polyhalo$C_{1-4}$alkyl and polyhalo$C_{1-6}$alkyl as a group or part of a group are defined as mono- or polyhalosubstituted $C_{1-4}$alkyl or $C_{1-6}$alkyl, for example, methyl substituted with one or more fluoro atoms, for example, difluoromethyl or trifluoromethyl, 1,1-difluoro-ethyl and the like. In case more than one halogen atoms are attached to an alkyl group within the definition of polyhalo$C_{1-4}$alkyl or polyhalo$C_{1-6}$alkyl, they may be the same or different.

The term heterocycle as in the definition of for instance $R^2$ or $R^3$ is meant to include all the possible isomeric forms of the heterocycles, for instance, pyrrolyl also includes 2H-pyrrolyl.

The hereinabove-mentioned heterocycles may be attached to the remainder of the molecule of formula (I) through any ring carbon or heteroatom as appropriate, if not otherwise specified. Thus, for example, when the 5- or 6-membered heterocycle is imidazolyl, it may be 1-imidazolyl, 2-imidazolyl, 4-imidazolyl and the like.

When any variable (eg. $R^6$, $R^7$ etc.) occurs more than one time in any constituent, each definition is independent.

Lines drawn into ring systems from substituents indicate that the bond may be attached to any of the suitable ring atoms of the ring system. For instance for a radical of formula (a-1), said radical may be attached to the remainder of the compound of formula (I) via a carbon atom of the phenyl moiety or via a carbon atom or heteroatom of the —B—C— moiety.

For therapeutic use, salts of the compounds of formula (I) are those wherein the counterion is pharmaceutically acceptable. However, salts of acids and bases which are non-pharmaceutically acceptable may also find use, for example, in the preparation or purification of a pharmaceutically acceptable compound. All salts, whether pharmaceutically acceptable or not are included within the ambit of the present invention.

The pharmaceutically acceptable addition salts as mentioned hereinabove are meant to comprise the therapeutically active non-toxic acid addition salt forms which the compounds of formula (I) are able to form. The latter can conveniently be obtained by treating the base form with such appropriate acids as inorganic acids, for example, hydrohalic acids, e.g. hydrochloric, hydrobromic and the like; sulfuric acid; nitric acid; phosphoric acid and the like; or organic acids, for example, acetic, propanoic, hydroxyacetic, 2-hydroxypropanoic, 2-oxopropanoic, oxalic, malonic, succinic, maleic, fumaric, malic, tartaric, 2-hydroxy-1,2,3-propanetricarboxylic, methanesulfonic, ethanesulfonic, benzenesulfonic, 4-methylbenzenesulfonic, cyclohexanesulfamic, 2-hydroxybenzoic, 4-amino-2-hydroxybenzoic and the like acids. Conversely the salt form can be converted by treatment with alkali into the free base form.

The compounds of formula (I) containing acidic protons may be converted into their therapeutically active non-toxic metal or amine addition salt forms by treatment with appropriate organic and inorganic bases. Appropriate base salt forms comprise, for example, the ammonium salts, the alkali and earth alkaline metal salts, e.g. the lithium, sodium, potassium, magnesium, calcium salts and the like, salts with organic bases, e.g. primary, secondary and tertiary aliphatic and aromatic amines such as methylamine, ethylamine, propylamine, isopropylamine, the four butylamine isomers, dimethylamine, diethylamine, diethanolamine, dipropylamine, diisopropylamine, di-n-butylamine, pyrrolidine, piperidine, morpholine, trimethylamine, triethylamine, tripropylamine, quinuclidine, pyridine, quinoline and isoquinoline, the benzathine, N-methyl-D-glucamine, 2-amino-2-(hydroxymethyl)-1,3-propanediol, hydrabamine salts, and salts with amino acids such as, for example, arginine, lysine and the like. Conversely the salt form can be converted by treatment with acid into the free acid form.

The term addition salt also comprises the hydrates and solvent addition forms which the compounds of formula (I) are able to form. Examples of such forms are e.g. hydrates, alcoholates and the like.

The term "quaternary amine" as used hereinbefore defines the quaternary ammonium salts which the compounds of formula (I) are able to form by reaction between a basic nitrogen of a compound of formula (I) and an appropriate quaternizing agent, such as, for example, an optionally substituted alkylhalide, arylhalide or arylalkylhalide, e.g. methyliodide or benzyliodide. Other reactants with good leaving groups may also be used, such as alkyl trifluoromethanesulfonates, alkyl methanesulfonates, and alkyl p-toluenesulfonates. A quaternary amine has a positively charged nitrogen. Pharmaceutically acceptable counterions include chloro, bromo, iodo, trifluoroacetate and acetate. The counterion of choice can be introduced using ion exchange resins.

The N-oxide forms of the present compounds are meant to comprise the compounds of formula (I) wherein one or several tertiary nitrogen atoms are oxidized to the so-called N-oxide.

The term "stereochemically isomeric forms" as used hereinbefore defines all the possible stereoisomeric forms which the compounds of formula (I), and their N-oxides, addition salts, quaternary amines or physiologically functional derivatives may possess. Unless otherwise mentioned or indicated, the chemical designation of compounds denotes the mixture of all possible stereochemically isomeric forms, said mixtures containing all diastereomers and enantiomers of the basic molecular structure as well as each of the individual isomeric forms of formula (I) and their N-oxides, salts, solvates or quaternary amines substantially free, i.e. associated with less than 10%, preferably less than 5%, in particular less than 2% and most preferably less than 1% of the other isomers. In particular, stereogenic centers may have the R- or S-configuration; substituents on bivalent cyclic (partially) saturated radicals may have either the cis- or trans-configuration. Compounds encompassing double bonds can have an E or Z-stereochemistry at said double bond. Stereochemically isomeric forms of the compounds of formula (I) are obviously intended to be embraced within the scope of this invention.

Some of the compounds of formula (I) may also exist in their tautomeric form (e.g. keto-enol tautomerism). Such forms although not explicitly indicated in the above formula are intended to be included within the scope of the present invention.

Whenever used hereinafter, the term "compounds of formula (I)" is meant to also include their N-oxide forms, their salts, their quaternary amines and their stereochemically isomeric forms. Of special interest are those compounds of formula (I) which are stereochemically pure.

A first embodiment of the present invention are those compounds of formula (I), wherein ring A represents phenyl, pyridyl, pyrimidinyl, pyridazinyl or pyrazinyl;

$R^1$ represents hydrogen; aryl; formyl; $C_{1-6}$alkylcarbonyl; $C_{1-6}$alkyl; $C_{1-6}$alkyloxycarbonyl; $C_{1-6}$alkyl substituted with formyl, $C_{1-6}$alkylcarbonyl, $C_{1-6}$alkyloxycarbonyl, $C_{1-6}$alkylcarbonyloxy; or $C_{1-6}$alkyloxy$C_{1-6}$alkylcarbonyl optionally substituted with $C_{1-6}$alkyloxycarbonyl;

$X_1$ represents a direct bond; —$(CH_2)_{n3}$— or —$(CH_2)_{n4}$—$X_{1a}$—$X_{1b}$—;

with $n_3$ representing an integer with value 1, 2, 3 or 4;

with $n_4$ representing an integer with value 1 or 2;

with $X_{1a}$ representing O or $NR^5$; and with $X_{1b}$ representing a direct bond or $C_{1-2}$alkyl;

$R^2$ represents $C_{3-7}$cycloalkyl; phenyl or a 4, 5, 6- or 7-membered monocyclic heterocycle containing at least one heteroatom selected from O, S or N; or a radical of formula

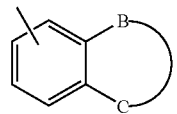

(a-1)

wherein —B—C— represents a bivalent radical of formula

—$CH_2$—$CH_2$—$CH_2$— (b-1);

—$CH_2$—$CH_2$—$CH_2$—$CH_2$— (b-2);

—$X_3$—$CH_2$—$CH_2$—$(CH_2)_n$— (b-3);

—$X_3$—$CH_2$—$(CH_2)_n$—$X_3$— (b-4);

—$X_3$—$(CH_2)_{n'}$—CH=CH— (b-5);

with $X_3$ representing O or $NR^5$;

n representing an integer with value 0, 1, 2 or 3;

n' representing an integer with value 0 or 1;

wherein said $R^2$ substituent, where possible, may optionally be substituted with at least one substituent selected from halo; hydroxy; $C_{1-6}$alkyl optionally substituted with at least one substituent selected from hydroxy, cyano, carboxyl, $C_{1-4}$alkyloxy, $C_{1-4}$alkylcarbonyl, $C_{1-4}$alkyloxycarbonyl, $C_{1-4}$alkylcarbonyloxy, $NR^6R^7$, —C(=O)—$NR^6R^7$, —$NR^5$—C(=O)—$NR^6R^7$, —S(=O)$_{n1}$—$R^8$ or —$NR^5$—S(=O)$_{n1}$—$R^8$; $C_{2-6}$alkenyl or $C_{2-6}$alkynyl, each optionally substituted with at least one substituent selected from hydroxy, cyano, carboxyl, $C_{1-4}$alkyloxy, $C_{1-4}$alkylcarbonyl, $C_{1-4}$alkyloxycarbonyl, $C_{1-4}$alkylcarbonyloxy, $NR^6R^7$, —C(=O)—$NR^6R^7$, —$NR^5$—C(=O)—$NR^6R^7$, —S(=O)$_{n1}$—$R^8$ or —$NR^5$—S(=O)$_{n1}$—$R^8$; polyhalo$C_{1-6}$alkyl; $C_{1-6}$alkyloxy optionally substituted with carboxyl; polyhalo$C_{1-6}$alkyloxy; $C_{1-6}$alkylthio; polyhalo$C_{1-6}$alkylthio; $C_{1-6}$alkyloxycarbonyl; $C_{1-6}$alkylcarbonyloxy; $C_{1-6}$alkylcarbonyl; polyhalo$C_{1-6}$alkylcarbonyl; cyano; carboxyl; $NR^6R^7$; C(=O)$NR^6R^7$; —$NR^5$—C(=O)—$NR^6R^7$; —$NR^5$—C(=O)—$R^5$; —S(=O)$_{n1}$—$R^8$; —$NR^5$—S(=O)$_{n1}$—$R^8$; —S—CN; —$NR^5$—CN; or

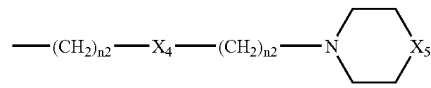

with n2 representing an integer with value 0, 1, 2, 3 or 4;

with $X_4$ representing O, $NR^5$ or a direct bond;

with $X_5$ representing O or $NR^5$;

$X_2$ represents a direct bond; —$NR^5$—; —O—; —C(=O)—; —C(=S)—; —S—; —S(=O)$_{n1}$—; —$(CH_2)_{n3}$—; or —$(CH_2)_{n4}$—$X_{1a}$—$X_{1b}$—;

$R^3$ represents a 5- or 6-membered monocyclic heterocycle containing at least one heteroatom selected from O, S or N, wherein said $R^3$ substituent, where possible, may optionally be substituted with at least one substituent selected from halo; hydroxy; $C_{1-6}$alkyl optionally substituted with at least one substituent selected from hydroxy, cyano, carboxyl, $C_{1-4}$alkyloxy, $C_{1-4}$alkylcarbonyl, $C_{1-4}$alkyloxycarbonyl, $C_{1-4}$alkylcarbonyloxy, $NR^6R^7$, —C(=O)—$NR^6R^7$, —$NR^5$—C(=O)—$NR^6R^7$, —S(=O)$_{n1}$—$R^8$ or —$NR^5$—S(=O)$_{n1}$—$R^8$; $C_{2-6}$alkenyl or $C_{2-6}$alkynyl, each optionally substituted with at least one substituent selected from hydroxy, cyano, carboxyl, $C_{1-4}$alkyloxy, $C_{1-4}$alkylcarbonyl, $C_{1-4}$alkyloxycarbonyl, $C_{1-4}$alkylcarbonyloxy, NR$^6$R$^7$, —C(=O)—NR$^6$R$^7$, —NR$^5$—C(=O)—NR$^6$R$^7$, —S(=O)$_{n1}$—R$^8$ or —NR$^5$—S(=O)$_{n1}$—R$^8$; polyhaloC$_{1-6}$alkyl; C$_{1-6}$alkyloxy optionally substituted with carboxyl; polyhaloC$_{1-6}$alkyloxy; C$_{1-6}$alkylthio; polyhaloC$_{1-6}$alkylthio; C$_{1-6}$alkyloxycarbonyl; C$_{1-6}$alkylcarbonyloxy; C$_{1-6}$alkylcarbonyl; polyhaloC$_{1-6}$alkylcarbonyl; cyano; carboxyl; NR$^6$R$^7$; C(=O)NR$^6$R$^7$; —NR$^5$—C(=O)—NR$^6$R$^7$; —NR$^5$—C(=O)—R$^5$; —S(=O)$_{n1}$—R$^8$; —NR$^5$—S(=O)$_{n1}$—R$^8$; —S—CN; —NR$^5$—CN; or

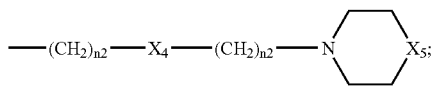

and in case R$^3$ represents a saturated 5- or 6-membered monocyclic heterocycle containing at least one heteroatom selected from O, S or N, said R$^3$ may also be substituted with at least one oxo;

R$^4$ represents hydrogen; halo; hydroxy; C$_{1-4}$alkyl optionally substituted with at least one substituent selected from hydroxy, cyano, carboxyl, C$_{1-4}$alkyloxy, C$_{1-4}$alkylcarbonyl, C$_{1-4}$alkyloxycarbonyl, C$_{1-4}$alkylcarbonyloxy, NR$^9$R$^{10}$, —C(=O)—NR$^9$R$^{10}$, —NR$^5$—C(=O)—NR$^9$R$^{10}$, —S(=O)$_{n1}$—R$^{11}$ or —NR$^5$—S(=O)$_{n1}$—R$^{11}$; C$_{2-4}$alkenyl or C$_{2-4}$alkynyl, each optionally substituted with at least one substituent selected from hydroxy, cyano, carboxyl, C$_{1-4}$alkyloxy, C$_{1-4}$alkylcarbonyl, C$_{1-4}$alkyloxycarbonyl, C$_{1-4}$alkylcarbonyloxy, NR$^9$R$^{10}$, —C(=O)—NR$^9$R$^{10}$, —NR$^5$—C(=O)—NR$^9$R$^{10}$, —S(=O)$_{n1}$—R$^{11}$ or —NR$^5$—S(=O)$_{n1}$—R$^{11}$; polyhaloC$_{1-3}$alkyl; C$_{1-4}$alkyloxy optionally substituted with carboxyl; polyhaloC$_{1-3}$alkyloxy; C$_{1-4}$alkylthio; polyhaloC$_{1-3}$alkylthio; C$_{1-4}$alkyloxycarbonyl; C$_{1-4}$alkylcarbonyloxy; C$_{1-4}$alkylcarbonyl; polyhaloC$_{1-4}$alkylcarbonyl; nitro; cyano; carboxyl; NR$^9$R$^{10}$; C(=O)NR$^9$R$^{10}$; —NR$^5$—C(=O)—NR$^9$R$^{10}$; —NR$^5$—C(=O)—R$^5$; —S(=O)$_{n1}$—R$^{11}$; —NR$^5$—S(=O)$_{n1}$—R$^{11}$; —S—CN; or —NR$^5$—CN;

R$^5$ represents hydrogen or C$_{1-4}$alkyl;

R$^6$ and R$^7$ each independently represent hydrogen; cyano; C$_{1-6}$alkylcarbonyl; C$_{1-4}$alkyloxyC$_{1-4}$alkyl; C$_{1-4}$alkyl substituted with C$_{1-4}$alkyl-NR$^5$—; C$_{1-6}$alkyl optionally substituted with hydroxy, C$_{1-4}$alkyloxy, C$_{1-4}$alkyloxyC$_{1-4}$alkyloxy, NR$^{6a}$R$^{7a}$, C(=O)NR$^{6a}$R$^{7a}$ or

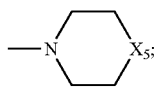

R$^{6a}$ and R$^{7a}$ each independently represent hydrogen; C$_{1-4}$alkyl or C$_{1-4}$alkylcarbonyl;

R$^8$ represents C$_{1-4}$alkyl, polyhaloC$_{1-4}$alkyl or NR$^6$R$^7$;

R$^9$ and R$^{10}$ each independently represent hydrogen; C$_{1-6}$alkyl; cyano; C$_{1-6}$alkylcarbonyl; C$_{1-4}$alkyloxyC$_{1-4}$alkyl; or C$_{1-4}$alkyl substituted with C$_{1-4}$alkyl-NR$^5$—;

R$^{11}$ represents C$_{1-4}$alkyl or NR$^9$R$^{10}$;

n1 represents an integer with value 1 or 2;

aryl represents phenyl or phenyl substituted with at least one substituent selected from halo, C$_{1-6}$alkyl, C$_{3-7}$cycloalkyl, C$_{1-6}$alkyloxy, cyano, nitro, polyhaloC$_{1-6}$alkyl or polyhaloC$_{1-6}$alkyloxy.

A second interesting embodiment of the present invention are those compounds of formula (I) wherein ring A represents phenyl;

R$^1$ represents hydrogen or C$_{1-6}$alkyl;

X$_1$ represents a direct bond or —(CH$_2$)$_{n3}$—;

R$^2$ represents C$_{3-7}$cycloalkyl; phenyl; a 6-membered monocyclic heterocycle containing at least one heteroatom selected from O, S or N; benzoxazolyl; or a radical of formula

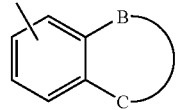

(a-1)

wherein —B—C— represents a bivalent radical of formula

—CH$_2$—CH$_2$—CH$_2$— (b-1);

—X$_3$—CH$_2$—(CH$_2$)$_n$—X$_3$— (b-4);

—CH=N—X$_3$— (b-6);

with X$_3$ representing O or NR$^5$;

n representing an integer with value 1;

wherein said R$^2$ substituent, where possible, may optionally be substituted with at least one substituent, in particular with 1 or 2 substituents selected from halo; C$_{1-6}$alkyl optionally substituted with at least one substituent selected from hydroxy, cyano, C$_{1-4}$alkyloxy, C$_{1-4}$alkyloxyC$_{1-4}$alkyloxy, NR$^6$R$^7$ or —C(=O)—NR$^6$R$^7$; polyhaloC$_{1-6}$alkyl; C$_{1-6}$alkyloxy optionally substituted with C$_{1-4}$alkyloxy; C$_{1-6}$alkylthio; C$_{1-6}$alkyloxycarbonyl; cyano; arylthio; aryloxy; arylcarbonyl; NR$^6$R$^7$; C(=O)NR$^6$R$^7$; —S(=O)$_{n1}$—R$^8$; or imidazolyl optionally substituted with C$_{1-4}$alkyl;

X$_2$ represents a direct bond; —NR$^1$—; —O—(CH$_2$)$_{n3}$—; —C(=O)—; —C(=O)—NR$^5$—(CH$_2$)$_{n3}$—; —(CH$_2$)$_{n3}$—; or —S(=O)$_{n1}$—NR$^5$—(CH$_2$)$_{n3}$—NR$^5$—;

R$^3$ represents a 5- or 6-membered monocyclic heterocycle containing at least one heteroatom selected from O, S or N, wherein said R$^3$ substituent, where possible, may optionally be substituted with at least one substituent selected from halo; hydroxy; C$_{1-6}$alkyl; NR$^6$R$^7$; and in case R$^3$ represents a saturated or a partially saturated 5- or 6-membered monocyclic heterocycle containing at least one heteroatom selected from O, S or N, said R$^3$ may also be substituted with at least one oxo; in particular R$^3$ represents imidazolyl, oxazolyl, thiazolyl, pyrrolyl, pyrazolyl, triazolyl, tetrazolyl, morpholinyl, pyridyl, piperidinyl, pyrimidinyl, pyrazinyl or piperazinyl, wherein said R$^3$ substituent, where possible, may optionally be substituted with at least one substituent selected from halo; hydroxy; C$_{1-6}$alkyl or NR$^6$R$^7$; and in case R$^3$ represents a saturated or a partially saturated 5- or 6-membered monocyclic heterocycle containing at least one heteroatom selected from O, S or N, said R may also be substituted with at least one oxo;

R$^4$ represents hydrogen; nitro or carboxyl;

R$^5$ represents hydrogen;

R$^6$ and R$^7$ each independently represent hydrogen; cyano; C$_{1-6}$alkylcarbonyl optionally substituted with C$_{1-4}$alkyloxy; C$_{1-6}$alkyloxycarbonyl; C$_{3-7}$cycloalkylcarbonyl; adamantanylcarbonyl; or C$_{1-6}$alkyl;

R$^8$ represents NR$^6$R$^7$;

n1 represents an integer with value 2;

aryl represents phenyl.

A third interesting embodiment of the present invention are those compounds of formula (I) wherein the $X_2$—$R^3$ substituent is linked to ring A in meta position compared to the $NR^1$ linker.

A fourth interesting embodiment of the present invention are those compounds of formula (I) wherein the $X_2$—$R^3$ substituent is linked to ring A in para position compared to the $NR^1$ linker.

A fifth interesting embodiment of the present invention are those compounds of formula (I) wherein the R substituent is linked to ring A in para position compared to the $NR^1$ linker.

A sixth interesting embodiment of the present invention are those compounds of formula (I) wherein the —$X_1$—$R^2$ substituent is unsubstituted or substituted with 1, 2 or 3 substituents, in particular the $R^2$ substituent is unsubstituted or substituted with 1 or 2 substituents, more in particular the —$X^1$—$R^2$ substituent is substituted with 1 substituent and preferably said substituent is placed in meta or para position compared to the linkage of the —$X_1$—$R^2$ substituent with the nitrogen of the triazole moiety of the triazolepyrimidine ring.

A seventh interesting embodiment of the present invention are those compounds of formula (I) wherein the $R^3$ substituent is unsubstituted or substituted with 1, 2 or 3 substituents, in particular the $R^3$ substituent is unsubstituted or substituted with 1 substituent.

An eighth interesting embodiment of the present invention are those compounds of formula (I) wherein the $R^3$ substituent is an optionally substituted saturated 5- or 6-membered monocyclic heterocycle containing at least one heteroatom selected from O, S or N; more preferably the $R^3$ substituent is an optionally substituted saturated 6-membered monocyclic heterocycle containing at least one heteroatom selected from O, S or N; most preferably the $R^3$ substituent is piperazinyl.

A ninth interesting embodiment of the present invention are those compounds of formula (I) wherein $R^3$ represents a 5- or 6-membered monocyclic heterocycle containing at least one heteroatom selected from O, S or N, or a 9- or 10-membered bicyclic heterocycle containing at least one heteroatom selected from O, S or N, wherein said $R^3$ substituent, where possible, may optionally be substituted with at least one substituent selected from halo; hydroxy; $C_{1-6}$alkyl optionally substituted with at least one substituent selected from hydroxy, cyano, carboxyl, $C_{1-4}$alkyloxy, $C_{1-4}$alkyloxy$C_{1-4}$alkyloxy, $C_{1-4}$alkylcarbonyl, $C_{1-4}$alkyloxycarbonyl, $C_{1-4}$alkylcarbonyloxy, $NR^6R^7$, —C(=O)—$NR^6R^7$, —$NR^5$—C(=O)—$NR^6R^7$, —S(=O)$_{n1}$—$R^8$ or —$NR^5$—S(=O)$_{n1}$—$R^8$; $C_{2-6}$alkenyl or $C_{2-6}$alkynyl, each optionally substituted with at least one substituent selected from hydroxy, cyano, carboxyl, $C_{1-4}$alkyloxy, $C_{1-4}$alkylcarbonyl, $C_{1-4}$alkyloxycarbonyl, $C_{1-4}$alkylcarbonyloxy, $NR^6R^7$, —C(=O)—$NR^6R^7$, —S(=O)$_{n1}$—$R^8$ or —$NR^5$—S(=O)$_{n1}$—$R^8$; polyhalo$C_{1-6}$alkyl; $C_{1-6}$alkyloxy optionally substituted with at least one substituent selected from hydroxy, cyano, carboxyl, $C_{1-4}$alkyloxy, $C_{1-4}$alkylcarbonyl, $C_{1-4}$alkyloxycarbonyl, $C_{1-4}$alkylcarbonyloxy, $NR^6R^7$, —C(=O)—$NR^6R^7$, —$NR^5$—C(=O)—$NR^6R^7$, —S(=O)$_{n1}$—$R^8$ or —$NR^5$—S(=O)$_{n1}$—$R^8$; polyhalo$C_{1-6}$alkyloxy; $C_{1-6}$alkylthio; polyhalo$C_{1-6}$alkylthio; $C_{1-6}$alkyloxycarbonyl; $C_{1-6}$alkylcarbonyloxy; $C_{1-6}$alkylcarbonyl; polyhalo$C_{1-6}$alkylcarbonyl; cyano; carboxyl; $NR^6R^7$; C(=O)$NR^6R^7$; —$NR^5$—C(=O)—$NR^6R^7$; —$NR^5$—C(=O)—$R^5$; —S(=O)$_{n1}$—$R^8$; —$NR^5$—S(=O)$_{n1}$—$R^8$; —S—CN; or —$NR^5$—CN; and in case $R^3$ represents a saturated or a partially saturated 5- or 6-membered monocyclic heterocycle containing at least one heteroatom selected from O, S or N, said $R^3$ may also be substituted with at least one oxo.

A tenth interesting embodiment of the present invention are those compounds of formula (I) wherein
ring A is phenyl;
$R^1$ is hydrogen;
$X_1$ is a direct bond or —(CH$_2$)$_{n3}$—;
$R^2$ is indanyl; 2,3-dihydro-1,4-benzodioxanyl; phenyl optionally being substituted with 1 or 2 substituents each independently being selected from $C_{1-6}$alkyl which may optionally be substituted with hydroxy, cyano, $C_{1-4}$alkyloxy, $C_{1-4}$alkyloxy$C_{1-4}$alkyloxy, $NR^6R^7$ or C(=O)$NR^6R^7$, wherein said $C_{1-6}$alkyl is preferably methyl; $C_{1-6}$alkyloxy, in particular methoxy; halo, in particular fluoro; polyhalo$C_{1-6}$alkyl, in particular trifluoromethyl; cyano; $NR^6R^7$; C(=O)$NR^6R^7$; or —S(=O)$_{n1}$—$R^8$;
$X_2$ is direct bond; —$NR^1$—; —O—(CH$_2$)$_{n3}$—; —C(=O)—; —C(=O)—$NR^5$—(CH$_2$)$_{n3}$—; or —(CH$_2$)$_{n3}$—;
$R^3$ is tetrazolyl; piperazinyl; imidazolyl; oxazolyl; pyrimidinyl; thiazolyl; triazolyl; pyridyl; piperidinyl, pyrazinyl; pyrazolyl; morpholinyl; said rings representing $R^3$ may optionally be substituted with one substitutent selected from $C_{1-6}$alkyl, in particular methyl; $NR^6R^7$; hydroxy; halo; and in case $R^3$ represents a saturated or a partially saturated ring system, said $R^3$ may also be substituted with at least one oxo;
$R^4$ is hydrogen;
$R^6$ and $R^7$ each independently represent hydrogen; cyano; $C_{1-6}$alkylcarbonyl optionally substituted with $C_{1-4}$alkyloxy; $C_{1-6}$alkyloxycarbonyl; $C_{3-7}$cycloalkylcarbonyl; or $C_{1-6}$alkyl;
$R^8$ represents $NR^6R^7$.

An eleventh interesting embodiment of the present invention are those compounds of formula (I) wherein
ring A is phenyl;
$R^1$ is hydrogen;
$X_1$ is a direct bond or —(CH$_2$)$_{n3}$—;
$R^2$ is phenyl optionally being substituted with 1 or 2 substituents each independently being selected from $C_{1-6}$alkyl which may optionally be substituted with hydroxy or cyano, wherein said $C_{1-6}$alkyl is preferably methyl; halo, in particular fluoro; C(=O)$NR^6R^7$;
$X_2$ is direct bond;
$R^3$ is tetrazolyl; imidazolyl; oxazolyl; pyrimidinyl; morpholinyl; said rings representing $R^3$ may optionally be substituted with one substituent selected from $C_{1-6}$alkyl, in particular methyl; or $NR^6R^7$;
$R^4$ is hydrogen;
$R^6$ and $R^7$ each independently represent hydrogen or $C_{1-6}$alkylcarbonyl.

A twelfth interesting embodiment of the present invention are those compounds of formula (I) wherein
ring A is phenyl;
$R^1$ is hydrogen;
$X_1$ is a direct bond;
$R^2$ is 2,3-dihydro-1,4-benzodioxanyl or phenyl being substituted with 1 substituent being selected from halo, in particular fluoro; or $C_{1-6}$alkyl substituted with hydroxy, cyano, $C_{1-4}$alkyloxy, $C_{1-4}$alkyloxy$C_{1-4}$alkyloxy or $NR^6R^7$;
$X_2$ is direct bond; —$NR^1$—; —O—(CH$_2$)$_{n3}$—; —C(=O)—; —C(=O)—$NR^5$—(CH$_2$)$_{n3}$—; or —(CH$_2$)$_{n3}$—;
$R^3$ is tetrazolyl; piperazinyl; imidazolyl; oxazolyl; pyrimidinyl; morpholinyl or piperidinyl; said rings representing $R^3$ may optionally be substituted with one substitutent selected from $C_{1-6}$alkyl, in particular methyl; $NR^6R^7$; or hydroxy;
$R^4$ is hydrogen;
$R^6$ and $R^7$ each independently represent hydrogen or $C_{1-6}$alkylcarbonyl.

A thirteenth interesting embodiment of the present invention are those compounds of formula (I) wherein $X_1$ represents a direct bond.

A fourteenth interesting embodiment of the present invention are those compounds of formula (I) wherein $R^2$ represents phenyl; a 4, 5, 6- or 7-membered monocyclic heterocycle containing at least one heteroatom selected from O, S or N; benzoxazolyl or a radical of formula

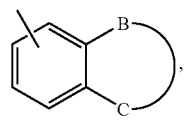

(a-1)

wherein said $R^2$ may optionally be substituted as defined hereinabove.

A fifteenth interesting embodiment of the present invention are those compounds of formula (I) wherein R represents $C_{3-7}$cycloalkyl; phenyl; a 4, 5, 6- or 7-membered monocyclic heterocycle containing at least one heteroatom selected from O, S or N; benzoxazolyl or a radical of formula (a-1) wherein said $R^2$ substituent is substituted lo with at least one substituent selected from $C_{1-6}$alkyl substituted with $NR^6R^7$; $C_{2-6}$alkenyl or $C_{2-6}$alkynyl, each substituted with $NR^6R^7$; polyhalo$C_{1-6}$alkyl substituted with $NR^6R^7$; $C_{1-6}$alkyloxy substituted with $NR^6R^7$; polyhalo$C_{1-6}$alkyloxy substituted with $NR^6R^7$; or $NR^6R^7$.

A sixteenth interesting embodiment of the present invention are those compounds of formula (I) wherein $R^3$ represents a 5- or 6-membered monocyclic heterocycle containing at least one heteroatom selected from O, S or N, or a 9- or 10-membered bicyclic heterocycle containing at least one heteroatom selected from O, S or N, wherein said $R^3$ substituent is substituted with at least one substituent selected from $C_{1-6}$alkyl substituted with $NR^6R^7$; $C_{2-6}$alkenyl or $C_{2-6}$alkynyl, each substituted with $NR^6R^7$; $C_{1-6}$alkyloxy substituted with $NR^6R^7$; or $NR^6R^7$.

A seventeenth interesting embodiment of the present invention are those compounds of formula (I) wherein $R^2$ represents $C_{3-7}$cycloalkyl; phenyl; a 4, 5, 6- or 7-membered monocyclic heterocycle containing at least one heteroatom selected from O, S or N; benzoxazolyl or a radical of formula (a-1) wherein said $R^2$ substituent is substituted with at least one substituent selected from $C_{1-6}$alkyl substituted with $NR^6R^7$; $C_{2-6}$alkenyl or $C_{2-6}$alkynyl, each substituted with $NR^6R^7$; polyhalo$C_{1-6}$alkyl substituted with $NR^6R^7$; $C_{1-6}$alkyloxy substituted with $NR^6R^7$; polyhalo$C_{1-6}$alkyloxy substituted with $NR^6R^7$; or $NR^6R^7$; and wherein $R^3$ represents a 5- or 6-membered monocyclic heterocycle containing at least one heteroatom selected from O, S or N, or a 9- or 10-membered bicyclic heterocycle containing at least one heteroatom selected from O, S or N, wherein said $R^3$ substituent is substituted with at least one substituent selected from $C_{1-6}$alkyl substituted with $NR^6R^7$; $C_{2-6}$alkenyl or $C_{2-6}$alkynyl, each substituted with $NR^6R^7$; $C_{1-6}$alkyloxy substituted with $NR^6R^7$; or $NR^6R^7$.

An eighteenth interesting embodiment of the present invention are those compounds of formula (1) wherein $R^1$ is hydrogen.

A nineteenth interesting embodiment of the present invention are those compounds of formula (I) wherein $R^2$ represents $C_{3-7}$cycloalkyl; phenyl; a 4, 5, 6- or 7-membered monocyclic heterocycle containing at least one heteroatom selected from O, S or N; benzoxazolyl or a radical of formula (a-1), wherein said $R^2$ substituent is substituted with at least one substituent selected from halo, in particular at least one fluoro atom; polyhalo$C_{1-6}$alkyl, in particular $C_{1-6}$alkyl substituted with one to three fluoro atoms, optionally substituted with at least one substituent selected from hydroxy, cyano, carboxyl, $C_{1-4}$alkyloxy, $C_{1-4}$alkyloxy$C_{1-4}$alkyloxy, $C_{1-4}$alkylcarbonyl, $C_{1-4}$alkyloxycarbonyl, $C_{1-4}$alkylcarbonyloxy, $NR^6R^7$, —C(=O)—$NR^6R^7$, —$NR^5$—C(=O)—$NR^6R^7$, —S(=O)$_{n1}$—$R^8$ or —$NR^5$—S(=O)$_{n1}$—$R^8$; polyhalo$C_{1-6}$alkyloxy, in particular $C_{1-6}$alkyloxy substituted with one to three fluoro atoms, optionally substituted with at least one substituent selected from hydroxy, cyano, carboxyl, $C_{1-4}$alkyloxy, $C_{1-4}$alkyloxy$C_{1-4}$alkyloxy, $C_{1-4}$alkylcarbonyl, $C_{1-4}$alkyloxycarbonyl, $C_{1-4}$alkylcarbonyloxy, $NR^6R^7$, —C(=O)—$NR^6R^7$, —$NR^5$—C(=O)—$NR^6R^7$, —S(=O)$_{n1}$—$R^8$ or —$NR^5$—S(=O)$_{n1}$—$R^8$.

A twentieth interesting embodiment of the present invention are those compounds of formula (I) wherein $X_1$—$R^2$ represents 3-fluorophenyl or 4-fluorophenyl.

Preferred compounds of formula (I) are compounds 17, 3, 24, 14, 65, 33, 22, 35, 9, 23, 1, 32, 52, 30, 21, 2, 29, 26, 128, 151, 73, 145, 117, 115, 138, 76, 125, 84, 152, 86, 108, 112, 80, 94, 7, 31, 20, 27, 28, 96, 97, 87, 85, as listed in Tables 1 to 5 hereinafter, their N-oxides, pharmaceutically acceptable addition salts, quaternary amines and stereochemically isomeric forms thereof.

More preferred compounds of formula (I) are compounds 7, 31, 20, 27, 28, 96, 97, 87, 85, as listed in Tables 1 to 5 hereinafter, their N-oxides, pharmaceutically acceptable addition salts, quaternary amines and stereochemically isomeric forms thereof.

Most preferred compounds of formula (I) are compounds 36, 66, 28, 96, 115, 138, 114, 84, 87, 88, 112, 78, 79, 80, 104, 106, 143 as listed in Tables 1 to 5 hereinafter, their N-oxides, pharmaceutically acceptable addition salts, quaternary amines and stereochemically isomeric forms thereof.

Compounds of formula (I) can be prepared by cyclizing an intermediate of formula (II) in the presence of a nitrite salt, such as for example $NaNO_2$, a suitable solvent, such as for example water, and a suitable acid, such as for example hydrochloric acid and/or acetic acid and the like.

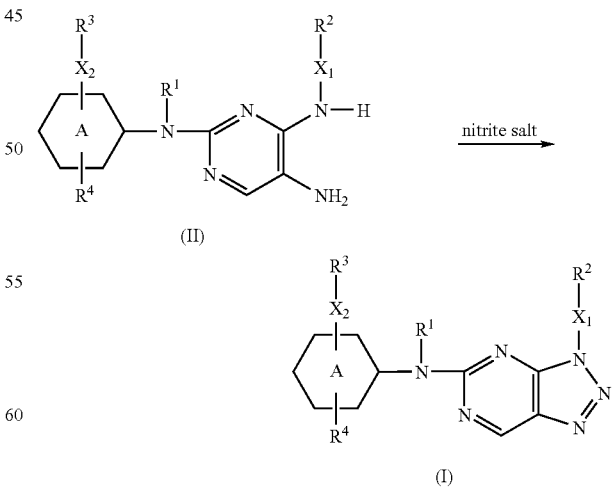

The above reaction can also be used to prepare compounds of formula (I) wherein $R^4$ represents either hydrogen or nitro, said compounds being represented by formula (I-a) and (I-b), from an intermediate of formula (II) wherein $R^4$ represents hydrogen, said intermediate being represented by formula (II-a).

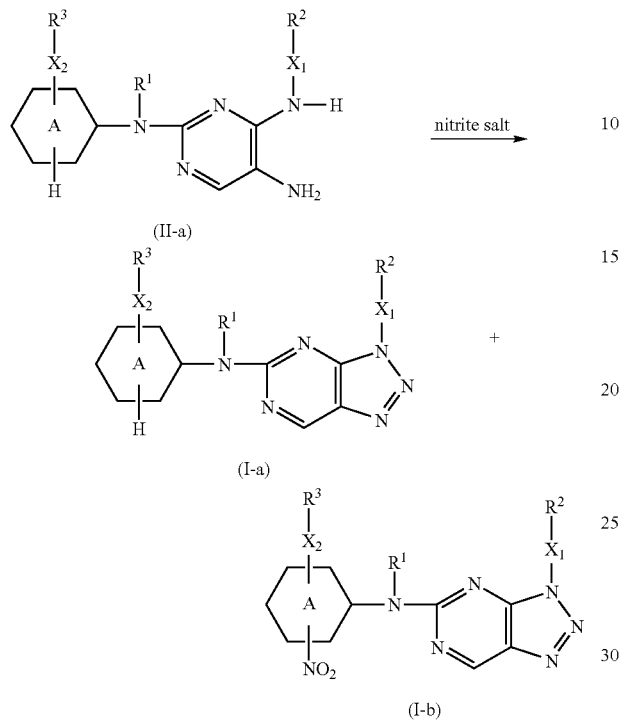

The above reaction can also be used to prepare a compound of formula (I) wherein $R^2$ represents a phenyl ring substituted with aminocarbonyl, said compound being represented by formula (I-c), from an intermediate of formula (II) wherein $R^2$ represents a phenyl ring substituted with an imidazole moiety, said intermediate being represented by formula (II-b).

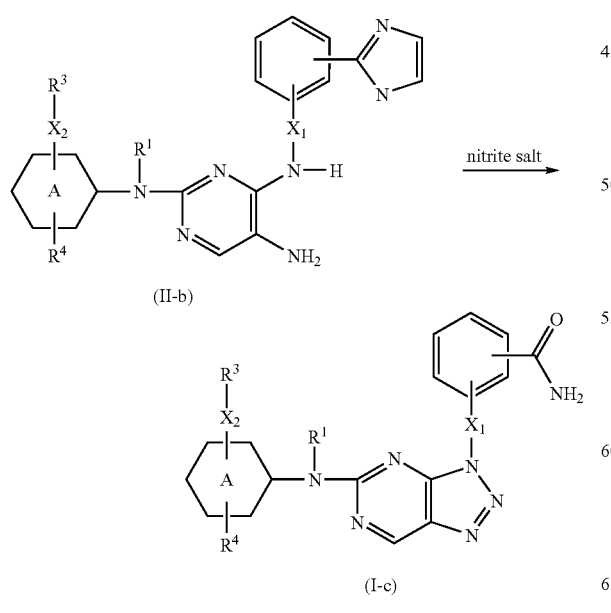

Compounds of formula (I) can also be prepared by reacting an intermediate of formula (III) with an intermediate of formula (IV) in the presence of a suitable solvent, such as for example $(CH_3)_2N-C(=O)H$, dimethylsulfoxide, $CH_3-O-CH_2-CH_2-OH$, an alcohol, e.g. 2-propanol and the like, optionally in the presence of a suitable base, such as for example N,N-diisopropylethanamine, NaH or 2,6-dimethylpyridine.

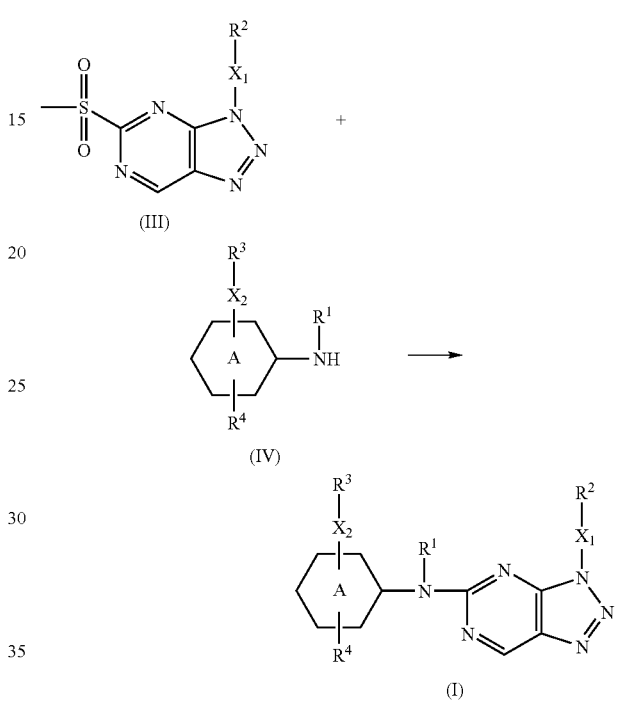

Compounds of formula (I) can also be prepared by reacting an intermediate of formula (III') with an intermediate of formula (IV) in the presence of a suitable solvent, such as for example $(CH_3)_2N-C(=O)H$, dimethylsulfoxide, $CH_3-O-CH_2-CH_2-OH$, an alcohol, e.g. 2-propanol and the like, optionally in the presence of a suitable base, such as for example N,N-diisopropylethanamine, NaH or 2,6-dimethylpyridine.

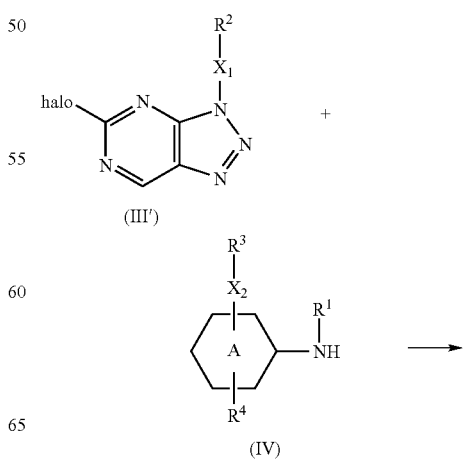

-continued

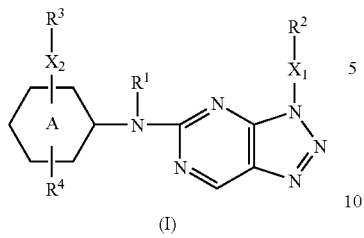
(I)

In the two above reactions, the obtained compound of formula (I) can be isolated, and, if necessary, purified according to methodologies generally known in the art such as, for example, extraction, crystallization, distillation, trituration and chromatography. In case the compound of formula (I) crystallizes out, it can be isolated by filtration. Otherwise, crystallization can be caused by the addition of an appropriate solvent, such as for example water; acetonitrile; an alcohol, such as for example methanol; and combinations of said solvents. Alternatively, the reaction mixture can also be evaporated to dryness, followed by purification of the residue by chromatography (e.g. reverse phase HPLC, flash chromatography and the like). The reaction mixture can also be purified by chromatography without previously evaporating the solvent. The compound of formula (I) can also be isolated by evaporation of the solvent followed by recrystallisation in an appropriate solvent, such as for example water; acetonitrile; an alcohol, such as for example methanol; and combinations of said solvents. The person skilled in the art will recognise which method should be used, which solvent is the most appropriate to use or it belongs to routine experimentation to find the most suitable isolation method.

Compounds of formula (I) wherein $X_2$—$R^3$ represents

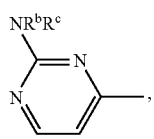

wherein $R^b$ represents hydrogen, $C_{1-4}$alkyl or cyano, and $R^c$ represents hydrogen or $C_{1-4}$alkyl, said compounds being represented by formula (I-d), can be prepared by reacting an intermediate of formula (XV) with an intermediate of formula (XVI) in the presence of a suitable solvent, such as for example $CH_3$—$CH_2$—O—$CH_2$—$CH_2$—OH, and a suitable salt, such as for example sodium methanolate.

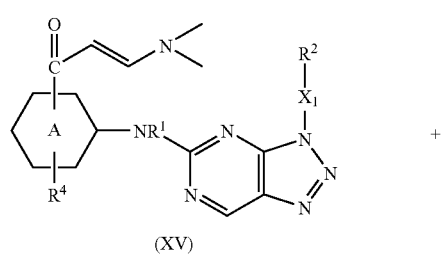
(XV)

+

-continued

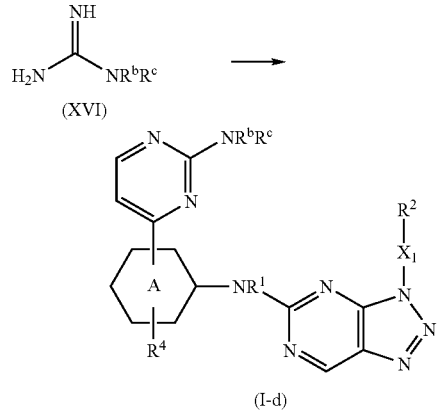

(I-d)

Compounds of formula (I) wherein $X_2$—$R^3$ represents

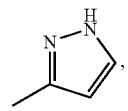

said compounds being represented by formula (I-e), can be prepared by reacting an intermediate of formula (XV) with hydrazine in the presence of a suitable solvent, such as for example $CH_3$—$CH_2$—O—$CH_2$—$CH_2$—OH.

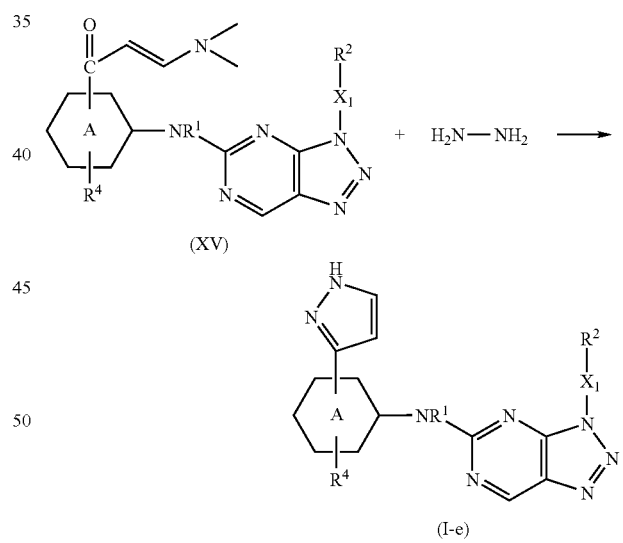

(I-e)

In this and the following preparations, the reaction products may be isolated from the reaction medium and, if necessary, further purified according to methodologies generally known in the art such as, for example, extraction, crystallization, distillation, trituration and chromatography.

The compounds of formula (I) may further be prepared by converting compounds of formula (I) into each other according to art-known group transformation reactions.

The compounds of formula (I) may be converted to the corresponding N-oxide forms following art-known procedures for converting a trivalent nitrogen into its N-oxide form.

Said N-oxidation reaction may generally be carried out by reacting the starting material of formula (I) with an appropriate organic or inorganic peroxide. Appropriate inorganic peroxides comprise, for example, hydrogen peroxide, alkali metal or earth alkaline metal peroxides, e.g. sodium peroxide, potassium peroxide; appropriate organic peroxides may comprise peroxy acids such as, for example, benzenecarboperoxoic acid or halo substituted benzenecarboperoxoic acid, e.g. 3-chlorobenzenecarboperoxoic acid, peroxoalkanoic acids, e.g. peroxoacetic acid, alkylhydroperoxides, e.g. t.butyl hydro-peroxide. Suitable solvents are, for example, water, lower alcohols, e.g. ethanol and the like, hydrocarbons, e.g. toluene, ketones, e.g. 2-butanone, halogenated hydrocarbons, e.g. dichloromethane, and mixtures of such solvents.

Compounds of formula (I) wherein $R^2$ is a ring system substituted with halo, e.g. bromo, can be converted into a compound of formula (I) wherein said $R^2$ substituent is unsubstituted, in the presence of $H_2$ and in the presence of a suitable catalyst, such as for example palladium on charcoal, a suitable catalyst poison, such as for example a thiophene solution, a suitable base, such as for example N,N-diethylethanamine, and a suitable solvent, such as for example tetrahydrofuran.

Compounds of formula (I) wherein $R^2$ is substituted with halo can also be converted into a compound of formula (I) wherein R is substituted with $C_{1-6}$alkylthio, by reaction with a reagent of formula alkaline metal$^\pm$S—$C_{1-6}$alkyl, e.g. Na$^\pm$S—$C_{1-6}$alkyl, in the presence of a suitable solvent, such as N,N-dimethylsulfoxide. The latter compounds can further be converted into a compound of formula (I) wherein $R^2$ is substituted with $C_{1-6}$alkyl-S(=O)—, by reaction with a suitable oxidizing agent, such as a peroxide, e.g. 3-chlorobenzenecarboperoxoic acid, in the presence of a suitable solvent, such as an alcohol, e.g. ethanol.

Compounds of formula (I) wherein $R^3$ and/or $R^2$ is substituted with halo can be converted into a compound of formula (I) wherein $R^3$ and/or $R^2$ is substituted with $C_{1-6}$alkyloxy, by reaction with an alcoholate salt, such as, for example, LiOC$_{1-6}$alkyl, in the presence of a suitable solvent, such as an alcohol, e.g. methanol.

Compounds of formula (I) wherein $R^3$ and/or $R^2$ is substituted with halo can also be converted into a compound of formula (I) wherein $R^3$ and/or $R^2$ is substituted with hydroxy, by reaction with a suitable carboxylate, e.g. sodium acetate, in a suitable reaction-inert solvent, such as, for example, N,N-dimethylsulfoxide, followed by treating the obtained reaction product with a suitable base, such as pyridine. Compounds of formula (I) wherein $R^3$ and/or $R^2$ is substituted with chloro, can be converted into a compound of formula (I) wherein $R^3$ and/or $R^2$ is substituted with fluoro, by reaction with a suitable fluoride salt, such as for example potassium fluoride, in the presence of a suitable-solvent, e.g. sulfolane.

Compounds of formula (I) wherein $R^3$ and/or $R^2$ is substituted with $C_{1-4}$alkyloxyC$_{1-6}$alkyl, can be converted into a compound of formula (I) wherein $R^3$ and/or $R^2$ is substituted with hydroxyC$_{1-6}$alkyl, by dealkylating the ether in the presence of a suitable dealkylating agent, such as, for example, tribromoborane, and a suitable solvent, such as methylene chloride.

Compounds of formula (I) wherein $R^3$ and/or $R^2$ is substituted with $C_{1-6}$alkyloxycarbonyl, can be converted into a compound of formula (I) wherein $R^3$ and/or $R^2$ is substituted with aminocarbonyl or mono- or di($C_{1-6}$alkyl)aminocarbonyl by reaction with a suitable agent such as ammonia, $NH_2(C_{1-6}$alkyl), AlCH$_3$[N(C$_{1-6}$alkyl)$_2$]Cl optionally in the presence of a suitable acid, such as for example hydrochloric acid, and in the presence of a suitable solvent such as an alcohol, e.g. methanol; tetrahydrofuran; N,N-diisopropylethane.

Compounds of formula (I) wherein $R^3$ and/or $R^2$ is substituted with $C_{1-6}$alkyloxycarbonyl, can also be converted into a compound of formula (I) wherein $R^3$ and/or $R^2$ is substituted with carboxyl, by reaction with a suitable base, such as for example sodium hydroxide, in the presence of a suitable solvent, such as for example dioxane or N,N-dimethylsulfoxide.

Compounds of formula (I) wherein R is unsubstituted can be converted into a compound wherein $R^2$ is substituted with halo, by reaction with a suitable halogenating agent, such as, for example Br$_2$ or 1-(chloromethyl)-4-fluoro-1,4-diazoniabicyclo[2,2,2]octane bis[tetrafluoroborate], in the presence of a suitable solvent, such as tetrahydrofuran, water, acetonitrile, chloroform and optionally in the presence of a suitable base such as N,N-diethylethanamine.

Compounds of formula (I) wherein $R^3$ and/or $R^2$ is substituted with $C_{1-6}$alkyloxycarbonyl, can be converted into a compound of formula (I) wherein $R^3$ and/or $R^2$ is substituted with hydroxymethyl by reaction with a suitable reducing agent, such as for example LiAlH$_4$.

Compounds of formula (I) wherein $R^3$ and/or $R^2$ is substituted with $NH_2$ can be converted into a compound of formula (I) wherein $R^3$ and/or $R^2$ is substituted with NH—S(=O)$^2$—NR$^6$R$^7$ by reaction with W$_1$—S(=O)$_2$—NR$^6$R$^7$ wherein W$_1$ represents a suitable leaving group such as for example a halo atom, e.g. chloro, in the presence of a suitable solvent, such as for example N,N-dimethylacetamide and a suitable base, such as for example N,N-diethylethanamine.

Compounds of formula (I) wherein $R^3$ and/or $R^2$ is substituted with NH—C(=O)—$C_{1-6}$alkyl, NH—C(=O)—O—$C_{1-6}$alkyl, $C_{1-6}$alkyl substituted with NH—C(=O)—$C_{1-6}$alkyl or with NH—C(=O)—O—$C_{1-6}$alkyl, can be converted into a compound of formula (I) wherein $R^3$ and/or $R^2$ is substituted with $NH_2$ or $C_{1-6}$alkyl substituted with $NH_2$, by reaction with a suitable acid, such as for example HCl, in the presence of a suitable solvent, such as for example dioxane or an alcohol, e.g. ethanol, methoxyethanol, 2-propanol.

Compounds of formula (I) wherein $R^3$ and/or $R^2$ is substituted with NH—S(=O)$_{n1}$—R$^8$, can be converted into a compound of formula (I) wherein $R^3$ and/or $R^2$ is substituted with N(C$_{2-4}$alkenyl)—S(=O)$_{n1}$—R$^8$, by reaction with C$_{2-4}$alkenyl-W$_1$, wherein W$_1$ represents a suitable leaving group, such as for example halo, e.g. bromo and the like, in the presence of NaH and a suitable solvent, such as for example N,N-dimethylformamide.

Compounds of formula (I) wherein $R^3$ and/or $R^2$ is substituted with $NH_2$ or $C_{1-6}$alkyl substituted with $NH_2$, can be converted into a compound of formula (I) wherein $R^3$ and/or $R^2$ is substituted with N(CH$_3$)$_2$ or $C_{1-6}$alkyl substituted with N(CH$_3$)$_2$, by reductive alkylation with [—O—CH$_2$—]$_n$ in the presence of $H_2$, a suitable catalyst, such as for example palladium on charcoal, a suitable catalyst poison, such as for example a thiophene solution, and a suitable solvent, such as for example an alcohol, e.g. methanol.

Compounds of formula (I) wherein $R^1$ is hydrogen, can be converted into a compound of formula (I) wherein $R^1$ is ethyl by reaction with N,N-diethylamine in the presence of a suitable solvent, such as for example N,N-dimethylformamide.

Compounds of formula (I) wherein $R^2$ and/or $R^3$ is substituted with C(=O)—$C_{1-6}$alkyl, can be converted into a compound of formula (I) wherein $R^2$ and/or $R^3$ is substituted with C(=O)—N(CH$_3$)$_2$, by reaction with N,N-dimethylformamide.

Some of the compounds of formula (I) and some of the intermediates in the present invention may consist of a mixture of stereochemically isomeric forms. Pure stereochemically isomeric forms of said compounds and said intermediates can be obtained by the application of art-known procedures. For example, diastereoisomers can be separated by physical methods such as selective crystallization or chromatographic techniques, e.g. counter current distribution, liquid chromatography and the like methods. Enantiomers can be obtained from racemic mixtures by first converting said racemic mixtures with suitable resolving agents such as, for example, chiral acids, to mixtures of diastereomeric salts or compounds; then physically separating said mixtures of diastereomeric salts or compounds by, for example, selective crystallization or chromatographic techniques, e.g. liquid chromatography and the like methods; and finally converting said separated diastereomeric salts or compounds into the corresponding enantiomers. Pure stereochemically isomeric forms may also be obtained from the pure stereochemically isomeric forms of the appropriate intermediates and starting materials, provided that the intervening reactions occur stereospecifically.

An alternative manner of separating the enantiomeric forms of the compounds of formula (I) and intermediates involves liquid chromatography, in particular liquid chromatography using a chiral stationary phase.

Some of the intermediates and starting materials are known compounds and may be commercially available or may be prepared according to art-known procedures.

Intermediates of formula (II) can be prepared by reducing an intermediate of formula (V) with a suitable reducing agent, such as for example $H_2$, in the presence of a suitable catalyst, such as for example platina on charcoal or palladium on charcoal, optionally in the presence of a suitable catalyst poison, such as for example a thiophene solution, optionally in the presence of $NH_2$—$NH_2$, in the presence of a suitable solvent, such as for example N,N-dimethylacetamide, tetrahydrofuran, N,N-dimethylformamide or a suitable alcohol, such as for example methanol, ethanol and the like, and optionally in the presence of a suitable base, such as for example N,N-diethylethanamine.

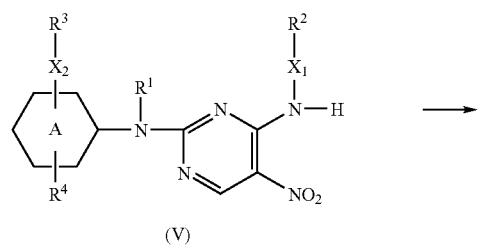

(V)

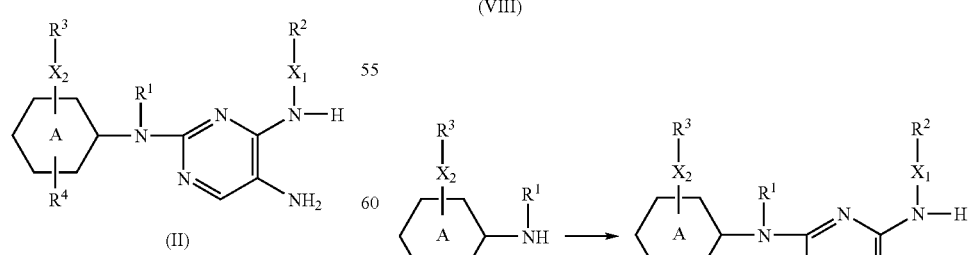

(II)

Intermediates of formula (V) can be prepared by reacting an intermediate of formula (VI) wherein $W_1$ represents a suitable leaving group, such as for example halogen, e.g. chloro and the like, with an intermediate of formula (VII) in the presence of a suitable solvent, such as for example N,N-dimethylacetamide or an alcohol, e.g. ethanol and the like, and optionally in the presence of a suitable base, such as for example N,N-diisopropylethanamine.

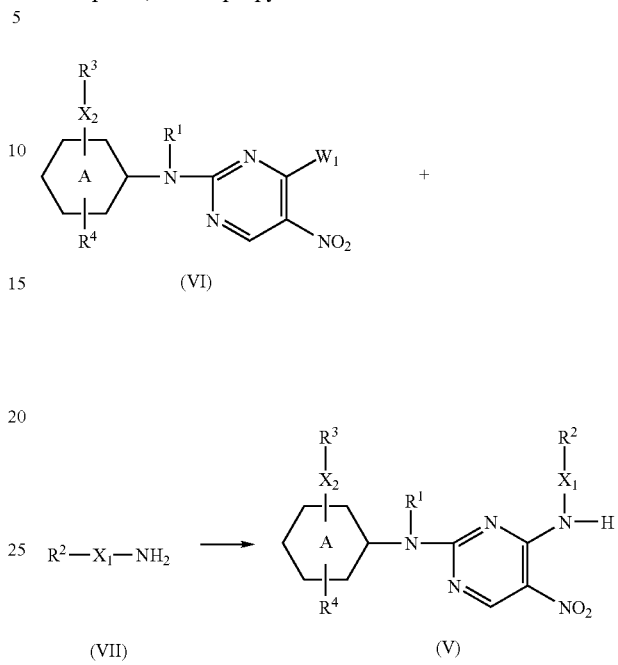

Intermediates of formula (V) can also be prepared by reacting an intermediate of formula (VIII) wherein $W_2$ represents a suitable leaving group, such as for example halogen, e.g. chloro and the like, with an intermediate of formula (IV) in the presence of a suitable base, such as for example N,N-diisopropylethanamine or N,N-diethylethanamine, and optionally in the presence of a suitable solvent, such as for example N,N-dimethylacetamide, N,N-dimethylformamide, 1,4-dioxane.

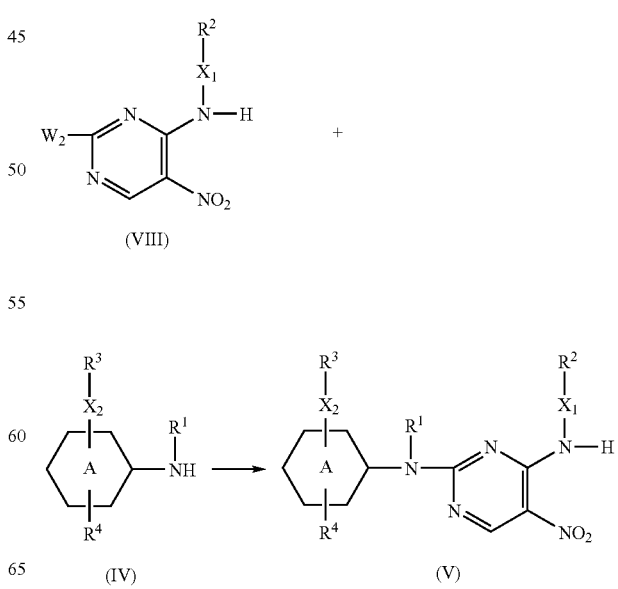

Intermediates of formula (V) wherein R²—X₁—NH— and the moiety represent the same substituent being represented by Rᵃ—NH—, said intermediates being represented by formula (V-a), can be prepared by reacting an intermediate of formula (IX) wherein W₂ is defined as hereinabove, with Rᵃ—NH₂ in the presence of a suitable base, such as for example N,N-diisopropylethanamine, and a suitable solvent, such as for example N,N-dimethylacetamide, N,N-dimethylformamide or CH₂Cl₂.

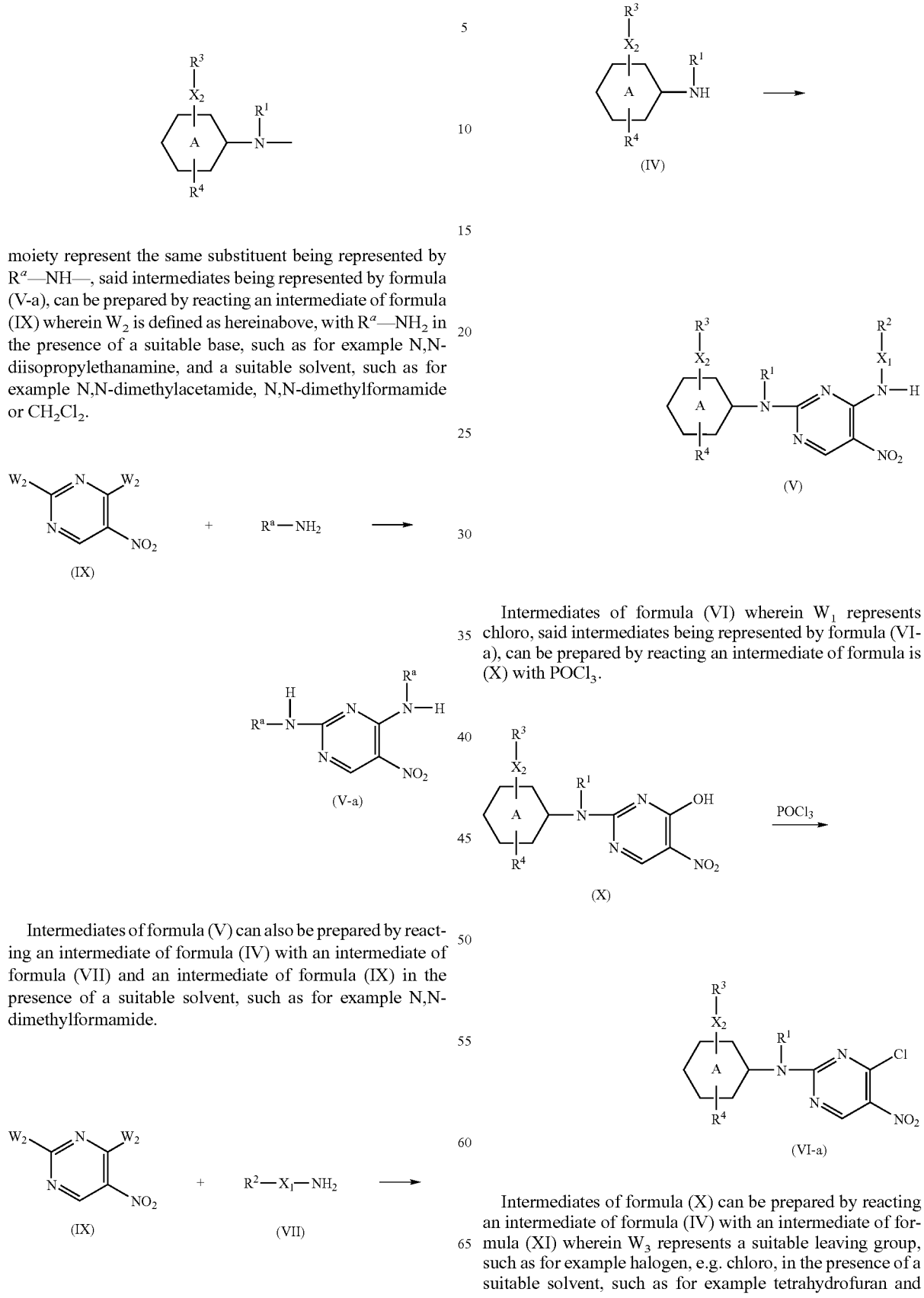

Intermediates of formula (V) can also be prepared by reacting an intermediate of formula (IV) with an intermediate of formula (VII) and an intermediate of formula (IX) in the presence of a suitable solvent, such as for example N,N-dimethylformamide.

Intermediates of formula (VI) wherein W₁ represents chloro, said intermediates being represented by formula (VI-a), can be prepared by reacting an intermediate of formula is (X) with POCl₃.

Intermediates of formula (X) can be prepared by reacting an intermediate of formula (IV) with an intermediate of formula (XI) wherein W₃ represents a suitable leaving group, such as for example halogen, e.g. chloro, in the presence of a suitable solvent, such as for example tetrahydrofuran and water, or $CH_3$—O—$(CH_2)_2$—OH, and optionally in the presence of a suitable base, such as for example N,N-diisopropylethanamine.

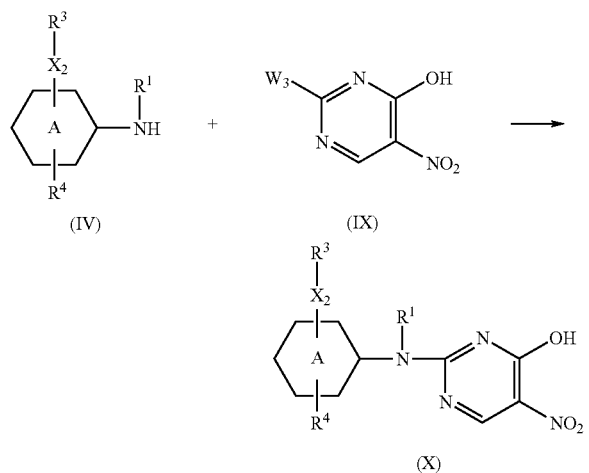

Intermediates of formula (IV) wherein $R^1$ represents hydrogen, said intermediates being represented by formula (IV-a), can be prepared by reacting an intermediate of formula (IV-b) with a suitable reducing agent, such as for example $H_2$, in the presence of a suitable catalyst, such as for example platina on charcoal or palladium on charcoal, optionally a suitable catalyst poison, such as for example a thiophene solution, a lo suitable solvent, such as for example N,N-dimethylacetamide, tetrahydrofuran, N,N-dimethylformamide or a suitable alcohol, such as for example methanol, and optionally in the presence of a suitable base, such as for example N,N-diethylethanamine.

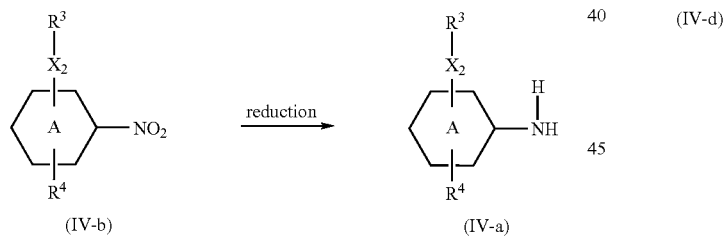

Intermediates of formula (IV-b) wherein $X_2$ is a direct bond and $R^3$ is

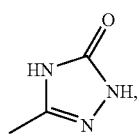

said intermediates being represented by formula (IV-b-1), can be prepared by reacting an intermediate of formula (IV-c) with $CH_3O$—C(=O)—NH—$NH_2$, in the presence of a suitable solvent, such as an alcohol, e.g. ethanol and the like, and a suitable alcoholate, such as for example sodium ethanolate and the like.

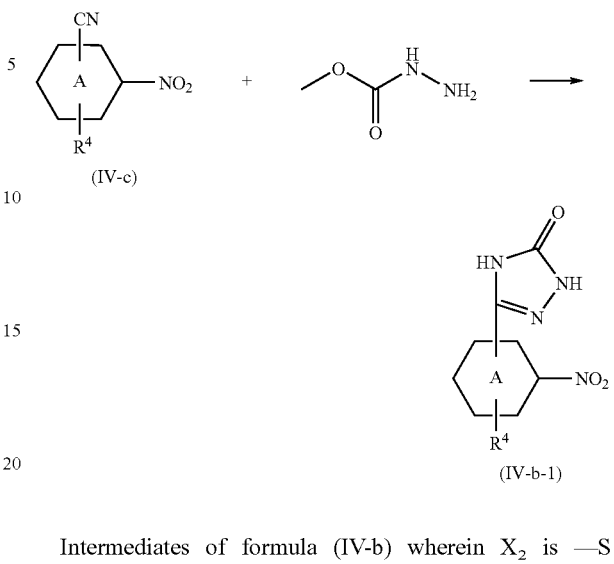

Intermediates of formula (IV-b) wherein $X_2$ is —S$(=O)_{n1}$—$NR^5$—$(CH_2)_{n3}$—, said intermediates being represented by formula (IV-b-2), can be prepared by reacting an intermediate of formula (IV-d) wherein $W_3$ is as defined above, with an intermediate of s formula (XIX) in the presence of a suitable base, such as for example $NaHCO_3$, and a suitable solvent, such as for example water and an alcohol, e.g. 2-propanol and the like.

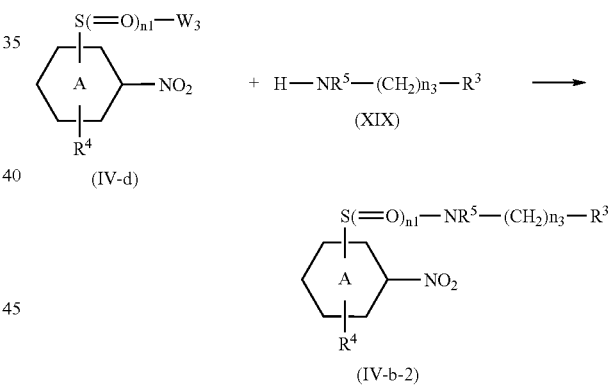

Intermediates of formula (IV) wherein $X_2$ represents $NR^1$, said intermediates being represented by formula (IV-e), can be prepared by reacting an intermediate of formula (XX) with an intermediate of formula (XXI) wherein $W_4$ represents a suitable leaving group, such as for example halo, e.g. chloro, in the presence of CaO and a suitable solvent, such as for example tetrahydrofuran.

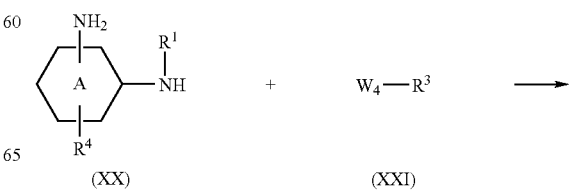

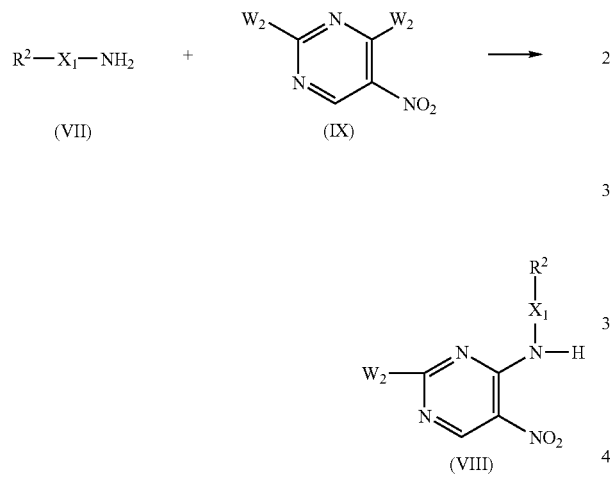

(IV-e)

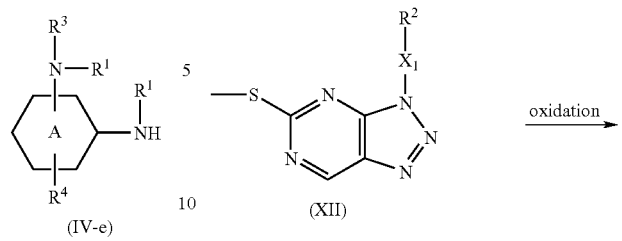

(XII)

Intermediates of formula (VIII) can be prepared by reacting an intermediate of formula (VII) with an intermediate of formula (IX) in the presence of a suitable solvent, such as for example N,N-dimethylacetamide, N,N-dimethylformamide, $CH_2Cl_2$ or 1,4-dioxane, and optionally in the presence of a suitable base, such as for example N,N-diisopropylethanamine.

(III)

Intermediates of formula (III) wherein $R^2$ is substituted with $C_{1-6}$alkyl substituted with $NR^6H$, said intermediates being represented by formula (III-a), can be prepared by reacting an intermediate of formula (XII) wherein $R^2$ is substituted with $C_{1-6}$alkyl substituted with $NH_2$, said intermediate being represented by formula (XII-a), with an intermediate of formula (XXII) wherein $W_5$ represents a suitable leaving group, such as for example halo, e.g. chloro, in the presence of a suitable oxidizing agent such as for example meta-chloroperbenzoic acid, a suitable solvent, such as for example $CH_2Cl_2$ and an alcohol, e.g. methanol and the like, optionally in the presence of morpholinomethyl polystyrene HL resin and (polystyrylmethyl)trimethylammonium bicarbonate resin.

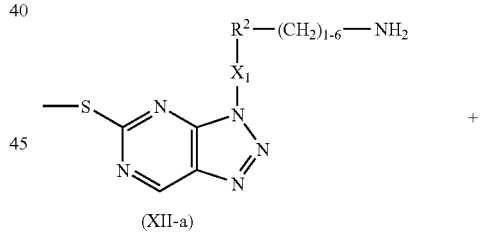

(XII-a)

Intermediates of formula (VII) can be prepared by reducing an intermediate of formula (VII-a) in the presence of Fe and an ammonium chloride solution.

Intermediates of formula (III) can be prepared by reacting an intermediate of formula (XII) with a suitable oxidizing agent, such as for example $KMnO_4$, in the presence of a suitable solvent, such as for example water, and a suitable acid, such as for example acetic acid. An alternative suitable oxidizing agent is meta-chloroperbenzoic acid, in a suitable solvent, such as for example $CH_2Cl_2$ and an alcohol, e.g. methanol and the like, optionally in the presence of morpholinomethyl polystyrene HL resin and (polystyrylmethyl)trimethylammonium bicarbonate resin.

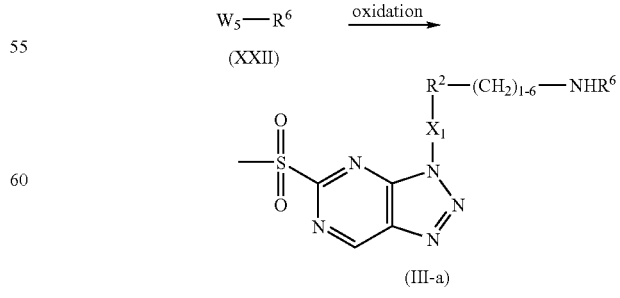

(III-a)

Intermediates of formula (XII) can be prepared by reacting an intermediate of formula (XIII) with a nitrite salt, such as for example NaNO$_2$, a suitable solvent, such as for example water, and a suitable acid, such as for example hydrochloric acid 6N or 1N and/or acetic acid and the like.

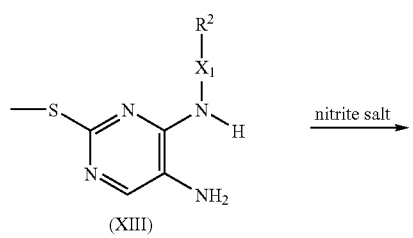

Intermediates of formula (XII-a) can be prepared by reacting an intermediate of formula (XII-b) with a suitable acid, such as for example HCl and the like, in the presence of a suitable solvent, such as for example water.

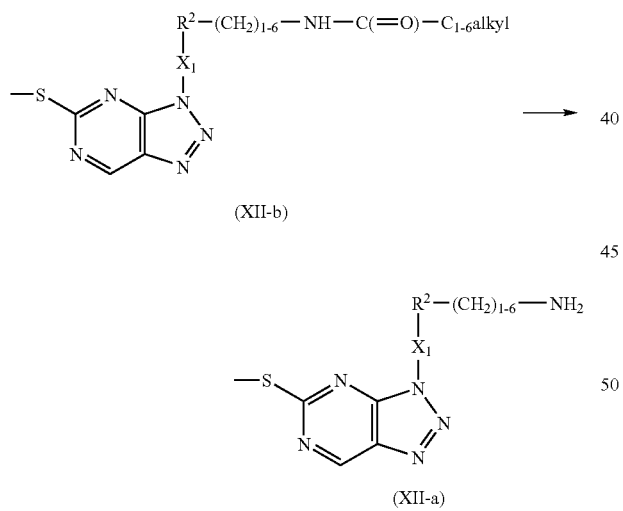

Intermediates of formula (XIII) can be prepared by reacting an intermediate of formula (XIV) with a suitable reducing agent, such as for example H$_2$, in the presence of a suitable catalyst, such as for example platina on charcoal or palladium on charcoal, optionally a suitable catalyst poison, such as for example a thiophene solution, a suitable solvent, such as for example N,N-dimethylacetamide, tetrahydrofuran, N,N-dimethylformamide or a suitable alcohol, such as for example methanol, and optionally in the presence of a suitable base, such as for example N,N-diethylethanamine.

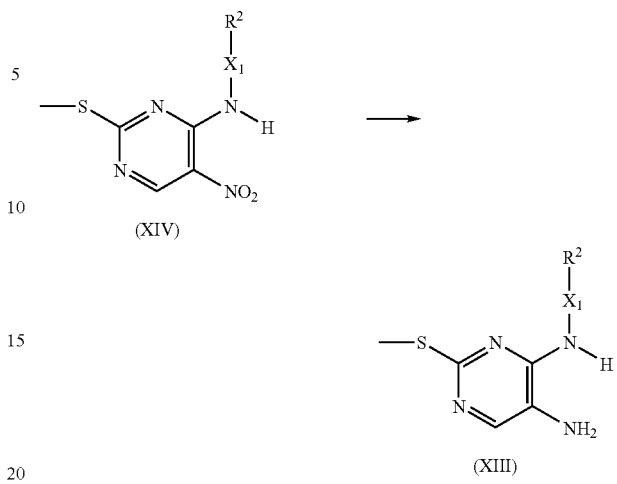

Intermediates of formula (XIVI can be prepared by reacting an intermediate of formula (VIII), in the presence of NaS—CH$_3$ in water.

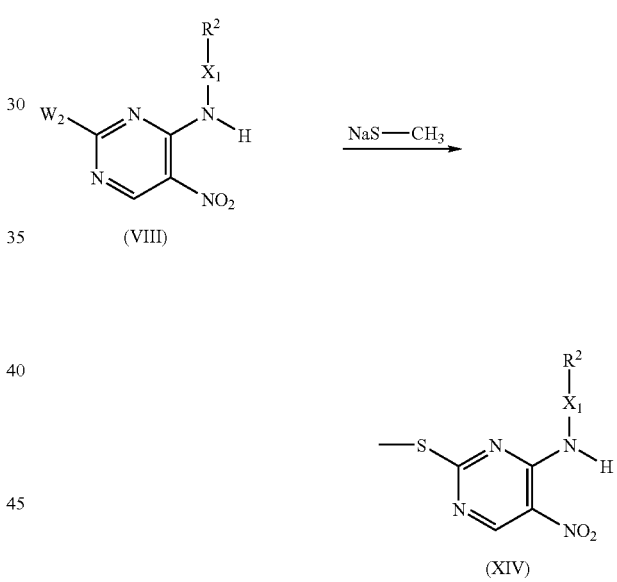

Intermediates of formula (XIV) can also be prepared by reacting an intermediate of formula (IX) with an intermediate of formula (VII) in the presence of NaCH$_2$SH and a suitable solvent, such as for example N,N-dimethylformamide.

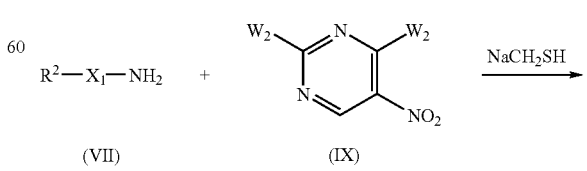

-continued

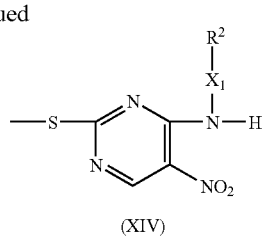

(XIV)

Intermediates of formula (XV) can be prepared by reacting an intermediate of formula (XVII) with N,N-dimethylformamide (DMF) in the presence of a suitable base, such as for example diethylamine.

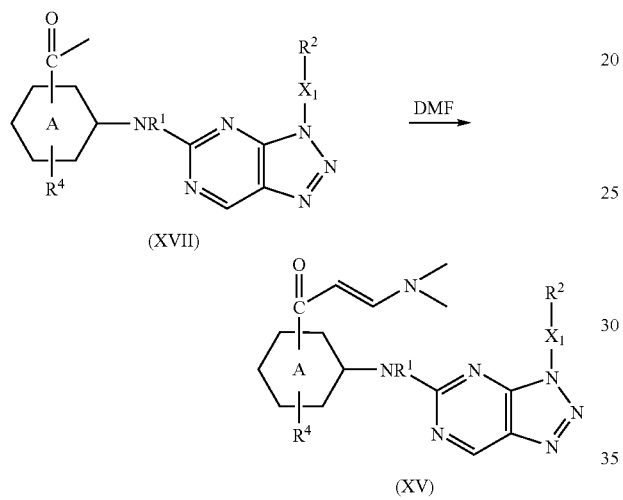

Intermediates of formula (XV) wherein $R^1$ represents ethyl, said intermediates being represented by formula (XV-a), can be prepared by reacting an intermediate of formula (XV) wherein $R^1$ is hydrogen, said intermediate being represented by formula (XV-b) in the presence of N,N-diethylethanamine, and a suitable solvent, such as for example N,N-dimethylformamide.

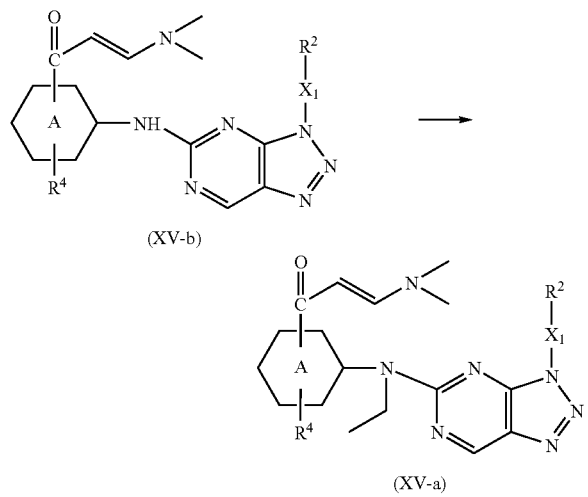

Intermediates of formula (XVII) can be prepared by reacting an intermediate of formula (III) with an intermediate of formula (XVIII) in the presence of a suitable solvent, such as for example dimethylsulfoxide, $CH_3$—O—$CH_2$—$CH_2$—OH or $(CH_3)_2N$—C(=O)H in the presence of NaH.

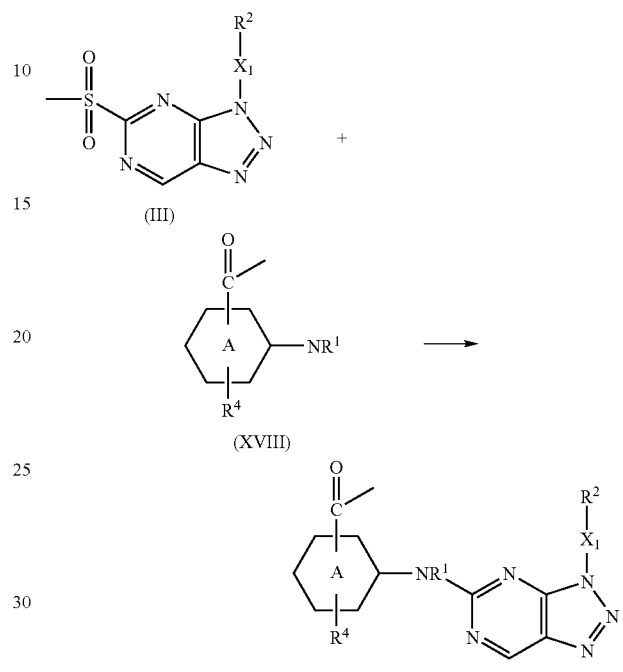

Intermediates of formula (III') can be prepared by cyclizing an intermediate of formula (XXIII) in the presence of a nitrite salt, such as for example $NaNO_2$, a suitable acid, such as for example hydrochloric acid, e.g. HCl 6N or HCl 1N, and/or acetic acid and the like, and optionally in the presence of a suitable solvent, such as for example water.

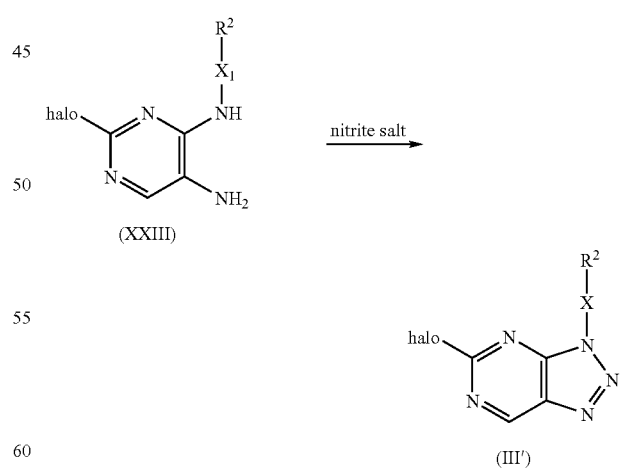

Intermediates of formula (XXIII) can be prepared by reducing an intermediate of formula (XXIV) with a suitable reducing agent, such as for example $H_2$, in the presence of a suitable catalyst, such as for example platina on charcoal, in the presence of a suitable catalyst poison, such as for example a thiophene solution, in the presence of a suitable solvent, such as for example N,N-dimethylacetamide, tetrahydrofuran, N,N-dimethylformamide or a suitable alcohol, such as for example methanol, ethanol and the like, and in the presence of a suitable base, such as for example N,N-diethylethanamine.

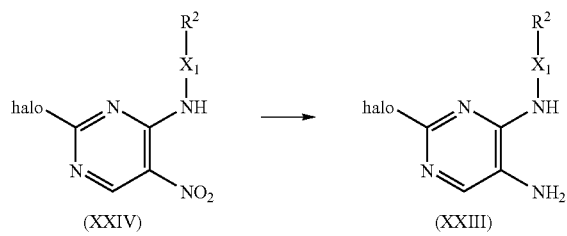

Intermediates of formula (XXIV) can be prepared by reacting an intermediate of formula (VII) with an intermediate of formula (IX) wherein $W_2$ represents halo, said intermediate being represented by formula (IX-a), in the presence of a suitable solvent, such as for example methylene chloride, and a suitable base, such as for example N,N-dimethylbenzenamine.

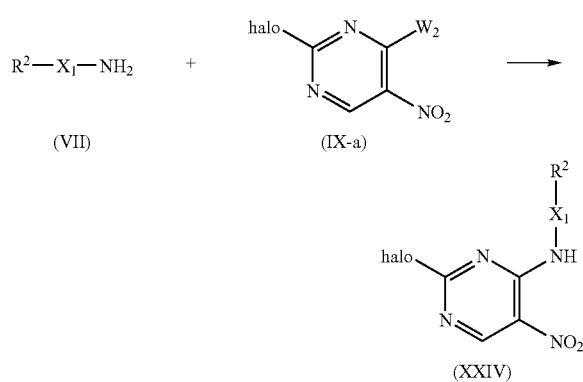

The compounds of formula (I) inhibit Glycogen synthase kinase 3 (GSK3), in particular glycogen synthase kinase 3 alpha (GSK3α) and/or glycogen synthase kinase 3 beta (GSK3β). They are selective Glycogen synthase kinase 3 inhibitors. Specific inhibitory compounds are superior therapeutic agents since they are characterized by a greater efficacy and lower toxicity by virtue of their specificity.

Synonyms for GSK3 are tau protein kinase I (TPK I), FA (Factor A) kinase, kinase FA and ATP-citrate lysase kinase (ACLK).

Glycogen synthase kinase 3 (GSK3), which exists in two isoforms as already stated above, i.e. GSK3α and GSK3β, is a proline-directed serine/threonine kinase originally identified as an enzyme that phosphorylates glycogen synthase. However, it has been demonstrated that GSK3 phosphorylates numerous proteins in vitro such as glycogen synthase, phosphatase inhibitor 1-2, the type-II subunit of cAMP-dependent protein kinase, the G-subunit of phosphatase-1, ATP-citrate lyase, acetyl coenzyme A carboxylase, myelin basic protein, a microtubule-associated protein, a neurofilament protein, an N-CAM cell adhesion molecule, nerve growth factor receptor, c-Jun transcription factor, JunD transcription factor, c-Myb transcription factor, c-Myc transcription factor, L-Myc transcription factor, adenomatous polyposis coli tumor supressor protein, tau protein and β-catenin.

The above-indicated diversity of proteins which may be phosphorylated by GSK3 implies that GSK3 is implicated in numerous metabolic and regulatory processes in cells.

GSK3 inhibitors may therefore be useful in the prevention or treatment of diseases mediated through GSK3 activity such as bipolar disorder (in particular manic depression), diabetes, Alzheimer's disease, leukopenia, FTDP-17 (Fronto-temporal dementia associated with Parkinson's disease), cortico-basal degeneration, progressive supranuclear palsy, multiple system atrophy, Pick's disease, Niemann Pick's disease type C, Dementia Pugilistica, dementia with tangles only, dementia with tangles and calcification, Downs syndrome, myotonic dystrophy, Parkinsonism-dementia complex of Guam, aids related dementia, Postencephalic Parkinsonism, prion diseases with tangles, subacute sclerosing panencephalitis, frontal lobe degeneration (FLD), argyrophilic grains disease, subacute sclerotizing panencephalitis (SSPE) (late complication of viral infections in the central nervous system), inflammatory diseases, depression, cancer, dermatological disorders such as baldness, neuroprotection, schizophrenia, pain, in particular neuropathic pain. GSK3 inhibitors can also be used to inhibit sperm motility and can therefore be used as male contraceptives.

In particular, the compounds of the present invention are useful in the prevention or treatment of Alzheimer's disease; diabetes, in particular type 2 diabetes (non insulin dependent diabetes); bipolar disorder; cancer; pain, in particular neuropathic pain; depression; inflammatory diseases. More in particular, the compounds of the present invention are useful in the prevention or treatment of diabetes, in particular type 2 diabetes (non insulin dependent diabetes); pain, in particular neuropathic pain; depression; inflammatory diseases.

The major neuropathological landmarks in Alzheimer's disease are neuronal loss, the deposition of amyloid fibers and paired helical filaments (PHF) or neurofibrillary tangles (NFT). Tangle formation appears to be the consequence of accumulation of aberrantly phosphorylated tau protein. This aberrant phosphorylation destabilizes neuronal cytoskeleton, which leads to reduced axonal transport, deficient functioning and ultimately neuronal death. The density of neurofibrillary tangles has been shown to parallel duration and severity of Alzheimer's disease. Reduction of the degree of tau phosphorylation can provide for neuroprotection and can prevent or treat Alzheimer's disease or can slow the progression of the disease. As mentioned hereinabove, GSK3 phosphorylates tau protein. Thus compounds having an inhibitory activity for GSK3 may be useful for the prevention or the treatment of Alzheimer's disease.

Insulin regulates the synthesis of the storage polysaccharide glycogen. The rate-limiting step in the glycogen synthesis is catalyzed by the enzyme glycogen synthase. It is believed that glycogen synthase is inhibited by phosphorylation and that insulin stimulates glycogen synthase by causing a net decrease in the phosphorylation of this enzyme. Thus, in order to activate glycogen synthase, insulin must either activate phosphatases or inhibit kinases, or both.

It is believed that glycogen synthase is a substrate for glycogen synthase kinase 3 and that insulin inactivates GSK3 thereby promoting the dephosphorylation of glycogen synthase.

In addition to the role of GSK3 in insulin-induced glycogen synthesis, GSK3 may also play a role in insulin resistance. It is believed that GSK3 dependent Insulin Receptor Substrate-1 phosphorylation contributes to insulin resistance.

Therefore, GSK3 inhibition may result in the increased deposition of glycogen and a concomitant reduction of blood glucose, thus mimicing the hypoglycemic effect of insulin. GSK3 inhibition provides an alternative therapy to manage insulin resistance commonly observed in non insulin dependent diabetes mellitus and obesity. GSK3 inhibitors may thus provide a novel modality for the treatment of type 1 and type 2 diabetes.

GSK3 inhibitors may also be indicated for use in the prevention or the treatment of pain, in particular neuropathic pain.

After axotomy or chronic constriction injury, neuronal cells die through an apoptotic pathway and the morphological changes correlate with the onset of hyperalgesia and/or allodynia.

The induction of apoptosis is probably triggered by a reduced supply of neurotrophic factors as the time course of neuronal loss is positively altered by administration of neurotrophins. GSK has been shown to be involved in the initiation of the apoptotic cascade and trophic factor withdrawal stimulates the GSK3 apoptosis pathway.

In view of the above, GSK3 inhibitors might reduce signals of and even prevent levels of neuropathic pain.

Due to their GSK3 inhibitory properties, the compounds of formula (I), their N-oxides, pharmaceutically acceptable addition salts, quaternary amines and stereochemically isomeric forms thereof, are useful to prevent or treat GSK3 mediated diseases, such as bipolar disorder (in particular manic depression), diabetes, Alzheimer's disease, leukopenia, FTDP-17 (Fronto-temporal dementia associated with Parkinson's disease), cortico-basal degeneration, progressive supranuclear palsy, multiple system atrophy, Pick's disease, Niemann Pick's disease type C, Dementia Pugilistica, dementia with tangles only, dementia with tangles and calcification, Downs syndrome, myotonic dystrophy, Parkinsonism-dementia complex of Guam, aids related dementia, Postencephalic Parkinsonism, prion diseases with tangles, subacute sclerosing panencephalitis, frontal lobe degeneration (FLD), argyrophilic grains disease, subacute sclerotizing panencephalitis (SSPE) (late complication of viral infections in the central nervous system), inflammatory diseases, depression, cancer, dermatological disorders such as baldness, neuroprotection, schizophrenia, pain, in particular neuropathic pain. The present compounds are also useful as male contraceptives. In general, the compounds of the present invention may be useful in the treatment of warm-blooded animals suffering from a disease mediated through GSK3, or they may be useful to prevent warm-blooded animals to suffer from disease mediated through GSK3. More in particular, the compounds of the present invention may be useful in the treatment of warm-blooded animals suffering from Alzheimer's disease; diabetes, in particular type 2 diabetes; cancer; inflammatory diseases; bipolar disorder; depression; pain, in particular neuropathic pain. Even more in particular, the compounds of the present invention may be useful in the treatment of warm-blooded animals suffering from diabetes, in particular type 2 diabetes; inflammatory diseases; depression; pain, in particular neuropathic pain.

In view of the above described pharmacological properties, the compounds of formula (I) or any subgroup thereof, their N-oxides, pharmaceutically acceptable addition salts, quaternary amines and stereochemically isomeric forms, may be used as a medicine. In particular, the present compounds can be used for the manufacture of a medicament for treating or preventing diseases mediated through GSK3. More in particular, the present compounds can be used for the manufacture of a medicament for treating or preventing Alzheimer's disease; diabetes, in particular type 2 diabetes; cancer; inflammatory diseases; bipolar disorder; depression; pain, in particular neuropathic pain. Even more in particular, the present compounds can be used for the manufacture of a medicament for treating or preventing diabetes, in particular type 2 diabetes; inflammatory diseases; depression; pain, in particular neuropathic pain.

In view of the utility of the compounds of formula (I), there is provided a method of treating warm-blooded animals, including humans, suffering from or a method of preventing warm-blooded animals, including humans, to suffer from diseases mediated through GSK3, more in particular a method of treating or preventing Alzheimer's disease; diabetes, in particular type 2 diabetes; cancer; inflammatory diseases; bipolar disorder; depression; pain, in particular neuropathic pain, even more in particular diabetes, in particular type 2 diabetes; inflammatory diseases; depression; pain, in particular neuropathic pain. Said method comprises the administration, preferably oral administration, of an effective amount of a compound of formula (I), a N-oxide form, a pharmaceutically acceptable addition salt, a quaternary amine or a possible stereoisomeric form thereof, to warm-blooded animals, including humans.

The present invention also provides compositions for preventing or treating diseases mediated through GSK3, comprising a therapeutically effective amount of a compound of formula (I), a N-oxide, a pharmaceutically acceptable addition salt, a quaternary amine and a stereochemically isomeric form thereof, and a pharmaceutically acceptable carrier or diluent.

The compounds of the present invention or any subgroup thereof may be formulated into various pharmaceutical forms for administration purposes. As appropriate compositions there may be cited all compositions usually employed for systemically administering drugs. To prepare the pharmaceutical compositions of this invention, an effective amount of the particular compound, optionally in addition salt form, as the active ingredient is combined in intimate admixture with a pharmaceutically acceptable carrier, which carrier may take a wide variety of forms depending on the form of preparation desired for administration. These pharmaceutical compositions are desirable in unitary dosage form suitable, particularly, for administration orally, rectally, percutaneously, or by parenteral injection. For example, in preparing the compositions in oral dosage form, any of the usual pharmaceutical media may be employed such as, for example, water, glycols, oils, alcohols and the like in the case of oral liquid preparations such as suspensions, syrups, elixirs, emulsions and solutions; or solid carriers such as starches, sugars, kaolin, diluents, lubricants, binders, disintegrating agents and the like in the case of powders, pills, capsules, and tablets. Because of their ease in administration, tablets and capsules represent the most advantageous oral dosage unit forms, in which case solid pharmaceutical carriers are obviously employed. For parenteral compositions, the carrier will usually comprise sterile water, at least in large part, though other ingredients, for example, to aid solubility, may be included. Injectable solutions, for example, may be prepared in which the carrier comprises saline solution, glucose solution or a mixture of saline and glucose solution. Injectable suspensions may also be prepared in which case appropriate liquid carriers, suspending agents and the like may be employed. Also included are solid form preparations which are intended to be converted, shortly before use, to liquid form preparations. In the compositions suitable for percutaneous administration, the carrier optionally comprises a penetration enhancing agent and/or a suitable wetting agent, optionally combined with suitable additives of any nature in minor proportions, which additives do not introduce a significant deleterious effect on the skin. Said additives may facilitate the administration to the skin and/or may be helpful for preparing the desired compositions. These compositions may be administered in various ways, e.g., as a transdermal patch, as a spot-on, as an ointment. The compounds of the present invention may also be administered via inhalation or insufflation by means of methods and formulations employed in the art for administration via this way. Thus, in general the compounds of the present invention may be administered to the lungs in the form of a solution, a suspension or a dry powder. Any system developed for the delivery of solutions, suspensions or dry powders via oral or nasal inhalation or insufflation are suitable for the administration of the present compounds.

It is especially advantageous to formulate the aforementioned pharmaceutical compositions in unit dosage form for ease of administration and uniformity of dosage. Unit dosage form as used herein refers to physically discrete units suitable as unitary dosages, each unit containing a predetermined quantity of active ingredient calculated to produce the desired therapeutic effect in association with the required pharmaceutical carrier. Examples of such unit dosage forms are tablets (including scored or coated tablets), capsules, pills, powder packets, wafers, suppositories, injectable solutions or suspensions and the like, and segregated multiples thereof.

The present compounds are orally active compounds, and are preferably orally administered.

The exact dosage, the therapeutically effective amount and frequency of administration depends on the particular compound of formula (I) used, the particular condition being treated, the severity of the condition being treated, the age, weight, sex, extent of disorder and general physical condition of the particular patient as well as other medication the individual may be taking, as is well known to those skilled in the art. Furthermore, it is evident that said effective daily amount may be lowered or increased depending on the response of the treated subject and/or depending on the evaluation of the physician prescribing the compounds of the instant invention.

When used as a medicament to prevent or treat Alzheimer's disease, the compounds of formula (I) may be used in combination with other conventional drugs used to combat Alzheimer's disease, such as galantamine, donepezil, rivastigmine or tacrine. Thus, the present invention also relates to the combination of a compound of formula (I) and another agent capable of preventing or treating Alzheimer's disease. Said combination may be used as a medicine. The present invention also relates to a product containing (a) a compound of formula (I), and (b) another agent capable of preventing or treating Alzheimer's disease, as a combined preparation for simultaneous, separate or sequential use in the prevention or treatment of Alzheimer's disease. The different drugs may be combined in a single preparation together with pharmaceutically acceptable carriers.

When used as a medicament to prevent or treat type 2 diabetes, the compounds of formula (I) may be used in combination with other conventional drugs used to combat type 2 diabetes, such as glibenclamide, chlorpropamide, gliclazide, glipizide, gliquidon, tolbutamide, metformin, acarbose, miglitol, nateglinide, repaglinide, acetohexamide, glimepiride, glyburide, tolazamide, troglitazone, rosiglitazone, pioglitazone, isaglitazone.

Thus, the present invention also relates to the combination of a compound of formula (I) and another agent capable of preventing or treating type 2 diabetes. Said combination may be used as a medicine. The present invention also relates to a product containing (a) a compound of formula (I), and (b) another agent capable of preventing or treating type 2 diabetes, as a combined preparation for simultaneous, separate or sequential use in the prevention or treatment of type 2 diabetes. The different drugs may be combined in a single preparation together with pharmaceutically acceptable carriers.

When used as a medicament to prevent or treat cancer, the compounds of formula (I) may be used in combination with other conventional drugs used to combat cancer such as platinum coordination compounds for example cisplatin or carboplatin; taxane compounds for example paclitaxel or docetaxel; camptothecin compounds for example irinotecan or topotecan; anti-tumour vinca alkaloids for example vinblastine, vincristine or vinorelbine; anti-tumour nucleoside derivatives for example 5-fluorouracil, gemcitabine or capecitabine; nitrogen mustard or nitrosourea alkylating agents for example cyclophosphamide, chlorambucil, carmustine or lomustine; anti-tumour anthracycline derivatives for example daunorubicin, doxorubicin or idarubicin; $HER^2$ antibodies for example trastzumab; and anti-tumour podophyllotoxin derivatives for example etoposide or teniposide; and antiestrogen agents including estrogen receptor. antagonists or selective estrogen receptor modulators preferably tamoxifen, or alternatively toremifene, droloxifene, faslodex and raloxifene; aromatase inhibitors such as exemestane, anastrozole, letrazole and vorozole; differentiating agents for example retinoids, vitamin D and DNA methyl transferase inhibitors for example azacytidine; kinase inhibitors for example flavoperidol and imatinib mesylate or farnesyltransferase inhibitors for example R115777.

Thus, the present invention also relates to the combination of a compound of formula (I) and another agent capable of preventing or treating cancer. Said combination may be used as a medicine. The present invention also relates to a product containing (a) a compound of formula (I), and (b) another agent capable of preventing or treating cancer, as a combined preparation for simultaneous, separate or sequential use in the prevention or treatment of cancer. The different drugs may be combined in a single preparation together with pharmaceutically acceptable carriers.

When used as a medicament to prevent or treat bipolar disorder, the compounds of formula (I) may be used in combination with other conventional drugs used to combat bipolar disorder such as neuroleptica, atypical antipsychotics, anti-epileptica, benzodiazepines, lithium salts, for example olanzapine, risperidone, carbamazepine, valproate, topiramate.

Thus, the present invention also relates to the combination of a compound of formula (I) and another agent capable of preventing or treating bipolar disorder. Said combination may be used as a medicine. The present invention also relates to a product containing (a) a compound of formula (I), and (b) another agent capable of preventing or treating bipolar disorder, as a combined preparation for simultaneous, separate or sequential use in the prevention or treatment of bipolar disorder. The different drugs may be combined in a single preparation together with pharmaceutically acceptable carriers.

When used as a medicament to prevent or treat inflammatory diseases, the compounds of formula (I) may be used in combination with other conventional drugs used to combat inflammatory diseases such as steroids, cyclooxygenase-2 inhibitors, non-steroidal-anti-inflammatory drugs, TNF-α antibodies, such as for example acetyl salicylic acid, bufexamac, diclofenac potassium, sulindac, diclofenac sodium, ketorolac trometamol, tolmetine, ibuprofen, naproxen, naproxen sodium, tiaprofen acid, flurbiprofen, mefenamic acid, nifluminic acid, meclofenamate, indomethacin, proglumetacine, ketoprofen, nabumetone, paracetamol, piroxicam, tenoxicam, nimesulide, fenylbutazon, tramadol, beclomethasone dipropionate, betamethasone, beclamethasone, budesonide, fluticasone, mometasone, dexamethasone, hydrocortisone, methylprednisolone, prednisolone, prednisone, triamcinolone, celecoxib, rofecoxib, infliximab, leflunomide, etanercept, CPH 82, methotrexate, sulfasalazine.

Thus, the present invention also relates to the combination of a compound of formula (I) and another agent capable of preventing or treating inflammatory diseases. Said combination may be used as a medicine. The present invention also relates to a product containing (a) a compound of formula (I), and (b) another agent capable of preventing or treating inflammatory diseases, as a combined preparation for simultaneous, separate or sequential use in the prevention or treatment of inflammatory disorders. The different drugs may be combined in a single preparation together with pharmaceutically acceptable carriers.

When used as a medicament to prevent or treat depression, the compounds of formula (I) may be used in combination with other conventional drugs used to combat depression such as norepinephrine reuptake inhibitors, selective serotonin reuptake inhibitors (SSRI's), monoamine oxidase inhibitors (MAOI's), reversible inhibitors of monoamine oxidase (RIMA's), serotonin and noradrenaline reuptake inhibitors (SNRI's), noradrenergic and specific serotonergic antidepressants (NaSSA's), corticotropin releasing factor (CRF) antagonists, α-adrenoreceptor antagonists and atypical antidepressants.

Suitable examples of norepinephrine reuptake inhibitors include amitriptyline, clomipramine, doxepin, imipramine, trimipramine, amoxapine, desipramine, maprotiline, nortriptyline, protriptyline, reboxetine and pharmaceutically acceptable salts thereof.

Suitable examples of selective serotonin reuptake inhibitors include fluoxetine, fluvoxamine, paroxetine, sertraline and pharmaceutically acceptable salts thereof.

Suitable examples of monoamine oxidase inhibitors include isocarboxazid, phenelzine, tranylcypromine, selegiline and pharmaceutically acceptable salts thereof.

Suitable examples of reversible inhibitors of monoamine oxidase include moclobemide and pharmaceutically acceptable salts thereof.

Suitable examples of serotonin and noradrenaline reuptake inhibitors include venlafaxine and pharmaceutically acceptable salts thereof.

Suitable atypical antidepressants include bupropion, lithium, nefazodone, trazodone, viloxazine, sibutramine and pharmaceutically acceptable salts thereof.

Other suitable antidepressants include adinazolam, alaproclate, amineptine, amitriptyline/chlordiazepoxide combination, atipamezole, azamianserin, bazinaprine, befuraline, bifemelane, binodaline, bipenamol, brofaromine, bupropion, caroxazone, cericlamine, cianopramine, cimoxatone, citalopram, clemeprol, clovoxamine, dazepinil, deanol, demexiptiline, dibenzepin, dothiepin, droxidopa, enefexine, estazolam, etoperidone, femoxetine, fengabine, fezolamine, fluotracen, idazoxan, indalpine, indeloxazine, iprindole, levoprotiline, litoxetine, lofepramine, medifoxamine, metapramine, metralindole, mianserin, milnacipran, minaprine, mirtazapine, monirelin, nebracetam, nefopam, nialamide, nomifensine, norfluoxetine, orotirelin, oxaflozane, pinazepam, pirlindone, pizotyline, ritanserin, rolipram, sercloremine, setiptiline, sibutramine, sulbutiamine, sulpiride, teniloxazine, thozalinone, thymoliberin, tianeptine, tiflucarbine, tofenacin, tofisopam, toloxatone, tomoxetine, veralipride, viqualine, zimelidine and zometapine and pharmaceutically acceptable salts thereof, and St. John's wort herb, or *Hypericum perforatum*, or extracts thereof. Thus, the present invention also relates to the combination of a compound of formula (I) and another agent capable of preventing or treating depression. Said combination may be used as a medicine. The present invention also relates to a product containing (a) a compound of formula (I), and (b) another agent capable of preventing or treating depression, as a combined preparation for simultaneous, separate or sequential use in the prevention or treatment of depression. The different drugs may be combined in a single preparation together with pharmaceutically acceptable carriers.

When used as a medicament to prevent or treat pain, the compounds of formula (I) may be used in combination with other conventional drugs used to combat pain such as nonsteroidal anti-inflammatory drugs (NSAIDS), centrally acting analgesics.

Suitable nonsteroidal anti-inflammatory drugs include salicylates, such as for example acetylsalicylic acid, ethenzamide, salicylamide; para-aminophenol derivatives, such as for example paracetamol, propacetamol, phenidine; anthranilates, such as for example etofenamate, flufenamic acid, meclofenamic acid, mefenamic acid, niflumic acid; arylacetic acids, such as for example acemetacin, bufexamac, diclofenac, indomethacin, lonazolac, sulindac, tolmetin, nabumetone; arylpropionic acids, such as for example flurbiprofen, ibuprofen, ketoprofen, naproxen, tiaprofenic acid; pyrazolinone derivatives, such as for example metamizol, propyphenazone; pyrazolidine-3,5-diones, such as for example kebuzone, mofebutazone, oxyphenbutazone, phenylbutazone; arylsulfonamides, such as for example isoxicam, lomoxicam, piroxicam, tenoxicam; ketorolac; oxaprozine; Cox-2 inhibitors, such as for example celecoxib, etodolac, meloxicam, nimesulfide, rofecoxib.

Suitable centrally acting analgesics include opioid agonists, such as for example morphine and morphinane derivatives, e.g. morphine, codeine, ethyimorphine, diacetylmorphine, dihydrocodeine, etorphine, hydrocodone, hydromorphone, levorphanol, oxycodone, oxymorphone; such as for example piperidine derivatives, e.g. pethidine, ketobemidone, fentanyl, alfentanil, remifentanil, sufentanil; such as for example methadone and congeners, e.g. levomethadone, levomethadone acetate, dextromoramide, dextropropoxyphene, diphenoxylate, loperamide, piritramide; tilidine; tramadol; viminol.

Suitable centrally acting analgesics include mixed opioid agonist-antagonists and partial agonists, such as for example buprenorphine, butorphanol, dezocine, meptazinol, nalbuphine, nalorphine, pentazocine; opioid antagonists, such as for example levallorphan, naloxone, naltrexone; non-opioid compounds, such as for example carbamazepine, clonidine, flupirtine, nefopam.

Thus, the present invention also relates to the combination of a compound of formula (I) and another agent capable of preventing or treating pain. Said combination may be used as a medicine. The present invention also relates to a product containing (a) a compound of formula (I), and (b) another agent capable of preventing or treating pain, as a combined preparation for simultaneous, separate or sequential use in the prevention or treatment of bipolar disorder. The different drugs may be combined in a single preparation together with pharmaceutically acceptable carriers.

The following examples illustrate the present invention.

Experimental Part

Hereinafter, "DMF" is defined as N,N-dimethylformamide, "DIPE" is defined as diisopropylether, "DMSO" is defined as dimethylsulfoxide, "THF" is defined as tetrahydrofuran, "DMA" is defined as N,N-dimethylacetamide and "DIPEA" is defined as N,N-diisopropylethanamine.

A. Preparation of the Intermediate Compounds

EXAMPLE A1 a. Preparation of Intermediate 1

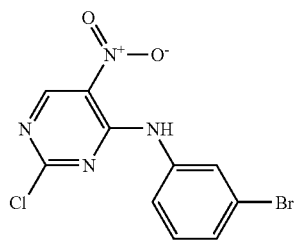

A mixture of 2,4-dichloro-5-nitropyrimidine (0.05 mol) in DMA (400 ml) was cooled. to −20° C. and N-ethyl-N-(1-methylethyl)-2-propanamine (0.05 mol) was added, then a mixture of 3-bromo-benzeneamine (0.05 mol) in DMA (200 ml) was added dropwise at −20° C. and the reaction mixture was stirred at −20° C. for 2 hours. The reaction mixture was used as such in the next reaction step.

b. Preparation of Intermediate 2

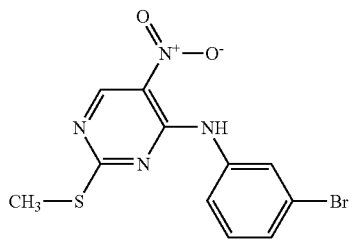

NaSCH$_3$, 21% in H$_2$O (0.05 mol) was added dropwise to intermediate 1 (0.05 mol) and the reaction mixture was stirred for 1.5 hours at room temperature, then the mixture was carefully poured out into H$_2$O. The resulting precipitate was stirred over the weekend, filtered off, washed and dried (vac.), yielding 15.73 g (92.5%). The product was crystallised from CH$_3$CN, then the resulting precipitate was filtered off, washed and dried (vacuum). The product was crystallised from CH3CN, then the resulting precipitate was filtered off, washed and dried (vacuum), yielding intermediate 2.

c. Preparation of Intermediate 3

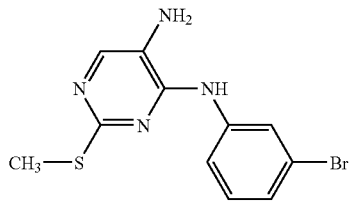

A mixture of intermediate 2 (0.028 mol) in CH$_3$OH (250 ml) was hydrogenated with Pt/C 5% (2g) as a catalyst in the presence of a solution of thiophene in DIPE (4%, 1 ml). After uptake of H$_2$ (3 equiv.), the catalyst was filtered off and the filtrate was evaporated. The residue was crystallised from CH$_3$CN, then the resulting precipitate was filtered off, washed and dried (vacuum). Yield: 5.2 g of intermediate 3

EXAMPLE A1a

Preparation of Intermediate 34

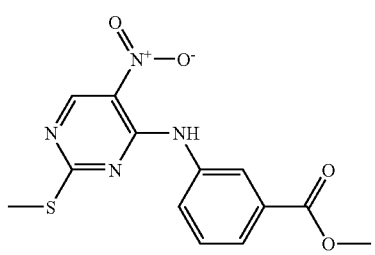

A mixture of 2,4-dichloro-5-nitropyrimidine (0.033 mol) in DMF p.a. (100 ml) was stirred under N$_2$ at −50° C., then a solution of 3-aminobenzoic acid methyl ester (0.033 mol) in DMF p.a. (30 ml) was added dropwise and the reaction mixture was stirred for 2 hours at −40 á −50° C. The mixture was allowed to warm a little while to 0° C. and was cooled again to −40° C. NaSCH$_3$ (21% in H$_2$O) (0.066 mol) was added dropwise and the reaction mixture was allowed to slowly reach room temperature, then the mixture was stirred for 1 hour at room temperature. Ice-water (100 ml) was added and the mixture was stirred for 30 minutes, then the resulting precipitate was filtered off and dried. Yield: 7.94 g of intermediate compound 34 (75%).

EXAMPLE A2 a. Preparation of Intermediate 4

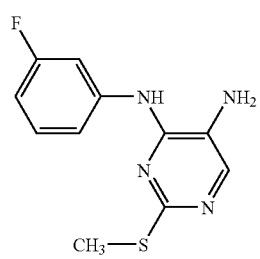

A mixture of

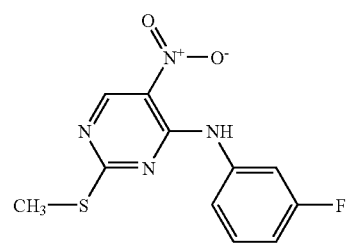

(prepared according to A1.b) (0.07 mol) and Et$_3$N (10 g) in THF (250 ml) was hydrogenated with Pd/C, 10% (5 g) as a catalyst in the presence of a solution of thiophene in DIPE (4%, 5 ml). After uptake of H₂ (3 equiv), the catalyst was filtered off and the filtrate was evaporated. The residue was stirred in DIPE with a small amount of CH₃CN. The precipitate was filtered off and dried. Yield: 12.3 g of intermediate 4 (70.2%). The filtrate was acidified with HCl/2-propanol while stirring. The mixture was stirred for 30 minutes. The resulting precipitate was filtered off and dried. Yield: 5.17 g of intermediate 4 (25.7%).

b. Preparation of Intermediate 5

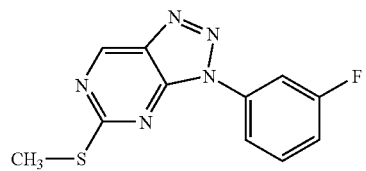

Intermediate 4 (0.08 mol) was dissolved in a mixture of 6N HCl (400 ml) and HOAc, p.a. (400 ml) and the whole was cooled to 0-5° C. A solution of NaNO₂ (0.1 mol) in H₂O (40 ml) was added dropwise over a 30 minutes period. Then, the reaction mixture was stirred for another 30 minutes while cooling on the ice-bath. Then, the mixture was stirred overnight at room temperature. The resulting precipitate was filtered off, rinsed with water, with 2-propanone, then with DIPE, and dried. Yield: 18.14 g of intermediate 5 (87%).

c-1. Preparation of Intermediate 6

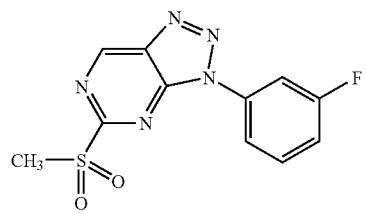

Intermediate 5 (15 g, 0.058 mol) was stirred in HOAc (700 ml) and cooled on an ice-bath. A solution of KMnO₄, p.a. (24 g, 0.15 mol) in demineralized H2O, (300 ml) was added dropwise over a 60 minutes period while cooling on an ice-bath. The mixture was stirred for one hour on the ice-bath, then for 2 hours at room temperature. Sodium bisulfite was added until a colour change resulted. EtOAc (same quantity) was added while stirring vigorously for a while. The mixture was stood overnight. The mixture was concentrated to ~50-ml volume. The aqueous concentrate was stirred for a while and the resulting precipitate was filtered off and dried. Yield: 11.023 g of intermediate 6 (64.8%).

c-2. Preparation of Intermediate 23

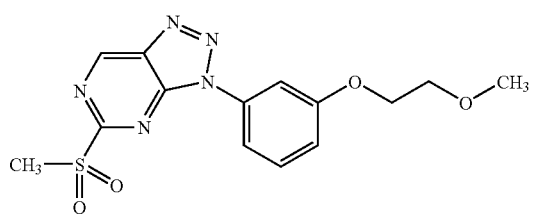

A mixture of 3-chlorobenzenecarboperoxoic acid (0.0125 mol, dry) in CH₂Cl₂ (100 ml) was dried (MgSO₄), filtered off and the filtrate was added dropwise to a solution of intermediate 22 (prepared according to A2.b, structure see below) (0.0063 mol) in CH₂Cl₂ (100 ml), then the reaction mixture was stirred overnight at room temperature and washed with a NaHCO₃/H₂O solution. The organic layer was separated, dried (MgSO₄), filtered off and the solvent was evaporated. The residue was suspended in DIPE/CH₃CN, then the desired product was filtered off, washed and dried (vacuum). Yield: 1.9 g of intermediate 23.

Intermediate 22

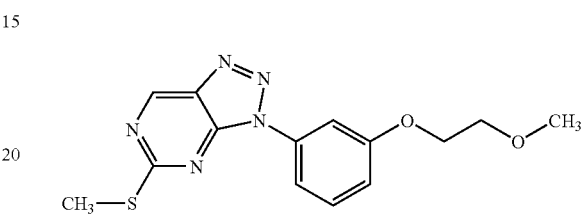

c-3. Preparation of Intermediate 25

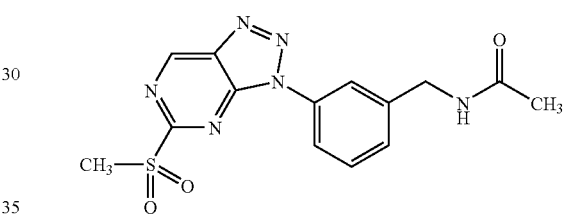

A mixture of intermediate 24

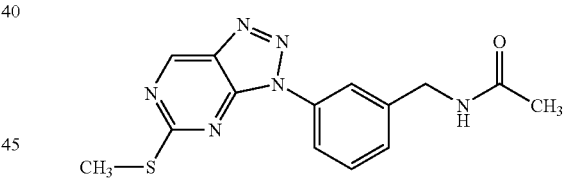

(prepared according to A2.b) (0.02 mol) in CH₂Cl₂, p.a. (250 ml) and methanol, p.a. (50 ml) was stirred at room temperature until complete dissolution and then 3-chlorobenzenecarboperoxoic acid (0.04 mol, 70%) was added portionwise. The reaction mixture was stirred for 2 hours at room temperature and extra 3-chlorobenzenecarboperoxoic acid (2×2.5 g, every half hour) was added. The resulting mixture was stirred overnight at room temperature and washed with a calculated NaHCO₃/H₂O solution. The organic layer was separated, dried (MgSO₄), filtered off and the solvent was evaporated. The residue was crystallised from CH₃CN, then the resulting precipitate was filtered off and dried. The filtrate was evaporated and the residue was purified by Flash column chromatography (eluent: CH₂Cl₂/CH₃OH 98/2). The product fractions were collected and the solvent was evaporated. The residue was recrystallised from CH₃OH with a small amount of H₂O, then the resulting precipitate was filtered off and dried. Yield: 1.984 g of intermediate 25 (29%).

c-4a. Preparation of Intermediate 27

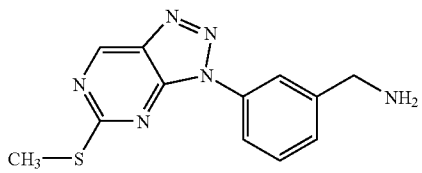

A mixture of intermediate 24 (prepared according to A2.b) (0.020 mol) in 12N HCl, p.a. (100 ml) and H$_2$O (demineralised) (200 ml) was stirred and refluxed for 6 hours, then the reaction mixture was stirred over the weekend at room temperature. The resulting precipitate was filtered off and dried. Yield: 3.61 g of intermediate 27 (58.5 %, m.p.: >260° C.).

c-4b. Preparation of Intermediate 28

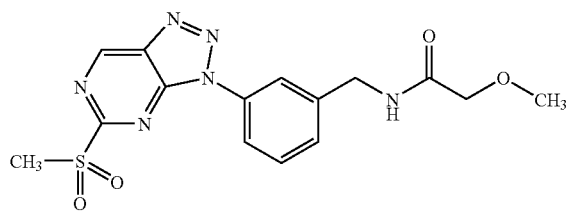

A mixture of intermediate 27 (prepared according to A2.c-4a) (0.001 mol) and Et$_3$N (0.0025 mol) in CH$_2$Cl$_2$, p.a. (15 ml) was stirred at room temperature and a mixture of methoxyacetyl chloride (0.0012 mol) in CH$_2$Cl$_2$, p.a. (1 ml) was added dropwise, then the reaction mixture was stirred overnight at room temperature and washed with H$_2$O. The organic layer was separated, dried, filtered off and the solvent was evaporated. The residue was dissolved in CH$_2$Cl$_2$ (15 ml) and 3-chlorobenzenecarboperoxoic acid (0.002 mol, 70%) was added. The resulting mixture was stirred for 2 hours at room temperature and washed with a NaHCO$_3$ solution. The organic layer was separated, dried, filtered off and the solvent was evaporated. The residue was stirred overnight in DIPE and then the resulting precipitate was filtered off and dried. Yield: 0.392 g intermediate 28 (100%).

c-5. Preparation of Intermediate 32

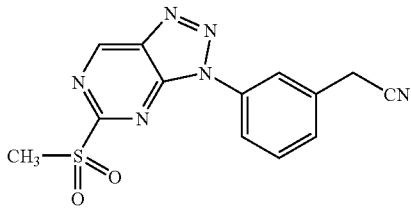

A mixture of intermnediate 31

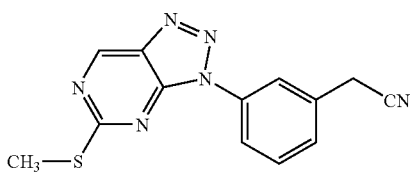

(prepared according to A2.b) (0.010 mol) in CH2Cl$_2$ (80 ml) and methanol (20 ml) was stirred at room temperature and 3-chlorobenzenecarboperoxoic acid (0.024 mol) was added portionwise. The reaction mixture was stirred for 3 hours at room temperature, then a mixture of NaHCO$_3$ (0.025 mol) in H$_2$O was added and the resulting mixture was stirred firmly. When the generation of gas was stopped, the layers were separated. The organic layer was dried (MgSO$_4$), filtered off and the solvent was evaporated. The residue was stirred in DEPE with a small amound of CH$_3$CN, then the precipitate was filtered off and dried. Yield: 1.218 g of intermediate 32 (39%).

c-6. Preparation of Intermediate 40

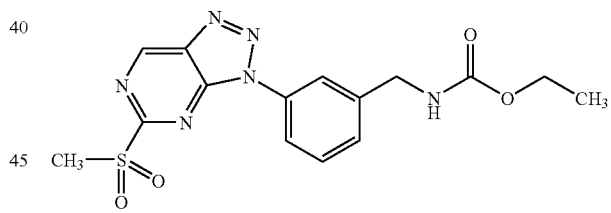

A mixture of intermediate 27 (prepared according to A2.c-4a) (0.005 mol) in CH$_2$Cl$_2$ (50 ml) was stirred at room temperature and morpholinomethyl Polystyrene HL resin (loading 4 mmol/g) (200-400 mesh) (0.020 molNovabiochem) was added, then a mixture of carbonochloridic acid ethyl ester (0.006 mol) in CH$_2$Cl$_2$ (20 ml) was added dropwise at room temperature and the reaction mixture was stirred over the weekend at room temperature. The mixture was filtered over a glass filter and the scavenger was rinsed with CH$_2$Cl$_2$/CH$_3$OH (30 ml; 80/20). 3-chlorobenzenecarboperoxoic acid (0.015 mol; 70%) was added to the filtrate and the resulting mixture was stirred overnight. Extra 3-chlorobenzenecarboperoxoic acid (1 g) was added and the mixture was stirred for another 8 hours, then (polystyrylmethyl)trimethylammonium bicarbonate scavenger (0.045 mol; loading: 3.7 mmol/g; 20-50 mesh; Novabiochem) was added and the reaction mixture was stirred overnight at room temperature. The scavenger was filtered off and the filtrate was evaporated, yielding intermediate 40.

d. Preparation of Intermediate 6a

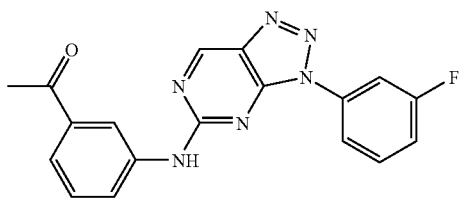

A mixture of intermediate 6 (0.001 mol) and 1-(3-aminophenyl)ethanone (0.002 mol) in 2-methoxyethanol (10 ml) was stirred and refluxed for 16 hours and the solution was cooled. The resulting precipitate was filtered off, rinsed with EtOH/DIPE and dried. Yield: 0.250 g intermediate 6a (72%, m.p. 220-224° C.). The filtrate was evaporated and the residue was stirred in $CH_3CN/CH_3OH$ (2 ml/2 ml). The mixture was stirred for a while, then the precipitate was filtered off and dried. Yield: 0.098 g of intermediate 6a (28%).

e-1. Preparation of Intermediate 6b

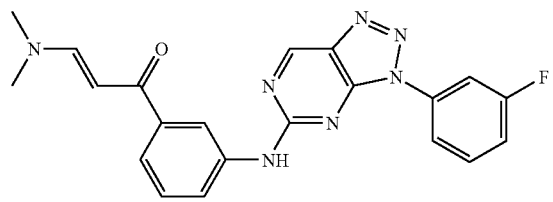

DMF/DMA (0.00675 mol, 5 equiv.) was added to a suspension of intermediate 6a (0.00135 mol, 1 equiv.) in DMF (3 ml) and the reaction mixture was heated at 115° C. for 2 hours, then stirred overnight at room temperature. The resulting precipitate was filtered off and the residue was triturated under diethyl ether on the funnel. Yield 0.38 g of intermediate 6b (70%; 240-244° C.).

e-2. Preparation of Intermediate 6b and Intermediate 6c

Intermediate 6b

Intermediate 6c

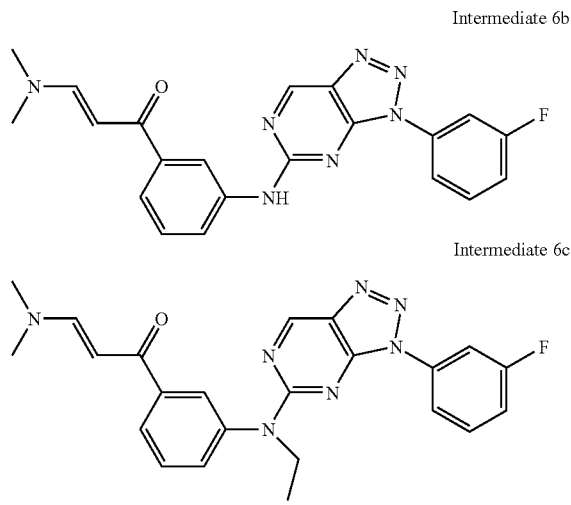

A mixture of intermediate 6a (0.0056 mol, 1 equiv.) in neat DMF/diethylamine (6 ml) was heated overnight at 110-120° C., then EtOH was distilled off and extra DMF/diethylamine (2 ml) was added. The resulting suspension was heated at 120-130° C. for 5 hours, then DMF (2 ml) and extra DMF/diethylamine (1 ml) were added. The reaction mixture was heated at 140° C. for 2 hours, extra DMF (1 ml) was added and the heating was continued. The resulting solution was stirred and refluxed for 1 hour and then stirred overnight at room temperature. The obtained precipitate was filtered off and triturated on the funnel with $Et_2O$ and hexane. Yield 0.38 g of intermediate 6b (17%, m.p.: 235-236° C.). The mother layer was concentrated and the residue was collected. Yield: 1.12 g of intermediate 6c (50%, m.p. 176-179° C.).

EXAMPLE A3 a. Preparation of Intermediate 7

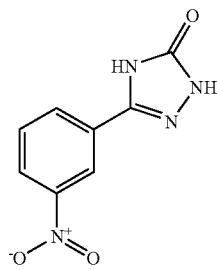

3-Nitrobenzonitrile (0.12 mol) was suspended in EtOH, p.a. (250 ml). NaOEt (0.1 g) was added in one portion and the reaction mixture was stirred overnight.

Hydrazinecarboxylic acid methyl ester (0.36 mol) was added in one portion and the reaction mixture was stirred and refluxed overnight. The reaction mixture was concentrated and redissolved in DMF (150 ml) and heated at 140° C. over the weekend. The reaction mixture was concentrated (vacuum) and the residue was suspended in $H_2O$ (500 ml) and filtered. The resulting residue was again suspended in $H_2O$/EtOH (±2000 ml) and this suspension was heated at refluxed overnight. The hot solution was filtered into an ice-cold erlenmeyer and the solution was stirred for 2 hours. The precipitate was filtered and dried in a vacuum oven (60° C.). Yield: 11.84 g of intermediate 7 (45.9%).

b. Preparation of Intermediate 8

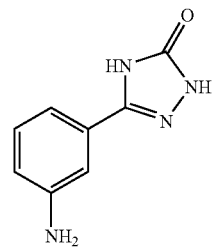

A mixture of intermediate 7 (10 g; 0.048 mol) in MeOH (150 ml) and THF (100 ml) was hydrogenated at 50° C. with Pd/C 10% (1 g) as a catalyst in the presence of a solution of thiophene in DIPE (4%, 1 ml). After uptake of $H_2$ (3 equiv.), the catalyst was filtered off and the filtrate was concentrated. This fraction was suspended in acetone, filtered and dried (vacuum 60° C.). Yield: 7.06g of intermediate 8 (83.5%).

4-(3-amino-phenyl)-pyrimidin-2-ylamine was prepared in an analogous manner: A solution of 4-(3-nitro-phenyl)-pyrimidin-2-ylamine (0.046 mol) in MeOH (250 ml) was hydrogenated at 50° C. with Pd/C 10% (2 g) as a catalyst in the presence of a solution of thiophene in DIPE (4% v/v, 1 ml). After uptake of $H_2$ (3 equiv.), the catalyst was filtered off and the filtrate was concentrated and dried (vacuum 60° C.). Yield: 8.64g of 4-(3-amino-phenyl)-pyrimidin-2-ylamine (87%) (m.p.; 190-194° C.).

EXAMPLE A4 a. Preparation of Intermediate 9

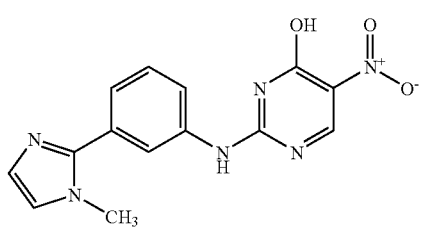

A mixture of 2-chloro-5-nitro-4(1H)-pyrimidinone sodium salt (0.051 mol), 3-(1-methyl-1H-imidazol-2-yl)benzenamine (0.056 mol) and N-ethyl-N-(1-methylethyl)-2-propanamine (0.168 mol) in $H_2O$ (200 ml) and THF (100 ml) was stirred and refluxed for 1 day, then the reaction mixture was cooled to room temperature and the solvent was evaporated under reduced pressure. The residue was stirred in $CH_3OH$ and the resulting precipitate was filtered off, washed with $CH_3OH$ and then dried (vacuum). Yield: 13.6 g of intermediate 9 (85%).

b. Preparation of Intermediate 10

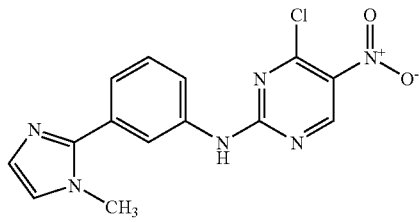

A suspension of intermediate 9 (0.0256 mol) in 6N HCl/2-propanol was stirred at room temperature for 1 hour and then the solvent was evaporated under reduced pressure. $POCl_3$ (100 ml) was added to the residue and the reaction mixture was stirred and refluxed for 1 hour, then stirred at room temperature for 1 hour. The solvent was evaporated under reduced pressure and then co-evaporated with toluene. Quantitative yield of intermediate 10.

c. Preparation of Intermediate 11

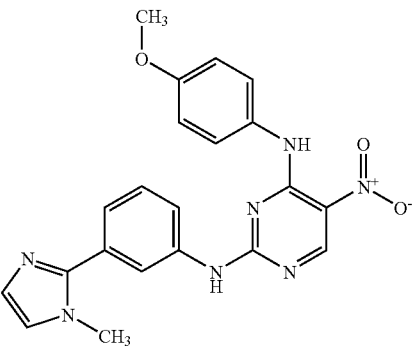

A mixture of intermediate 10 (0.000502 mol), 4-methoxybenzenamine (0.000624 mol) and N-ethyl-N-(1-methylethyl)-2-propanamine (0.000624 mol) in DMA (5 ml) was stirred at 100° C. for 1 hour and the reaction mixture was used as such in the next reaction step.

d. Preparation of Intermediate 12

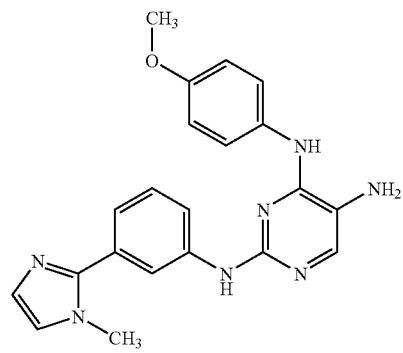

A mixture of intermediate 11 (0.000502 mol) in DMA (q.s.) was hydrogenated overnight with Pt/C (cat.quant.) as a catalyst. After uptake of $H_2$ (3 equiv.), the catalyst was filtered off and the filtrate was evaporated. Yield: intermediate 12.

EXAMPLE A5 a. Preparation of Intermediate 13

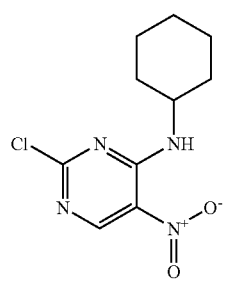

A solution of cyclohexanamine (0.062 mol) in DMA (20 ml) was added dropwise to a cooled (−10° C.) solution of 2,4-dichloro-5-nitropyrimidine (0.062 mol) and N-ethyl-N-(1-methylethyl)-2-propanamine (8.1 g) in DMA (80 ml), then the reaction mixture was allowed to reach room temperature overnight. Yield: intermediate 13 used as such in the next reaction step.

b. Preparation of Intermediate 14

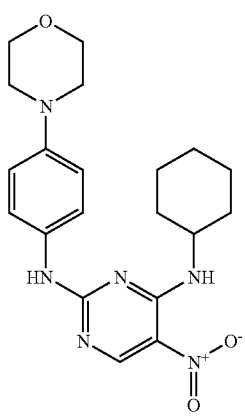

N-ethyl-N-(1-methylethyl)-2-propanamine (0.027 mol) was added to intermediate 13 (0.0257), giving mixture (I). A mixture of 4-(4-morpholinyl)benzenamine (0.0257 mol) in DMA (25 ml, p.a.) was added dropwise at 80° C. to mixture (I) and the reaction mixture was stirred overnight, then poured out into ice-water (500 ml). The resulting solids were filtered off and dried in a vacuum oven at 75° C. This fraction was heated at reflux temperature in 2-propanol/2-propanol (6N HCl) and cooled, then the product was filtered off and dried. Yield: 9.6 g of intermediate 14.

EXAMPLE A5a a. Preparation of Intermediate 41

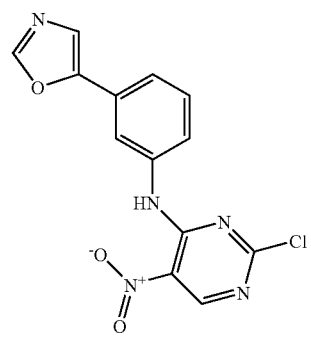

A mixture of 2,4-dichloro-5-nitropyrimidine (5 mmol) in $CH_2Cl_2$ (20 ml) was stirred at −30° C./−40° C. Alternately, a solution of 3-(5-oxazolyl)-benzenamine (5 mmol) in $CH_2Cl_2$ (10 ml) and a solution of N,N-diethylbenzenamine (5 mmol) in $CH_2Cl_2$ (10 ml) were added dropwise over a period of 1 hour, followed by stirring for 2 hours at −20° C./−30° C. The mixture was allowed to come to room temperature while stirring. The mixture was diluted with 50 ml of $CH_2Cl_2$ and 50 ml of ice water was added. The precipitate was filtered and dried. Yield: 490 mg of intermediate 41. Of the filtrate, the layers were separated and the organic layer was dried, filtered and evaporated. The residue was stirred in $CH_3CN$. The precipitate was filtered off and dried. Yield: 305 mg of intermediate 41.

b. Preparation of Intermediate 42

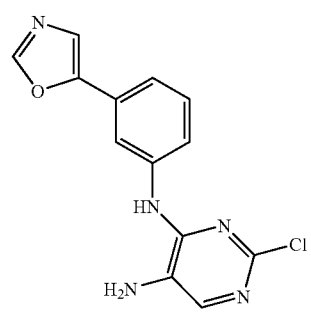

A mixture of intermediate 41 (1 mmol) in THF (50 ml) was hydrogenated with Pt/C 5% (0.2 g) as a catalyst in the presence of a solution of thiophene in DIPE (4% v/v, 0.5 ml) and in the presence of triethylamine (equimolar). After uptake of $H_2$, the catalyst was filtered off and the filtrate was evaporated. Yield: 300 mg of intermediate 42.

c. Preparation of Intermediate 43

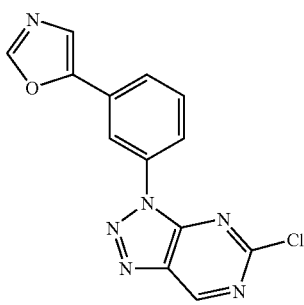

A mixture of intermediate 42 (prepared according to A2b.b) (0.001 mol) and HCl 1N (0.002 mol) in acetic acid (20 ml) was stirred at room temperature, then a mixture of NaNO$_2$ (0.001 mol) in H$_2$O (2 ml) was added dropwise and the reaction mixture was stirred overnight at room temperature. The solvent was evaporated and the residue was stirred in CH$_3$CN. The resulting precipitate was filtered off and dried. Yield: 0.190 g of intermediate 43.

EXAMPLE A6 a. Preparation of Intermediate 15

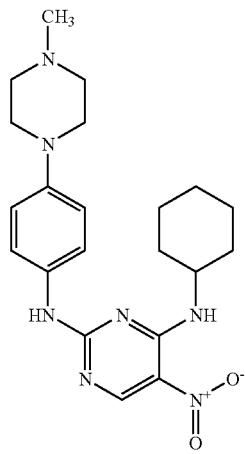

A mixture of intermediate 13 (prepared according to A5.a) (0.031 mol), 4-(4-methyl-1-piperazinyl)benzenamine hydrochloride (0.031 mol) and N-ethyl-N-(1-methylethyl)-2-propanamine (10 g) was heated at 60° C. for 3 hours, then the reaction mixture was cooled and added dropwise to H$_2$O (200 ml). The resulting solids were filtered off and dried in a vacuum oven at 60° C. Yield: 9.6 g of intermediate 15.

b. Preparation of Intermediate 16

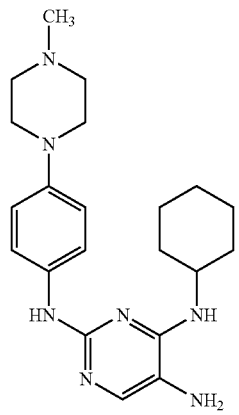

A mixture of intermediate 15 (0.023 mol) and Et$_3$N (10 ml) in THF (250 ml) was hydrogenated at 50° C. with Pd/C 10% (2 g) as a catalyst in the presence of a solution of thiophene in DIPE (4%, 1 ml). After uptake of H$_2$ (3 equivalents), the catalyst was filtered off and the filtrate was evaporated. The residue was dissolved in CH$_2$Cl$_2$, washed with H$_2$O and dried. Yield: 6.7 g of intermediate 16 (76.5%).

EXAMPLE A7

Preparation of Intermediate 17

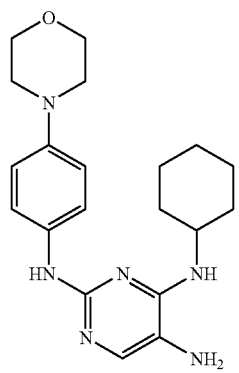

A mixture of intermediate 14 (prepared according to A5.b) (0.024 mol) in CH$_3$OH (250 ml) was hydrogenated with Pt/C 5% (2 g) as a catalyst in the presence of a solution of thiophene in DIPE (4%, 1 ml). After uptake of H$_2$ (3 equivalents), the catalyst was lo filtered off and the filtrate was evaporated. Yield: 8.7 g intermediate 17.

EXAMPLE A8

Preparation of Intermediate 18

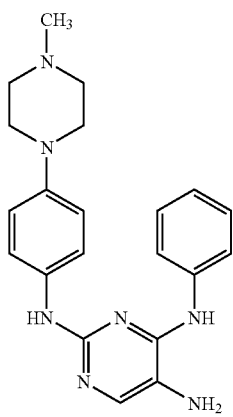

A mixture of intermediate

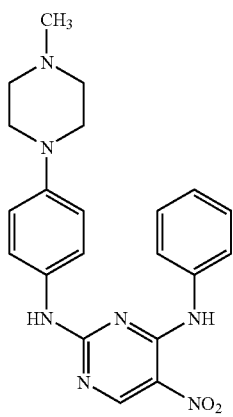

(prepared according to A6.a) (0.007 mol) in THF (150 ml) was hydrogenated at 50° C. with Pd/C 10% (1 g) as a catalyst in the presence of a solution of thiophene in DIPE (4%, 1 ml). After uptake of $H_2$ (3 equivalents), the catalyst was filtered off and the filtrate was evaporated. 2-propanol/HCl (6N) was added to the residue and the mixture was stirred for 1 hour. The resulting precipitate was filtered off and dried in a vacuum oven at 60° C. Yield: 3 g of intermediate 18.

EXAMPLE A9 a. Preparation of Intermediate 19

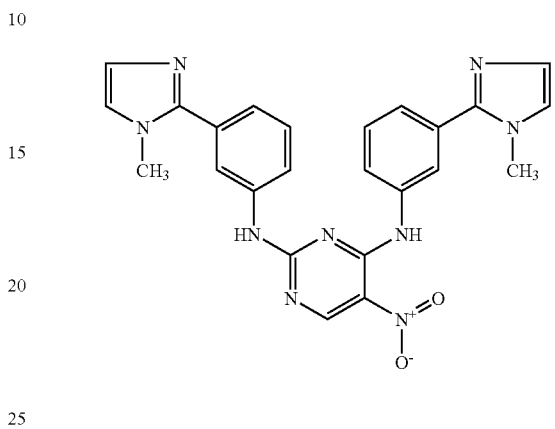

A mixture of 2,4-dichloro-5-nitropyrimidine (0.0127 mol), 3-(1-methyl-1H-imidazol-2-yl)benzenamine (0.0254 mol) and DIPEA (0.0254 mol) in DMF (60 ml) was stirred overnight at 60° C. The reaction mixture was used as such in the next step.

b. Preparation of Intermediate 20

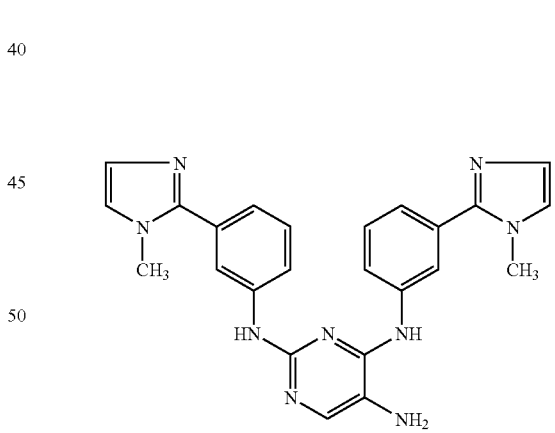

Intermediate 19 (0.0127 mol) in DMF (100 ml) was hydrogenated at room temperature with Pd/C 10% (2g) as a catalyst in the presence of a solution of thiophene in DIPE (4%, 2 ml). After uptake of $H_2$ (3 equivalents), the catalyst was filtered off and the solvent was evaporated. Yield: intermediate 20. This fraction was used as such in further step.

EXAMPLE A10

Preparation of Intermediate 29

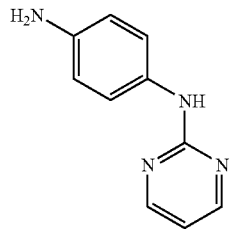

A mixture of 1,4-diaminobenzene (54 g, 0.50 mol), 2-chloropyrimidine (28 g, 0.25 mol), calcium oxide (30 g, 0.53 mol), and THF (400 ml) were heated to 200° C. for 12 hours in an autoclave. After cooling the mixture was filtered and the solvent removed by rotary evaporation. The residue was chromatographed on a silica gel plug using dichloromethane as eluent, to give an oil which crystallised upon standing for 24 hours. Yield: 14 g of intermediate 29 (30%).

EXAMPLE A11 a. Preparation of Intermediate 35

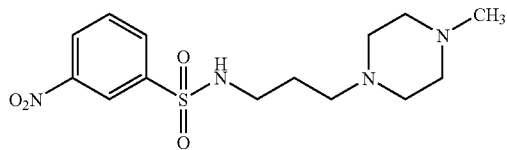

NaHCO$_3$ (0.078 mol) and 4-methyl-1-piperazinepropanamine (0.078 mol) were dissolved in H$_2$O (120 ml) and 2-propanone (80 ml) and the resulting solution was cooled on an ice bath, then a solution of 3-nitrobenzenesulfonyl chloride (0.078 mol) in 2-propanone (160 ml) was added dropwise and the reaction mixture was stirred for 1 hour at room temperature. The 2-propanone was evaporated and the oily residue was extracted 3 times with EtOAc. The organic extracts were combined and washed with a NaHCO$_3$ solution and with H$_2$O/Brine, then dried (MgSO$_4$), filtered and the solvent was evaporated. The dry residue was triturated with hot Et$_2$O under reflux and then the desired product was filtered and rinsed with Et$_2$O. Yield: 17.9 g of intermediate 35 (67.0%). (A second fraction was obtained by evaporation after the trituration, to give 0.8 g of intermediate 35 (3%). (Overall Yield: 70%).

b. Preparation of Intermediate 36

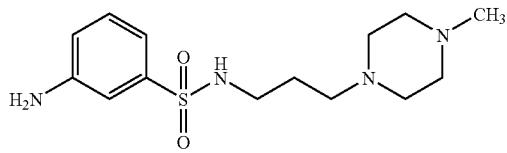

A solution of intermediate 35 (prepared according to A11.a) (0.052 mol) in methanol (500 ml) was hydrogenated at room temperature with Pd/C 5% (2.0 g) as a catalyst. After uptake of H$_2$ (3 equivalents), the reaction mixture was filtered over celite and the solvent was evaporated. The oily residue was left to stand and the resulting solid was triturated under Et$_2$O and then the desired product was collected by filtration. Yield: 15.57 g of intermediate 36 (95.8%, m.p.: 141-143° C.).

b. Preparation of the Final Compounds

EXAMPLE B1 a-1. Preparation of Compound 1

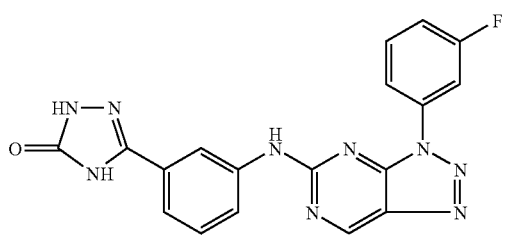

A mixture of intermediate 6 (prepared according to A2.c-1) (0.0002 mol) and intermediate 8 (prepared according to A3.b) (0.0004 mol) in DMSO, p.a. (1 ml) was stirred for 2 hours at 100° C., the reaction mixture was diluted with CH$_3$CN (1 ml) and stirred overnight. The resulting precipitate was filtered off and dried. Yield: 0.061 g of compound 1 (78%, m.p.: >260° C.).

a-2. Preparation of Compound 43

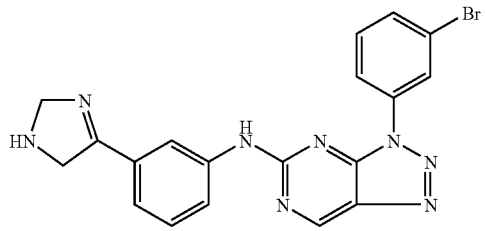

A mixture of intermediate 21

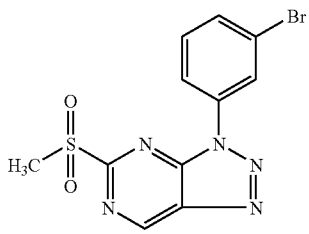

(prepared according to A2.c-1) (0.0002 mol) and 3-(1H-imidazol-2-yl)-benzenamine (0.00022 mol) in DMSO, p.a (1 ml) was stirred for 2 hours at 100° C., then H$_2$O (2 ml) and CH$_3$CN (3 ml) were added, finally HCl/2-propanol was added until the mixture was acidic. The resulting precipitate was filtered off and dried. Yield: 0.029 g of final compound 43 (31%; m.p.: >260° C.)

a-3. Preparation of Compound 51

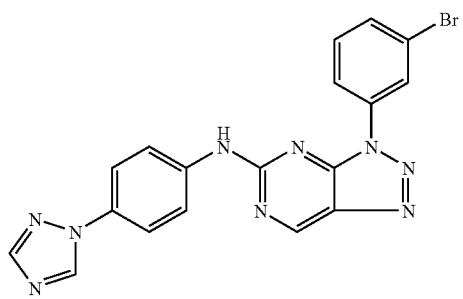

A mixture of intermediate 21 (prepared according to A2.c-1) (0.00014 mol) and 4-(1H-1,2,4-triazol-1-yl)-benzenamine (0.00016 mol) in DMSO (0.5 ml) was reacted for 3 hours in a shaker at 100° C., then the reaction mixture was shaken at 110° C. Finally, the mixture was reacted in a microwave at 150° C. The resulting precipitate was filtered off and dried (vacuum). Yield: 0.0096 g of final compound 51.

a-4. Preparation of Compound 30

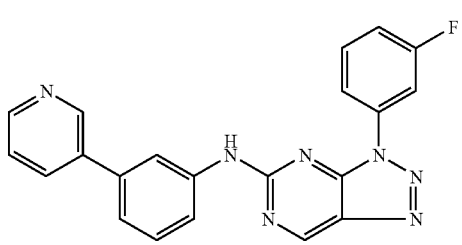

A mixture of intermediate 6 (prepared according to A2.c-1) (0.0003 mol) and 3-(3-pyridinyl)-benzenamine, (0.0006 mol) in DMSO, p.a. (1 ml) was stirred for 3 hours at 100° C. and then the reaction mixture was cooled and purified by preparative high-performance liquid chromatography. The product fractions were collected and the solvent was evaporated. The residue was stirred in $H_2O/CH_3OH$ (2 ml/2 ml); the resulting precipitate was filtered off and dried. Yield: 0.020 g of final compound 30 (m.p.: 208-212° C.).

a-5. Preparation of Compound 80

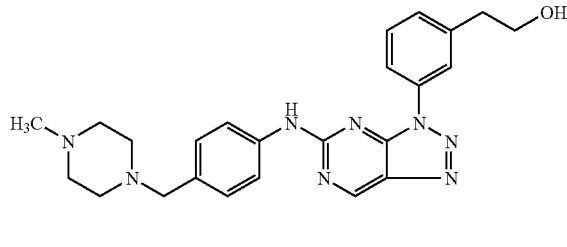

A mixture of intermediate 30

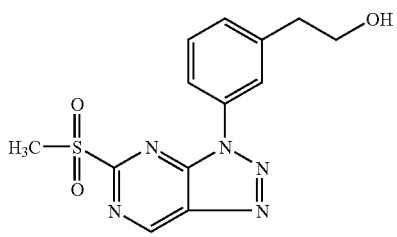

(prepared according to A2.C-2) (0.0002 mol) and 4-[(4-methyl-1-piperazinyl)methyl]-benzenamine (0.0004 mol) in DMSO (2 ml) was stirred for 3 hours at 80° C. and then the reaction mixture was stirred overnight at room temperature. The solvent was evaporated (Genevac) and the obtained residue was purified by high-performance liquid chromatography. The product fractions were collected, then the solvent was evaporated and. co-evaporated with $CH_3OH$. Yield: 0.0119 g of final compound 80.

b-1. Preparation of Compound 2

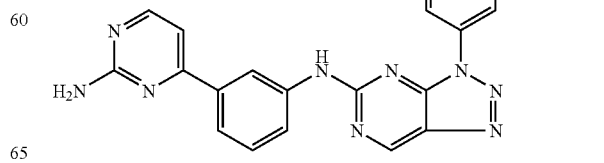

A mixture of intermediate 6 (prepared according to A2.c-1) (0.0005 mol) and 3-pyrazin-2-ylbenzenamine (0.0005 mol) in 2-methoxyethanol (4 ml) was stirred at 100° C. for 30 minutes, then the reaction mixture was allowed to reach room temperature. The resulting precipitate was filtered off and dried. Yield: 0.082 g of compound 2 (m.p.: >260° C.).

b-2. Preparation of compound 87

A mixture of intermediate 32 (prepared according to A2.c-5) (0.0002 mol) and intermediate 33

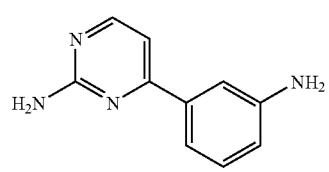

(prepared according to A3.b) (0.0002 mol) in 2-methoxyethanol (1 ml) was stirred for 2 hours at 80° C. and then the reaction mixture was allowed to cool overnight. The mixture was diluted with $CH_3OH$ (1 ml), then the resulting precipitate was filtered off and dried. Yield: 0.037 g of final compound 87 (44%, m.p.: >260° C.).

b-3. Preparation of Compound 36

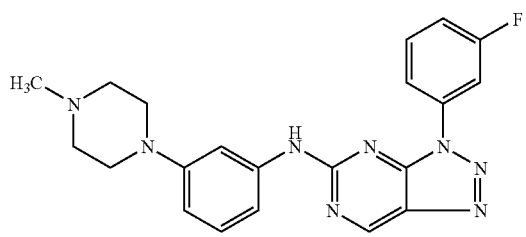

A mixture of intermediate 6 (prepared according to A2.c-1) (0.0005 mol) and 3-(4-methyl-1-piperazinyl)-benzenamine (0.0005 mol) in 2-methoxyethanol (4 ml) was stirred for 1 hour at 100° C. and the solvent was evaporated. The residue was stirred in DIPE and then the DIPE was decanted off. The residue was dissolved in $CH_3OH$, warmed and acidified with HCl/2-propanol. The resulting precipitate was filtered off and dried. Yield: 0.123 g of final compound 36 (51.5%; m.p.: >250° C.).

b-4. Preparation of Compound 115

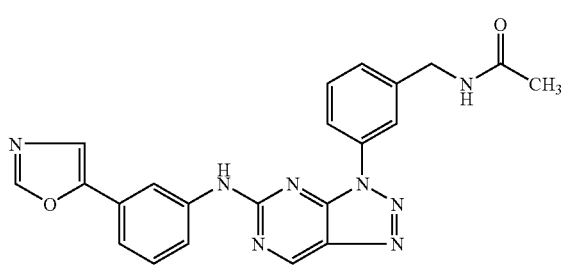

A mixture of intermediate 25 (prepared according to A2.c-3) (0.0005 mol) and 3-(5-oxazolyl)benzenamine (0.0005 mol) in 2-methoxyethanol (2.5 ml) was stirred for 4 hours at 100° C. and the solvent was evaporated. The residue was crystallised from $CH_3CN/CH_3OH$ (4 ml/1 ml), then the precipitate was filtered off and dried. Yield: 0.171 g of fraction 1. This fraction was further crystallised from 2-methoxyethanol (92 ml) and $CH_3CN$ (4 ml) and the resulting mixture was stirred overnight. The precipitate was filtered off and dried. Yield: 0.103 g of final compound 115 (48%, m.p.: 156-160° C.).

b-5. Preparation of Compound 122

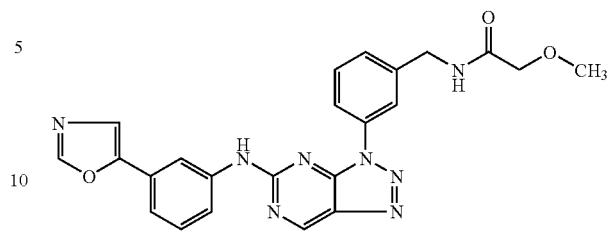

A mixture of intermediate 28 (prepared according to A2.c-4b) (0.0001 mol) and 3-(5-oxazolyl)benzenamine (0.0001 mol) in 2-methoxyethanol (1 ml) was stirred for 48 hours at 100° C. and then the solvent was evaporated. The residue was purified on RediSep (eluent: $CR_2Cl_2/CH_3OH$ 100/0→98/2). The product fractions were collected and the solvent was evaporated. The residue was crystallised from $CR_3OH$ with 1 drop of $H_2O$, then the resulting precipitate was filtered off and dried. Yield: 0.017 g final compound 122 (37%, m.p. (Kofler): 210-214° C.)

b-6. Preparation of Compound 88

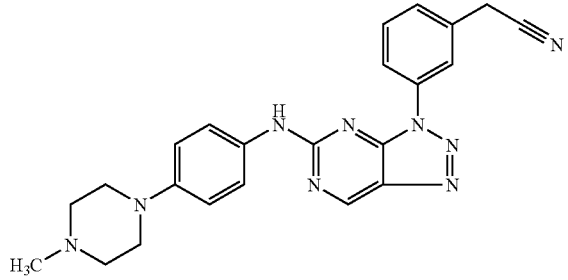

A mixture of intermediate 32

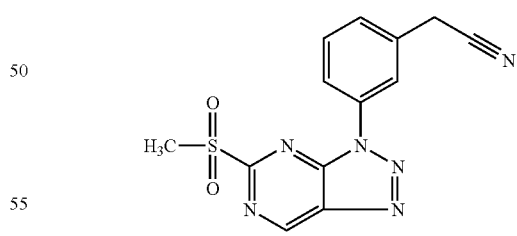

(prepared according to A2.c-5) (0.0003 mol), 4-(4-methyl-1-piperazinyl)benzenamine dihydrochloride (0.0003 mol) and N-ethyl-N-(1-methylethyl)-2-propanamine (0.0006 mol) in 2-methoxyethanol (3 ml) was stirred for 2 hours at 80° C., then the reaction mixture was allowed to cool and the solvent was evaporated. The obtained residue was stirred in boiling $CH_3CN$ and the mixture was stirred overnight. The resulting precipitate was filtered off and dried. Yield: 0.096 g of final compound 88 (75%, m.p.: 210-212° C.).

b-7. Preparation of Compound 125

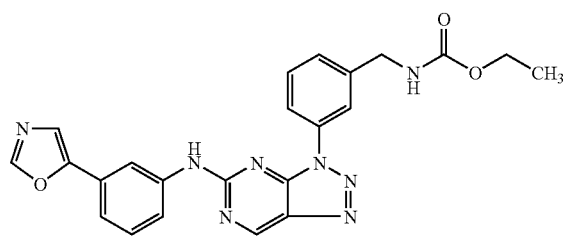

A mixture of intermediate 40 (prepared according to A2.c-6) (0.0002 mol) and 3-(5-oxazolyl)benzenamine (0.0004 mol) in 2-methoxyethanol (2 ml) was stirred for 20 hours at 120° C. and then the crude mixture was purified by high-performance liquid chromatography. The pure product fractions were collected and the solvent was evaporated. The obtained residue was dissolved in $CH_3OH$ and then the solvent was evaporated. Yield: 0.006 g of final compound 125.

b-8. Preparation of Compound 154

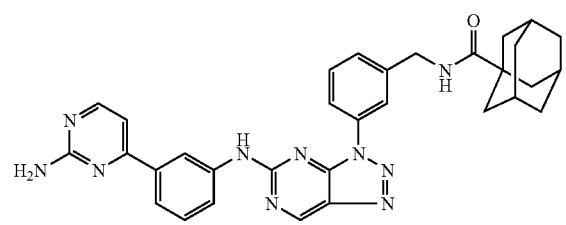

A mixture of intermediate 37

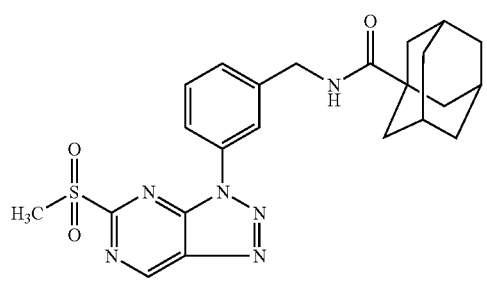

(prepared according to A2.c-6) (0.0002 mol) and intermediate 33 (prepared according to A2.a) (0.0004 mol) in 2-methoxyethanol (2 ml) was stirred for at least 48 hours at 120° C. and then the crude mixture was purified by high-performance liquid chromatography. The product fractions were collected and the solvent was evaporated. The obtained residue was dissolved in EtOH and then the solvent was evaporated. Yield: 0.017 g of final compound 154.

EXAMPLE B2 a. Preparation of Compound 3

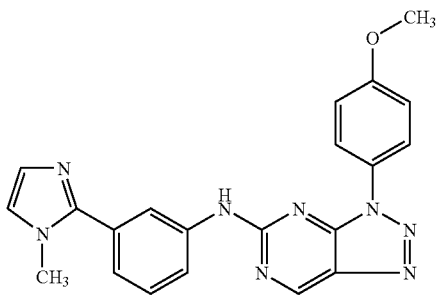

A mixture of intermediate 12 (prepared according to A4.d) (0.000502 mol), $H_2O$ and HCl (6N) was stirred at 0° C. for 20 minutes, then $NaNO_2$ was added in one portion and the reaction mixture was stirred at room temperature for 48 hours. Yield: compound 3.

b-1. Preparation of Compound 4

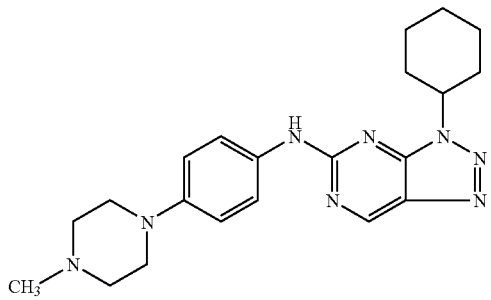

A mixture of $NaNO_2$ (0.00797 mol) in $H_2O$ (q.s.) was added dropwise to an ice cooled mixture of intermediate 16 (prepared according to A6.b) (0.00786 mol) in HCl, 6N (30 ml) and $H_2O$ (q.s.) and the reaction mixture was allowed to reach room temperature, then the mixture was poured out into a saturated $NaHCO_3$ solution and extracted with $CH_2Cl_2$ (3 times 200 ml). The organic layers were combined, dried ($MgSO_4$) and the solvent was evaporated. The residue was purified by reversed phase chromatography, then the product fractions were collected and the solvent was evaporated. Yield: 0.733 g of compound 4 (24%, m.p.: 167° C.).

b-2. Preparation of Compound 96

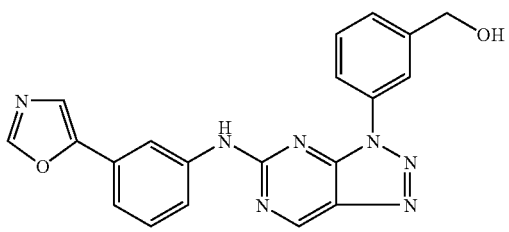

A mixture of intermediate 39

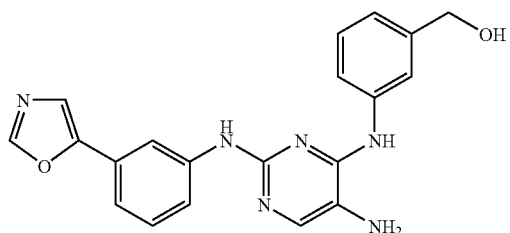

(prepared according to A7/A8) (0.0006 mol) in acetic acid (8 ml) and HCl 1N (2 ml) was stirred at room temperature, then a mixture of NaNO₂ (0.00066 mol) in H₂O, demineralised (1 ml) was added dropwise to the solution (precipitation) and the reaction mixture was stirred for 1 hour. The resulting precipitate was filtered off, rinsed with CH₃CN and dried (vacuum). Yield: 0.096 g of final compound 96 (41%, m.p.: 210-214° C.)

c. Preparation of Compound 5 and 6 compound 5

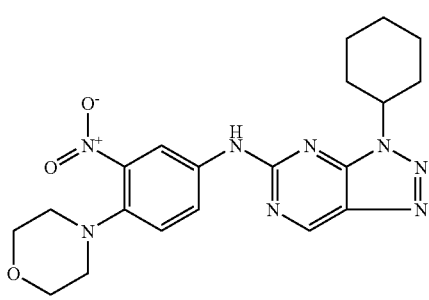

compound 6

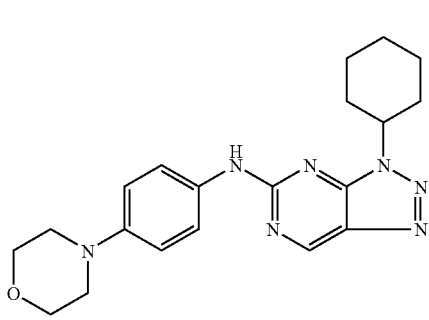

A solution of intermediate 17 (prepared according to A7) (0.0038 mol) in H₂O (100 ml) and HCl, concentrated (5 ml) was cooled and a mixture of NaNO₂ (0.0038 mol) in H₂O (5 ml) was slowly added dropwise, then the reaction mixture was stirred overnight at room temperature and CH₂Cl₂ (75 ml) was added. The pH of the aqueous layer was adjusted to pH 9 and extracted with CH₂Cl₂ (3 times 75 ml). The organic layers were combined, dried (MgSO₄), filtered off and the solvent was evaporated (vacuum). The residue was purified by reversed phase chromatography, then two product fractions were collected and the solvent was evaporated. Yield fraction 1: 0.100 g of compound 5 (m.p.: 161.9° C.). Yield fraction 2: 0.0106 g of compound 6.

EXAMPLE B3

Preparation of Compound 7

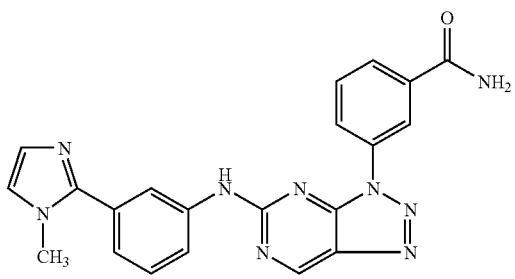

A solution of intermediate 20 (prepared according to A9.b) (0.0127 mol) in CH₃COOH (30 ml) and 6N HCl (50 ml) was stirred at 0° C. A solution of NaNO₂ (0.015 mol) in H₂O (10 ml) was added dropwise and the resulting reaction mixture was stirred for one hour at 0° C., then overnight at room temperature. The solvent was evaporated under reduced pressure. The residue was purified by HPLC over Hyperprep C18 (HS, BDS, 100 Å, 8 μm, Shandon; eluent: [(0.5% NH₄OAc in H₂O)/CH₃CN 90/10 vol %]/CH₃OH/CH₃CN (0 minutes) 75/25/0, (24 minutes) 38/37/25, (24.01-32 minutes) 0/0/100). The product fractions were collected and the solvent was evaporated. The residue was stirred in DIPE, filtered off, washed and dried (vacuum, 50° C.). Yield: 0.160 g of compound 7.

EXAMPLE B4 a. Preparation of Compound 35

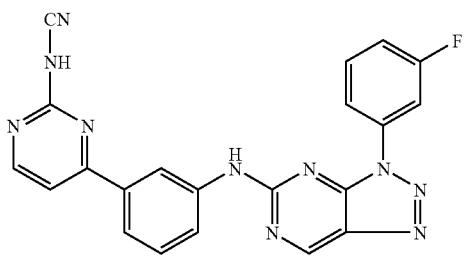

Intermediate 6b (0.00015 mol, 1 equiv.) was added to a solution of cyanoguanidine (0.00045 mol, 3 equiv.) in 2-ethoxyethanol (2 ml) and the mixture was stirred and refluxed for 2 hours, then stirred overnight at room temperature. CH₃ONa (0.00015 mol, 1 equiv.) and the resulting mixture was stirred and refluxed for 1 hour. Extra cyanoguanidine (0.00045 mol, 3 equiv.) and extra CH₃ONa (0.00045 mol, 3 equiv.) were added and then the reaction mixture was stirred and refluxed for 3 hours. The mixture was cooled and poured out into ice-water. The resulting precipitate was filtered off, washed with H₂O and dried (P₂O₅). Yield: 0.060 g of compound 35 (94%)

b. Preparation of Compound 34

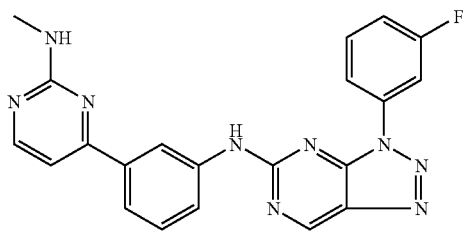

Methylguanidine (0.00075 mol, 3 equiv.) was added to a solution of CH$_3$ONa (0.00075 mol, 3 equiv.) in 2-ethoxyethanol (2 ml) and the resulting mixture was stirred for 30 minutes, then a suspension of intermediate 6b (prepared according to A2.e-1) (0.00025 mol, 1 equiv.) in 2-ethoxyethanol (1 ml) was added and the reaction mixture was stirred and refluxed for 4 hours. The mixture was cooled and poured out into ice-water. The resulting precipitate was filtered off, washed with H$_2$O and dried under vacuum and P$_2$O$_5$. Yield: 0.085 g of compound 34 (82%).

c. Preparation of Compound 70

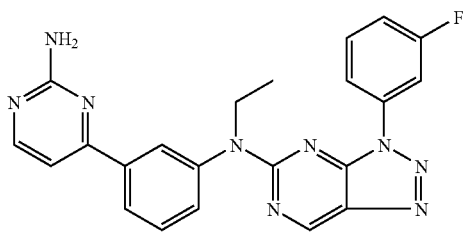

Guanidine (0.00075 mol, 3 equiv.) was added to a solution of CH$_3$ONa (0.00075 mol, 3 equiv.) in 2-ethoxyethanol (2 ml) and the resulting mixture was stirred for 30 minutes, then a suspension of intermediate 6c (prepared according to A2.e-2) (0.00023 mol, 1 equiv.) in 2-ethoxyethanol (3 ml) was added and the reaction mixture was stirred and refluxed for 2 hours. The mixture was cooled and poured out into ice-water. The resulting precipitate was filtered off, washed with H$_2$O and dried under vacuum and P$_2$O$_5$. Yield: 0.080 g of compound 70 (81%).

d. Preparation of Compound 69

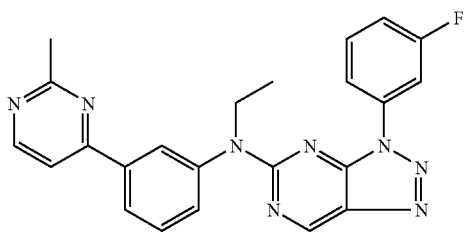

Acetamidine HCl (0.00115 mol, 5 equiv.) was added to a solution of CH$_3$ONa (0.00115 mol, 5 equiv.) in 2-ethoxyethanol (q.s.) and the resulting mixture was stirred for 15 minutes, then intermediate 6c (prepared according to A2.e-2) (0.00023 mol, 1 equiv.) was added. The reaction mixture was heated at 130-135° C. for 4 hours and stirred overnight at room temperature. A solution of acetamidine HCl (0.00069 mol, 3 equiv.) and CH$_3$ONa (0.00069 mol, 3 equiv.) in 2-ethoxyethanol (q.s.) was added and the reaction mixture was stirred and refluxed for 3 hours, then stirred overnight at 50° C. Extra acetamidine HCl (0.00115 mol, 5 equiv.) and extra CH$_3$ONa (0.00115 mol, 5 equiv.) were added, then the resulting reaction mixture was stirred and refluxed for 5 hours. Ice-cold water was added and the resulting precipitate was filtered off, then washed with H$_2$O. The solids were rinsed on the funnel with diethyl ether and were dissolved in 2-propanone. The solvent was evaporated to dryness and the residue was dissolved in 2-propanone. H$_2$O was added and the solvent was co-evaporated with CH$_3$CN, then the residue was dried (P$_2$O$_5$). Yield: 0.090 g of compound 69 (91%).

e. Preparation of Compound 22

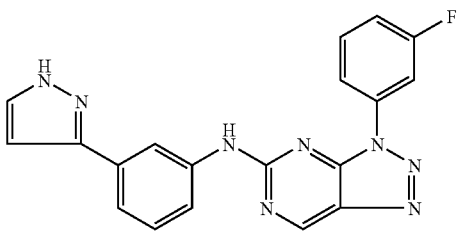

Intermediate 6b (prepared according to A2.e-1/A2.e-2) (0.00015 mol, 1 equiv.) was added to a solution of hydrazine, anhydrous (0.030 g) in 2-ethoxyethanol (2 ml) and the reaction mixture was stirred and refluxed for 30 minutes. The solution was cooled and poured out into ice-water. The resulting precipitate was filtered off and washed on the funnel with H$_2$O. The residue was triturated on the funnel under Et$_2$O and then dried in. vacuum under P$_2$O$_5$. Yield: 0.035 g of compound 22 (63%).

EXAMPLE B5

Preparation of Compound 9

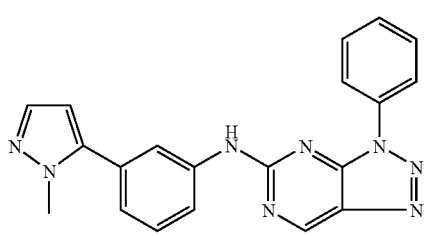

A mixture of

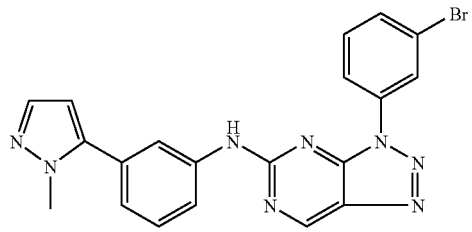

compound 8 (prepared according to B1.a-2) (0.00016 mol) and Et₃N (0.5 ml) in THF (40 ml) was hydrogenated with Pd/C 10% (0.02 g) as a catalyst in the presence of a solution of thiophene in DIPE (4% v/v, 0.01 ml). After uptake of H₂ (1 equiv.), the catalyst was filtered off and the filtrate was evaporated. The residue was crystallised from CH₃CN, the resulting precipitate was filtered off and dried. Yield: 0.029 g of compound 9 (m.p.: 216° C.).

EXAMPLE B6

Preparation of Compound 114

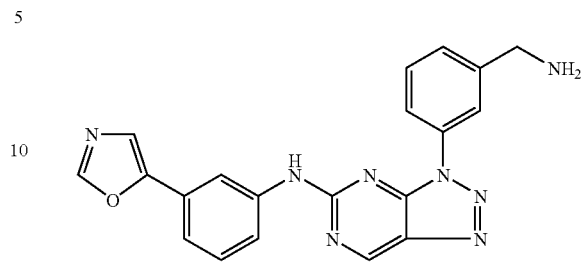

A mixture of final compound 126 (prepared according to B1.b-5) (0.0002 mol) in HCl/2-propanol (6N) (1 ml) and HCl (1N) (4 ml) was stirred for 24 hours at room temperature, then the resulting precipitate was filtered off and dried. Yield: 0.076 g of final compound 114 (77%, m.p.: >250° C.)

Tables 1 to 5 list the compounds of formula (I) which were prepared according to one of the above examples.

TABLE 1

| Co. no. | Ex. no. | X₁ | R² | X₂ | R³ | physical data (m.p. ° C.)/salt |
|---|---|---|---|---|---|---|
| 9 | B5 | db | phenyl | 2-db | 1-methyl-pyrazol-5-yl | 214 |
| 73 | B1b-1 | db | phenyl | 2-db | oxazol-5-yl | 214 |
| 74 | B1b-1 | db | phenyl | 2-db | 1-methyl-tetrazol-5-yl | 248 |
| 151 | B1b-4 | db | phenyl | 2-db | 2-amino-pyrimidin-4-yl | 237 |
| 10 | B5 | db | phenyl | 3-db | 2-methyl-tetrazol-5-yl | 242 |

TABLE 1-continued

| Co. no. | Ex. no. | X₁ | R² | X₂ | R³ | physical data (m.p. ° C.)/salt |
|---|---|---|---|---|---|---|
| 11 | B2a | db | phenyl | 3-db | morpholinyl (N-linked) | |
| 12 | B2a | db | phenyl | 3-db | 4-methylpiperazin-1-yl | 223 |
| 13 | B2a | —CH₂— | phenyl | 2-db | 1-methyl-1H-imidazol-2-yl | |
| 14 | B2a | db | 3-methylphenyl | 2-db | 1-methyl-1H-imidazol-2-yl | |
| 15 | B2a | db | 2-methylphenyl | 2-db | 1-methyl-1H-imidazol-2-yl | |
| 152 | B1b-2 | db | 3-(2-hydroxyethyl)phenyl | 2-db | 4-bromo-1-methyl-1H-pyrazol-3-yl | 137 |
| 75 | B1b-2 | db | 3-(2-hydroxyethyl)phenyl | 2-db | 1H-tetrazol-5-yl | 190 |
| 76 | B1b-2 | db | 3-(2-hydroxyethyl)phenyl | 2-db | 1-methyl-1H-tetrazol-5-yl | 203 |
| 77 | B1b-6 | db | 3-(2-hydroxyethyl)phenyl | 3-db | 4-methylpiperazin-1-yl | 197 |

TABLE 1-continued

| Co. no. | Ex. no. | X₁ | R² | X₂ | R³ | physical data (m.p. ° C.)/salt |
|---|---|---|---|---|---|---|
| 56 | B2a | db | 4-(2-hydroxyethyl)phenyl | 2-db | 1-methylimidazol-2-yl | |
| 85 | B1b-2 | db | 4-(2-hydroxyethyl)phenyl | 3-db | morpholin-4-yl | 203 |
| 86 | B1b-2 | db | 3-(cyanomethyl)phenyl | 2-db | oxazol-5-yl | 190 |
| 87 | B1b-2 | db | 3-(cyanomethyl)phenyl | 2-db | 2-aminopyrimidin-4-yl | >260 |
| 88 | B1b-6 | db | 3-(cyanomethyl)phenyl | 3-db | 4-methylpiperazin-1-yl | 210 |
| 95 | B1b-2 | db | 3-(carbamoylmethyl)phenyl | 2-db | oxazol-5-yl | >260 |
| 96 | B2b-2 | db | 3-(hydroxymethyl)phenyl | 2-db | oxazol-5-yl | 210 |
| 97 | B1b-4 | db | 3-(hydroxymethyl)phenyl | 2-db | 2-aminopyrimidin-4-yl | 240 |

TABLE 1-continued

| Co. no. | Ex. no. | X₁ | R² | X₂ | R³ | physical data (m.p. ° C.)/salt |
|---|---|---|---|---|---|---|
| 98 | B1b-5 | db | 3-(methoxymethyl)phenyl | 2-db | oxazol-5-yl | 136 |
| 99 | B1b-4 | db | 3-(methoxymethyl)phenyl | 2-db | 1-methyl-tetrazol-5-yl | 196 |
| 100 | B1b-5 | db | 3-(methoxymethyl)phenyl | 2-db | 2-aminopyrimidin-4-yl | 232 |
| 107 | B1b-2 | db | 3-((2-methoxyethoxy)methyl)phenyl | 3-db | morpholin-4-yl | 169 |
| 108 | B1b-6 | db | 3-((2-methoxyethoxy)methyl)phenyl | 3-db | 4-methylpiperazin-1-yl | 181 |
| 114 | B6 | db | 3-(aminomethyl)phenyl | 2-db | oxazol-5-yl | >250 HCl |
| 115 | B1b-4 | db | 3-(acetamidomethyl)phenyl | 2-db | oxazol-5-yl | 156 |
| 116 | B1b-2 | db | 3-(acetamidomethyl)phenyl | 2-db | 1-methyl-tetrazol-5-yl | 222 |

TABLE 1-continued

| Co. no. | Ex. no. | X₁ | R² | X₂ | R³ | physical data (m.p. ° C.)/salt |
|---|---|---|---|---|---|---|
| 117 | B1b-1 | db | 3-benzyl-NHC(O)CH₃ | 2-db | 2-aminopyrimidin-4-yl | 244 |
| 118 | B1b-7 | db | 3-benzyl-NHC(O)-cyclopropyl | 2-db | oxazol-5-yl | |
| 119 | B1b-7 | db | 3-benzyl-NHC(O)-cyclopropyl | 2-db | 2-aminopyrimidin-4-yl | |
| 120 | B1b-7 | db | 3-benzyl-NHC(O)CH₂CH(CH₃)₂ | 2-db | oxazol-5-yl | |
| 121 | B1b-7 | db | 3-benzyl-NHC(O)CH₂CH(CH₃)₂ | 2-db | 2-aminopyrimidin-4-yl | |
| 122 | B1b-5 | db | 3-benzyl-NHC(O)CH₂OCH₃ | 2-db | oxazol-5-yl | 210 |
| 123 | B1b-1 | db | 3-benzyl-NHC(O)CH₂OCH₃ | 3-db | oxazol-5-yl | 228 |

TABLE 1-continued

| Co. no. | Ex. no. | X₁ | R² | X₂ | R³ | physical data (m.p. ° C.)/salt |
|---|---|---|---|---|---|---|
| 124 | B1b-2 | db | 3-(benzyl-NH-C(O)-CH₂-O-CH₃) | 3-db | benzoxazol-2-yl | 172 |
| 125 | B1b-5 | db | 3-(benzyl-NH-C(O)-O-CH₂CH₃) | 2-db | oxazol-5-yl |  |
| 126 | B1b-5 | db | 3-(benzyl-NH-C(O)-O-C(CH₃)₃) | 2-db | oxazol-5-yl |  |
| 16 | B1b-4 | db | 3-methoxyphenyl | 2-db | oxazol-5-yl | 186 |
| 17 | B2a | db | 3-methoxyphenyl | 2-db | 1-methylimidazol-2-yl |  |
| 127 | B1b-2 | db | 3-methoxyphenyl | 2-db | 1H-tetrazol-5-yl | 232 |
| 128 | B1b-2 | db | 3-methoxyphenyl | 2-db | 1-methyltetrazol-5-yl | 232 |
| 18 | B1b-2 | db | 3-methoxyphenyl | 2-db | 2-methyltetrazol-5-yl | 240 |

TABLE 1-continued

| Co. no. | Ex. no. | X₁ | R² | X₂ | R³ | physical data (m.p. ° C.)/salt |
|---|---|---|---|---|---|---|
| 19 | B1b-2 | db | 3-methoxyphenyl | 2-db | 2-aminopyrimidin-4-yl | 242 |
| 129 | B1a-3 | db | 3-methoxyphenyl | 2-db | 4-methylpiperazin-1-yl | decomposition at 250° C. HCl |
| 3 | B2a | db | 4-methoxyphenyl | 2-db | 1-methylimidazol-2-yl | |
| 130 | B1b-6 | db | 3-(2-methoxyethoxy)phenyl | 3-db | 4-methylpiperazin-1-yl | 199 |
| 20 | B1b-1/ B1a-1 | db | 3-fluorophenyl | 2-db | oxazol-5-yl | 230 |
| 21 | B1a-1 | db | 3-fluorophenyl | 2-db | 2-methylthiazol-4-yl | 254 |
| 22 | B1a-1 | db | 3-fluorophenyl | 2-db | 1H-pyrazol-3-yl | |
| 149 | B1b-2 | db | 3-fluorophenyl | 2-db | 1H-imidazol-2-yl | 252 |
| 23 | B1a-1 | db | 3-fluorophenyl | 2-db | 1-methyl-1H-pyrazol-5-yl | 230 |

TABLE 1-continued
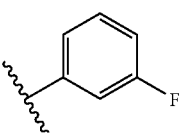
| Co. no. | Ex. no. | $X_1$ | $R^2$ | $X_2$ | $R^3$ | physical data (m.p. °C.)/salt |
|---|---|---|---|---|---|---|
| 24 | B2a | db | 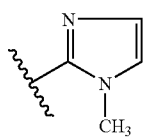 | 2-db | 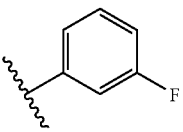 | 218 |
| 25 | B1a-2 | db | 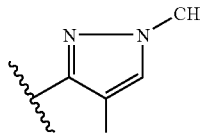 | 2-db | 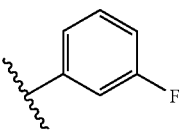 | 218 |
| 26 | B1b-1 | db | 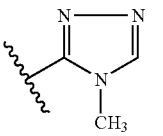 | 2-db | 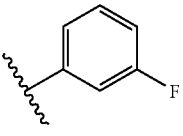 | |
| 27 | B1b-2 | db | 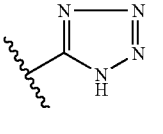 | 2-db | 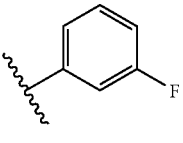 | >260 |
| 28 | B1b-1 | db | 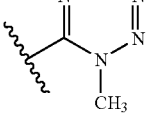 | 2-db | 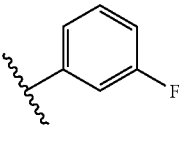 | 256 |
| 29 | B1b-1 | db | 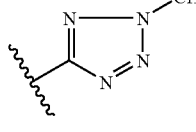 | 2-db | 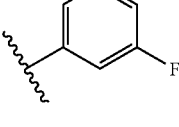 | >280 |
| 1 | B1a-1 | db | 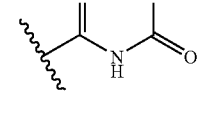 | 2-db | 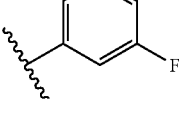 | |
| 30 | B1a-4 | db | 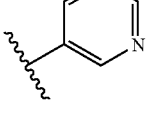 | 2-db | 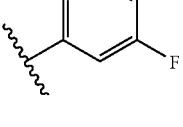 | 208 |
| 31 | B1a-2 | db | 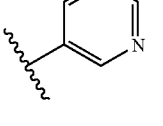 | 2-db | | >260 |

TABLE 1-continued
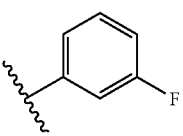
| Co. no. | Ex. no. | X₁ | R² | X₂ | R³ | physical data (m.p. ° C.)/salt |
|---|---|---|---|---|---|---|
| 2 | B1b-1 | db | 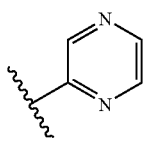 | 2-db | 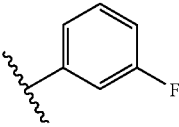 | >260 |
| 32 | B1a-1 | db | 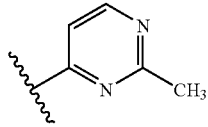 | 2-db | 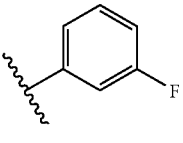 | |
| 33 | B1a-1/ B4c | db | 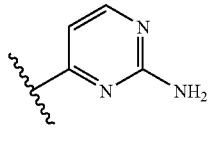 | 2-db | 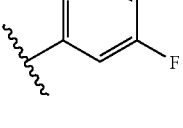 | 264 |
| 34 | B4b | db | 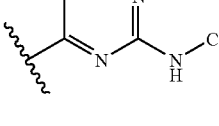 | 2-db | 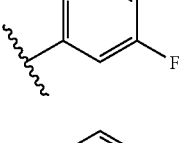 | |
| 35 | B4a | db | 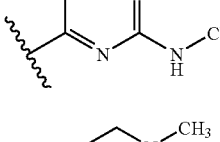 | 2-db | 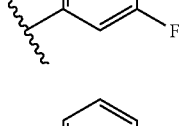 | >250 |
| 36 | B1b-3 | db | 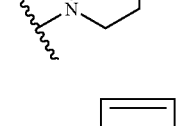 | 2-db | 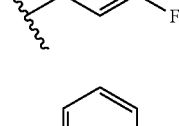 | >250 HCl |
| 37 | B1a-2 | db | 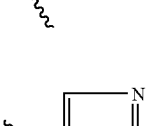 | 3-db | 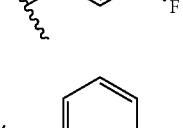 | 218 |
| 38 | B1a-1 | db | 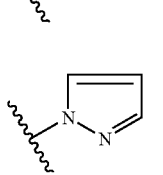 | 3-db |  | >260 |
| 39 | B1a-2 | db |  | 3-db | | 242 |

TABLE 1-continued
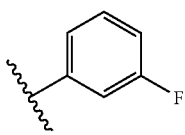
| Co. no. | Ex. no. | X₁ | R² | X₂ | R³ | physical data (m.p. °C.)/salt |
|---|---|---|---|---|---|---|
| 40 | B1a-1 | db | 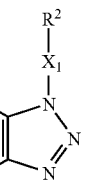 | 3-db | 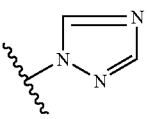 | >260 |
| 41 | B1a-2 | db | 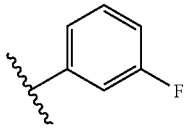 | 3-db | 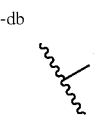 | 200 |
| 138 | B1b-1 | db | 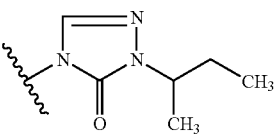 | 3-db | 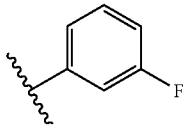 | >280 |
| 42 | B1a-1 | db |  | 3-db | 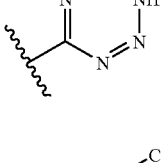 | >260 |
| 43 | B1a-2 | db | 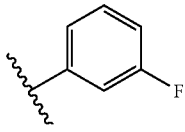 | 2-db |  | >260 HCl |
| 44 | B1a-2 | db | 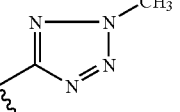 | 2-db | 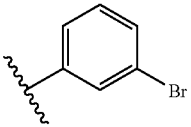 | 242 |
| 8 | B1a-2 | db |  | 2-db | 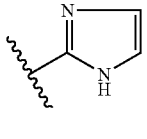 | 242 |
| 45 | B1a-2 | db | 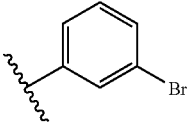 | 2-db |  | 204 |
| 46 | B1a-2 | db | 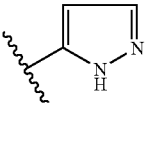 | 2-db | 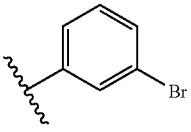 | >270 |

TABLE 1-continued

| Co. no. | Ex. no. | X₁ | R² | X₂ | R³ | physical data (m.p. °C.)/salt |
|---|---|---|---|---|---|---|
| 47 | B1a-2 | db | 3-Br-phenyl | 2-db | pyrimidin-5-yl | >260 |
| 48 | B1a-1 | db | 3-Br-phenyl | 2-db | 2-methylpyrimidin-4-yl | |
| 49 | B1a-1 | db | 4-Br-phenyl | 2-db | 1-methylimidazol-2-yl | |
| 50 | B1a-2 | db | 3-Br-phenyl | 3-db | 1H-pyrazol-3-yl | 260 |
| 51 | B1a-3 | db | 3-Br-phenyl | 3-db | 1,2,4-triazol-1-yl | |
| 52 | B1a-2 | db | 3-Br-phenyl | 3-db | 1H-tetrazol-5-yl | |
| 53 | B1a-2 | db | 3-Br-phenyl | 3-db | 2-methyltetrazol-5-yl | 246 |
| 55 | B2a | db | 4-SCH₃-phenyl | 2-db | 1-methylimidazol-2-yl | |
| 7 | B3 | db | 3-CONH₂-phenyl | 2-db | 1-methylimidazol-2-yl | |

TABLE 1-continued

| Co. no. | Ex. no. | X₁ | R² | X₂ | R³ | physical data (m.p. °C.)/salt |
|---------|---------|-----|-----|-----|-----|------------------------------|
| 57 | B2a | db | 4-(N-methyl-N-acetylamino)phenyl | 2-db | 1-methyl-imidazol-2-yl | |
| 58 | B2a | db | 4-(phenylthio)phenyl | 2-db | 1-methyl-imidazol-2-yl | |
| 145 | B1b-4 | db | 3-(sulfamoyl)phenyl | 2-db | oxazol-5-yl | 183 |
| 146 | B1b-4 | db | 3-(sulfamoyl)phenyl | 2-db | 1-methyl-tetrazol-5-yl | >260 |
| 147 | B1b-4 | db | 3-(sulfamoyl)phenyl | 2-db | 2-aminopyrimidin-4-yl | >260 |
| 59 | B2b-1 | db | 3-(1-methyl-imidazol-2-yl)phenyl | 2-db | 1-methyl-imidazol-2-yl | |
| 60 | B2a | db | 3-chloro-4-methylphenyl | 2-db | 1-methyl-imidazol-2-yl | |
| 61 | B2a | db | 3-fluoro-4-methoxyphenyl | 2-db | 1-methyl-imidazol-2-yl | |

TABLE 1-continued

Core structure:

R³–X₂–[phenyl(positions 1,2,3)]–NH–[triazolopyrimidine with X₁–R² substituent]

| Co. no. | Ex. no. | X₁ | R² | X₂ | R³ | physical data (m.p. °C.)/salt |
|---|---|---|---|---|---|---|
| 62 | B2a | db | 4-fluoro-3-(trifluoromethyl)phenyl | 2-db | 1-methyl-1H-imidazol-2-yl | |
| 63 | B2a | db | 3-methoxy-5-(trifluoromethyl)phenyl | 2-db | 1-methyl-1H-imidazol-2-yl | |
| 64 | B2a | db | 4-benzoyl-3-methoxyphenyl | 2-db | 1-methyl-1H-imidazol-2-yl | |
| 154 | B1b-8 | db | 3-[(adamantane-1-carbonyl)aminomethyl]phenyl | 2-db | 2-aminopyrimidin-4-yl | |
| 65 | B2b-1 | db | 2,3-dihydro-1H-inden-5-yl | 2-db | 1-methyl-1H-imidazol-2-yl | |
| 148 | B2c | db | 1H-indazol-6-yl | 2-db | 1-methyl-1H-imidazol-2-yl | |
| 66 | B2a | db | 2,3-dihydro-1,4-benzodioxin-6-yl | 2-db | 1-methyl-1H-imidazol-2-yl | |

TABLE 1-continued

| Co. no. | Ex. no. | X₁ | R² | X₂ | R³ | physical data (m.p. ° C.)/salt |
|---|---|---|---|---|---|---|
| 67 | B2a | db | cyclohexyl | 2-db | 1-methyl-imidazol-2-yl | |
| 6 | B2c | db | cyclohexyl | 3-db | morpholin-4-yl | |
| 4 | B2b-1 | db | cyclohexyl | 3-db | 4-methylpiperazin-1-yl | 167 |
| 68 | B2a | db | 1-(ethoxycarbonyl)piperidin-4-yl | 2-db | 1-methyl-imidazol-2-yl | | db = direct bond
m.p. = melting point

TABLE 2

| Co. no. | Ex. no. | R¹ | X₂ | R³ | physical data (m.p. ° C.) |
|---|---|---|---|---|---|
| 69 | B4d | —CH₂—CH₃ | db | 2-methylpyrimidin-4-yl | 83 |
| 70 | B4c | —CH₂—CH₃ | db | 2-aminopyrimidin-4-yl | |

TABLE 2-continued

| Co. no. | Ex. no. | R¹ | X₂ | R³ | physical data (m.p. °C.) |
|---|---|---|---|---|---|
| 71 | B4b | —CH₂—CH₃ | db | (4-pyrimidinyl)-2-NHCH₃ | 196 |
| 72 | B4a | —CH₂—CH₃ | db | (4-pyrimidinyl)-2-NHCN | 196 | db = direct bond
m.p. = melting point

TABLE 3

| Co. no. | Ex. no. | X₁ | R² | X₂ | R³ | R⁴ | physical data (m.p. °C.) |
|---|---|---|---|---|---|---|---|
| 5 | B2c | db | cyclohexyl | 3-db | morpholinyl | 2-NO₂ | 162 |
| 150 | B1b-1 | db | 3-fluorophenyl | 3-db | morpholinyl | 2-COOH | >280 | db = direct bond
m.p. = melting point

TABLE 4
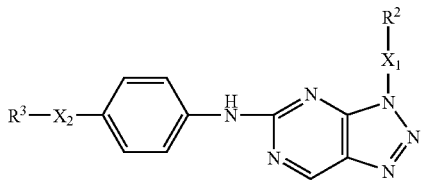
| Co. no. | Ex. no. | $X_1$ | $R^2$ | $-X_2-R^3$ | physical data (m.p. ° C.)/salt |
|---|---|---|---|---|---|
| 78 | B1a-5 | db | 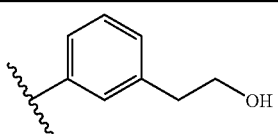 | 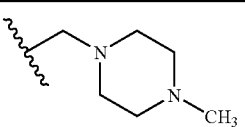 | |
| 79 | B1a-5 | db | 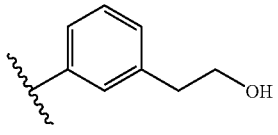 | 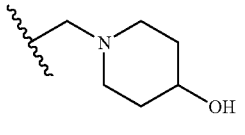 | |
| 80 | B1a-5 | db | 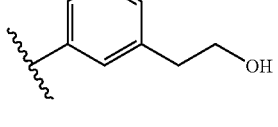 | 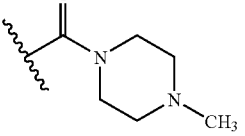 | |
| 81 | B1a-5 | db | 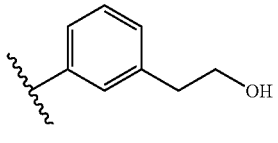 | 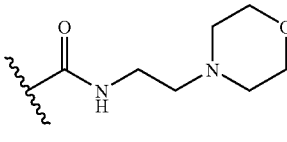 | |
| 82 | B1a-5 | db | 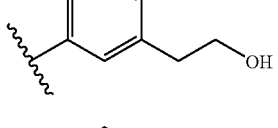 | 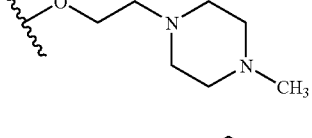 | 160 |
| 83 | B1a-5 | db | 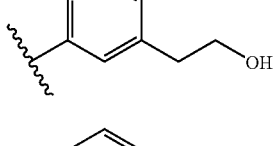 | 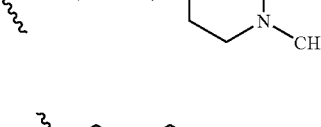 | |
| 89 | B1a-5 | db | 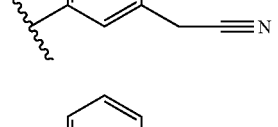 | 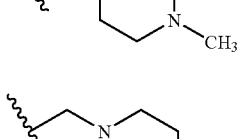 | |
| 90 | B1a-5 | db | 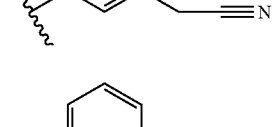 | 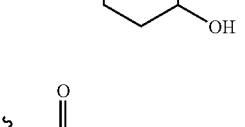 | |
| 91 | B1a-5 | db | 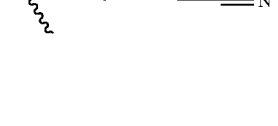 | 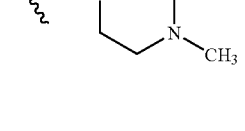 | |

TABLE 4-continued

| Co. no. | Ex. no. | X₁ | R² | —X₂—R³ | physical data (m.p. °C.)/salt |
|---|---|---|---|---|---|
| 92 | B1a-5 | db | 3-cyanomethylphenyl | —NHC(O)CH₂CH₂-morpholine | |
| 93 | B1a-5 | db | 3-cyanomethylphenyl | —OCH₂CH₂-(4-methylpiperazin-1-yl) | 102 |
| 94 | B1a-5 | db | 3-cyanomethylphenyl | —OCH₂CH₂CH₂-(4-methylpiperazin-1-yl) | 115 |
| 101 | B1a-5 | db | 3-(methoxymethyl)phenyl | —CH₂-(4-methylpiperazin-1-yl) | |
| 102 | B1a-5 | db | 3-(methoxymethyl)phenyl | —CH₂-(4-hydroxypiperidin-1-yl) | |
| 103 | B1a-5 | db | 3-(methoxymethyl)phenyl | —C(O)-(4-methylpiperazin-1-yl) | |
| 104 | B1a-5 | db | 3-(methoxymethyl)phenyl | —C(O)NHCH₂CH₂-morpholine | |
| 105 | B1a-5 | db | 3-(methoxymethyl)phenyl | —OCH₂CH₂-(4-methylpiperazin-1-yl) | |
| 106 | B1a-5 | db | 3-(methoxymethyl)phenyl | —OCH₂CH₂CH₂-(4-methylpiperazin-1-yl) | |

TABLE 4-continued

| Co. no. | Ex. no. | X₁ | R² | —X₂—R³ | physical data (m.p. °C.)/salt |
|---|---|---|---|---|---|
| 109 | B1a-5 | db | 3-(CH₂OCH₂CH₂OCH₃)-phenyl | CH₂-(4-methylpiperazin-1-yl) | |
| 110 | B1a-5 | db | 3-(CH₂OCH₂CH₂OCH₃)-phenyl | CH₂-(4-hydroxypiperidin-1-yl) | |
| 111 | B1a-5 | db | 3-(CH₂OCH₂CH₂OCH₃)-phenyl | C(=O)-(4-methylpiperazin-1-yl) | |
| 112 | B1a-5 | db | 3-(CH₂OCH₂CH₂OCH₃)-phenyl | C(=O)NH-CH₂CH₂-morpholin-4-yl | |
| 113 | B1a-5 | db | 3-(CH₂OCH₂CH₂OCH₃)-phenyl | O-CH₂CH₂CH₂-(4-methylpiperazin-1-yl) | |
| 131 | B1a-5 | db | 3-(OCH₂CH₂OCH₃)-phenyl | CH₂-(4-methylpiperazin-1-yl) | 114 |
| 132 | B1a-5 | db | 3-(OCH₂CH₂OCH₃)-phenyl | CH₂-(4-hydroxypiperidin-1-yl) | 120 |
| 133 | B1a-5 | db | 3-(OCH₂CH₂OCH₃)-phenyl | C(=O)-(4-methylpiperazin-1-yl) | |
| 134 | B1a-5 | db | 3-(OCH₂CH₂OCH₃)-phenyl | C(=O)NH-CH₂CH₂-morpholin-4-yl | |

TABLE 4-continued
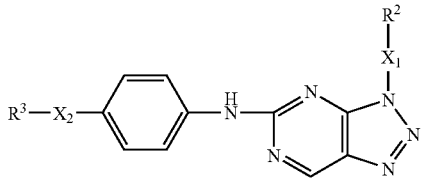
| Co. no. | Ex. no. | X₁ | R² | —X₂—R³ | physical data (m.p. ° C.)/salt |
|---|---|---|---|---|---|
| 153 | B1a-5 | db | 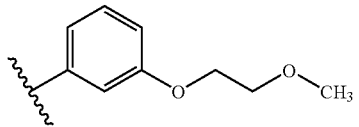 | 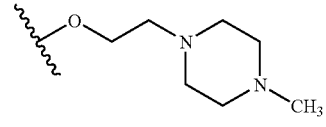 | 110 |
| 135 | B1a-5 | db | 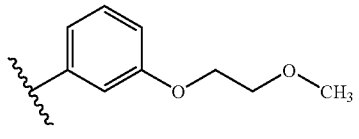 | 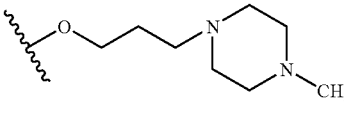 | — |
| 137 | B1a-5 | db | 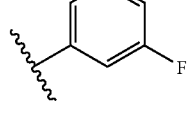 | 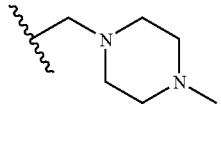 | decomposition at 266° C. HCl |
| 139 | B1b-5 | db | 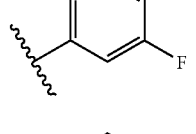 | 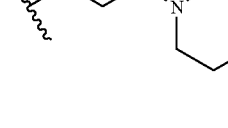 | 140 |
| 140 | B1b-5 | db | 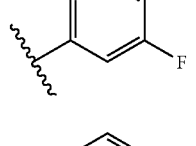 | 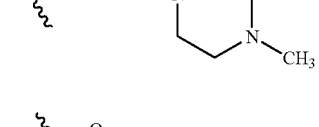 | 129 |
| 141 | B1b-5 | db | 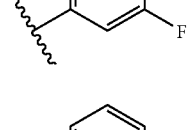 |  | 130 |
| 142 | B1b-5 | db | 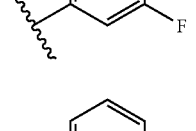 | 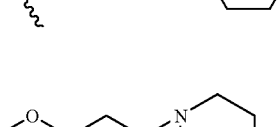 | 139 |
| 143 | B1b-5 | db | 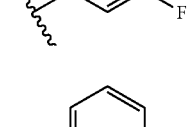 | 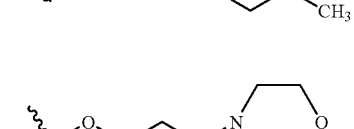 | 140 |
| 144 | B1b-5 | db |  |  | 124 |

TABLE 4-continued

| Co. no. | Ex. no. | X₁ | R² | —X₂—R³ | physical data (m.p. °C.)/salt |
|---|---|---|---|---|---|
| 54 | B1a-1 | db | 3-Br-phenyl | NH-pyrimidin-2-yl | >260 |
| 84 | B1b-2 | db | 3-(2-hydroxyethyl)-phenyl | NH-pyrimidin-2-yl | 246 | db = direct bond
m.p. = melting point

TABLE 5

| Co. no. | Ex. no. | X₁ | R² | —X₂—R³ | physical data (m.p. °C.) |
|---|---|---|---|---|---|
| 136 | B1b-2 | db | 3-F-phenyl | -SO₂-NH-CH₂CH₂-NH-pyrimidin-2-yl | 215 | db = direct bond
m.p. = melting point

C. Analytical Data

The mass of the compounds was recorded with LCMS (liquid chromatography mass spectrometry). Two methods were used which are described below. The data are gathered in Table 6 below.

LCMS Conditions

Method A

The HPLC gradient was supplied by a Waters 600 system with a column heater set at 45° C. Flow from the column was split to a Waters 996 photodiode array (PDA) detector and a Waters-Micromass LCT mass spectrometer with an electrospray ionization source operated in positive ionization mode. Reversed phase HPLC was carried out on a Xterra MS C18 column (3.5 mm, 4.6×100 mm) with a flow rate of 1.6 ml/minute. Three mobile phases (mobile phase A 95% 25mM ammoniumacetate +5% acetonitrile; mobile phase B: acetonitrile; mobile phase C: methanol) were employed to run a gradient condition from 100% A to 35% B and 35% C in 3 minutes, to 50% B and 50% C in 3.5 minutes, to 100% B in 0.5 minute, 100% B for 1 minute and re-equilibrate with 100% A for 1.5 minutes. An injection volume of 10 µL was used. Mass spectra were acquired by scanning from 100 to 1200. The capillary needle voltage was 3 kV and the source temperature was maintained at 120° C. Nitrogen was used a the nebulizer gas. Cone voltage was 10 V for positive ionzation mode. Data acquisition was performed with a Waters-Micromass Mass-Lynx-Openlynx data system.

Method B

The HPLC gradient was supplied by a Waters Alliance HT 2790 system with a columnheater set at 40° C. Flow from the column was split to a Waters 996 photodiode array (PDA) detector and a Waters-Micromass ZQ mass spectrometer with an electrospray ionization source operated in positive and negative ionization mode. Reversed phase HPLC was carried out on a Xterra MS C18 column (3.5 mm, 4.6×100 mm) with a flow rate of 1.6 ml/minute. Three mobile phases (mobile phase A 95% 25 mM ammoniumacetate+5% acetonitrile; mobile phase B: acetonitrile; mobile phase C: methanol) were employed to run a gradient condition from 100% A to 50% B and 50% C in 6.5 minutes, to 100% B in 1 minute, 100% B for 1 minute and reequilibrate with 100% A for 1.5 minutes. An injection volume of 10 μL was used. Mass spectra were acquired by scanning from 100 to 1000 in 1second using a dwell time of 0.1 s. The capillary needle voltage was 3 kV and the source temperature was maintained at 140° C. . Nitrogen was used a the nebulizer gas. Cone voltage. was 10 V for positive ionization mode and 20 V for negative ionization mode. Data acquisition was performed with a Waters-Micromass MassLynx-Openlynx data system.

TABLE 6

LCMS parent peak and retention time values.

| Co. No. | Retention time (minutes) | LCMS [M + H] | Method |
|---|---|---|---|
| 78 | 4.03 | 445 | B |
| 79 | 3.69 | 446 | B |
| 80 | 4.14 | 459 | B |
| 81 | 4.2 | 489 | B |
| 82 | 4.05 | 475 | B |
| 83 | 4.2 | 489 | B |
| 89 | 4.18 | 440 | B |
| 90 | 3.83 | 441 | B |
| 91 | 4.26 | 454 | B |
| 101 | 4.7 | 445 | B |
| 102 | 4.28 | 446 | B |
| 103 | 4.71 | 459 | B |
| 104 | 4.68 | 489 | B |
| 105 | 4.71 | 475 | B |
| 106 | 4.86 | 489 | B |
| 109 | 4.66 | 489 | B |
| 110 | 4.25 | 490 | B |
| 111 | 4.67 | 503 | B |
| 112 | 4.66 | 533 | B |
| 113 | 4.82 | 533 | B |
| 118 | 9.09 | 453 | A |
| 119 | 5.73 | 479 | A |
| 120 | 9.37 | 469 | A |
| 121 | 5.99 | 495 | A |
| 125 | 6.37 | 457 | A |
| 131 | 4.74 | 475 | B |
| 132 | 4.34 | 476 | B |
| 133 | 4.71 | 489 | B |
| 134 | 4.7 | 519 | B |
| 153 | 4.76 | 505 | B |
| 135 | 4.89 | 519 | B |

D. Pharmacological Example

The pharmacological activity of the present compounds was examined using the following test.

GSK3beta assays were performed at room temperature in a 100 μl reaction volume of 25 mM Tris (pH 7.4) containing 10 mM $MgCl_2.6H_2O$, 1 mM DTI, 0.1 mgiml BSA, 5% glycerol and containing 5.7 ng/μl GSK3β, 5 μM biotinylated phosphorylated CREB peptide, 1 μM ATP, 0.85 μCi/ml ATP-$P^{33}$ and a suitable amount of a test compound of formula (I). After one hour, the reaction was terminated by adding 70 μl of Stop mix (0.1 mM ATP, 5 mg/ml streptavidin coated PVT SPA bead pH 11.0). The beads to which the phosphorylated CREB peptide is attached were allowed to settle overnight and the radioactivity of the beads was counted in a microtiterplate scintillation counter and compared with the results obtained in a control experiment (without the presence of a test compound) in order to determine the percentage of GSK3β inhibition. The $IC_{50}$ value, i.e. the concentration (M) of the test compound at which 50% of GSK3β is inhibited, was calculated from the dose response curve obtained by performing the above-described GSK3β assay in the presence of different amounts of the test compound.

The GSK3alpha assay was performed in the same way as described above for the GSK3beta assay except for the concentration of GSK3alpha which is 0.25 ng/μl.

Table 7 lists ranges (namely $pIC_{50}$>8; $pIC_{50}$ ranging between 7 and 8; $pIC_{50}$<7) of $pIC_{50}$ values ($-\log IC_{50}$ (M)) obtained in the above-described test for the present compounds.

TABLE 7

| Compound no. | GSK3b $pIC_{50}$ | GSK3a $pIC_{50}$ |
|---|---|---|
| 17 | >8 | nd |
| 3 | >8 | nd |
| 24 | >8 | >8 |
| 49 | 7-8 | nd |
| 14 | >8 | |
| 55 | 7-8 | nd |
| 56 | 7-8 | nd |
| 57 | <7 | nd |
| 63 | >8 | nd |
| 61 | 7-8 | nd |
| 66 | >8 | nd |
| 148 | 7-8 | nd |
| 65 | >8 | nd |
| 60 | 7-8 | nd |
| 7 | 7-8 | >8 |
| 5 | 7-8 | 7 |
| 33 | >8 | >8 |
| 34 | >8 | >8 |
| 22 | >8 | >8 |
| 11 | 7-8 | 7-8 |
| 35 | >8 | >8 |
| 48 | 7-8 | nd |
| 8 | <7 | >8 |
| 44 | 7-8 | >8 |
| 54 | 7-8 | >8 |
| 47 | >8 | >8 |
| 43 | >8 | >8 |
| 46 | 7-8 | >8 |
| 51 | 7-8 | nd |
| 9 | >8 | >8 |
| 31 | >8 | nd |
| 23 | >8 | >8 |
| 1 | >8 | >8 |
| 32 | >8 | >8 |
| 53 | 7-8 | >8 |
| 25 | 7-8 | 7-8 |
| 42 | >8 | 7-8 |
| 52 | >8 | >8 |
| 45 | 7-8 | 7 |
| 50 | 7-8 | >8 |
| 38 | 7-8 | 7-8 |
| 40 | >8 | >8 |
| 41 | 7-8 | 7-8 |
| 30 | >8 | >8 |
| 37 | <7 | 7 |
| 21 | >8 | >8 |
| 39 | 7-8 | <7 |
| 20 | >8 | >8 |
| 27 | >8 | >8 |
| 2 | >8 | >8 |
| 36 | >8 | >8 |
| 28 | >8 | >8 |
| 29 | >8 | >8 |
| 26 | >8 | >8 |
| 19 | >8 | >8 |
| 127 | 7-8 | >8 |
| 18 | >8 | >8 |
| 16 | >8 | >8 |
| 128 | >8 | >8 |
| 129 | 7-8 | 7-8 |
| 96 | >8 | >8 |
| 149 | >8 | >8 |

TABLE 7-continued

| Compound no. | GSK3b pIC$_{50}$ | GSK3a pIC$_{50}$ |
|---|---|---|
| 74 | >8 | >8 |
| 151 | >8 | >8 |
| 73 | >8 | >8 |
| 146 | 8 | >8 |
| 147 | >8 | >8 |
| 145 | >8 | >8 |
| 97 | >8 | >8 |
| 99 | >8 | >8 |
| 98 | >8 | >8 |
| 136 | 7-8 | 7-8 |
| 100 | >8 | >8 |
| 117 | <9 | >8 |
| 115 | >8 | >8 |
| 116 | >8 | >8 |
| 138 | >8 | >8 |
| 150 | 7 | 7-8 |
| 122 | >8 | >8 |
| 123 | >8 | >8 |
| 76 | >8 | >8 |
| 124 | 7 | 7-8 |
| 114 | >8 | >8 |
| 120 | 7-8 | 7-8 |
| 121 | >8 | 8 |
| 119 | 7 | 7-8 |
| 125 | >8 | >8 |
| 75 | 8 | 7-8 |
| 84 | >8 | >8 |
| 152 | >8 | >8 |
| 87 | >8 | >8 |
| 86 | >8 | >8 |
| 95 | >8 | >8 |
| 107 | >8 | nd |
| 85 | <7 | >8 |
| 77 | >8 | >8 |
| 108 | >8 | 7-8 |
| 88 | >8 | >8 |
| 144 | 7-8 | >8 |
| 142 | 7-8 | 7-8 |
| 141 | 7-8 | >8 |
| 143 | 7-8 | >8 |
| 140 | 7-8 | >8 |
| 130 | 7-8 | 7-8 |
| 131 | 7-8 | 7-8 |
| 133 | 7-8 | >8 |
| 134 | 7-8 | >8 |
| 153 | 7-8 | 7 |
| 135 | 7-8 | 7-8 |
| 109 | 7-8 | 7-8 |
| 110 | 7-8 | 7-8 |
| 111 | >8 | >8 |
| 112 | >8 | >8 |
| 113 | 7-8 | 8 |
| 78 | >8 | >8 |
| 79 | >8 | >8 |
| 80 | >8 | >8 |
| 81 | >8 | >8 |
| 82 | 8 | >8 |
| 83 | >8 | >8 |
| 89 | 7-8 | >8 |
| 90 | >8 | >8 |
| 91 | >8 | >8 |
| 92 | >8 | >8 |
| 93 | 7-8 | 7-8 |
| 94 | >8 | >8 |
| 101 | 7-8 | >8 |
| 102 | 7-8 | 7-8 |
| 103 | >8 | >8 |
| 104 | >8 | >8 |
| 105 | 7-8 | 7-8 |
| 106 | 8 | >8 | nd = not determined

The invention claimed is:

1. A compound of formula

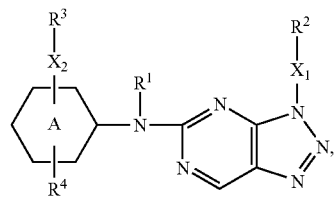

(I)

a pharmaceutically acceptable addition salt, a quaternary amine or a stereochemically isomeric form thereof, wherein ring A is phenyl;

$R^1$ represents hydrogen; aryl; formyl; $C_{1-6}$alkylcarbonyl; $C_{1-6}$alkyl; $C_{1-6}$alkyloxycarbonyl; $C_{1-6}$alkyl substituted with formyl, $C_{1-6}$alkylcarbonyl, $C_{1-6}$alkyloxycarbonyl, $C_{1-6}$alkylcarbonyloxy; or $C_{1-6}$alkyloxy$C_{1-6}$alkylcarbonyl optionally substituted with $C_{1-6}$alkyloxycarbonyl;

$X_1$ represents a direct bond; —(CH$_2$)$_{n3}$— or —(CH$_2$)$_{n4}$—$X_{1a}$—$X_{1b}$—;

with $n_3$ representing an integer with value 1, 2, 3 or 4;

with $n_4$ representing an integer with value 1 or 2;

with $X_{1a}$ representing O, C(=O) or NR$^5$; and with $X_{1b}$ representing a direct bond or $C_{1-2}$alkyl;

$R^2$ represents $C_{3-7}$cycloalkyl; phenyl; a 4, 5, 6- or 7-membered monocyclic heterocycle containing at least one heteroatom selected from O, S or N; benzoxazolyl or a radical of formula

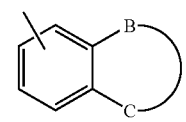

(a-1)

wherein —B—C— represents a bivalent radical of formula

—CH$_2$—CH$_2$—CH$_2$— (b-1);

—CH$_2$—CH$_2$—CH$_2$—CH$_2$— (b-2);

—X$_3$—CH$_2$—CH$_2$—(CH$_2$)$_n$— (b-3);

—X$_3$—CH$_2$—(CH$_2$)$_n$—X$_3$— (b-4);

—X$_3$—(CH$_2$)$_{n'}$—CH=CH— (b-5);

—CH=N—X$_3$— (b-6);

with $X_3$ representing O or NR$^5$;

n representing an integer with value 0, 1, 2 or 3;

n' representing an integer with value 0 or 1;

wherein said R substituent, where possible, may optionally be substituted with at least one substituent selected from halo; hydroxy; $C_{1-6}$alkyl optionally substituted with at least one substituent selected from hydroxy, cyano, carboxyl, $C_{1-4}$alkyloxy, $C_{1-4}$alkyloxy$C_{1-4}$alkyloxy, $C_{1-4}$alkylcarbonyl, $C_{1-4}$alkyloxycarbonyl, $C_{1-4}$alkylcarbonyloxy, NR$^6$R$^7$, —C(=O)—NR$^6$R$^7$, —NR$^5$—C(=O)—NR$^6$R$^7$, —S(=O)$_{n1}$—R$^8$ or —NR$^5$—S(=O)$_{n1}$—R$^8$; $C_{2-6}$alkenyl or $C_{2-6}$alkynyl, each optionally substituted with at least one substituent selected from hydroxy, cyano, carboxyl, $C_{1-4}$alkyloxy, $C_{1-4}$alkylcarbonyl, $C_{1-4}$alkyloxycarbonyl, $C_{1-4}$alkylcarbonyloxy, $NR^6R^7$, —C(=O)—$NR^6R^7$, —$NR^5$—C(=O)—$NR^6R^7$, —S(=O)$_{n1}$—$R^8$ or —$NR^5$—S(=O)$_{n1}$—$R^8$; polyhalo-$C_{1-6}$alkyl optionally substituted with at least one substituent selected from hydroxy, cyano, carboxyl, $C_{1-4}$alkyloxy, $C_{1-4}$alkyloxy$C_{1-4}$alkyloxy, $C_{1-4}$alkylcarbonyl, $C_{1-4}$alkyloxycarbonyl, $C_{1-4}$alkylcarbonyloxy, $NR^6R^7$, —C(=O)—$NR^6R^7$, —$NR^5$—C(=O)-$NR^6R^7$, —S(=O)$^{n1}$—$R^8$ or —$NR^5$—S(=O)$_{n1}$—$R^8$; $C_{1-6}$alkyloxy optionally substituted with at least one substituent selected from hydroxy, cyano, carboxyl, $C_{1-4}$alkyloxy, $C_{1-4}$alkylcarbonyl, $C_{1-4}$alkyloxycarbonyl, $C_{1-4}$alkylcarbonyloxy, $NR^6R^7$, —C(=O)—$NR^6R^7$, —$NR^5$—C(=O)—$NR^6R^7$, —S(=O)$_{n1}$—$R^8$ or —$NR^5$—S(=O)$_{n1}$—$R^8$; polyhalo$C_{1-6}$alkyloxy optionally substituted with at least one substituent selected from hydroxy, cyano, carboxyl, $C_{1-4}$alkyloxy, $C_{1-4}$alkyloxy$C_{1-4}$alkyloxy, $C_{1-4}$alkylcarbonyl, $C_{1-4}$alkyloxycarbonyl, $C_{1-4}$alkylcarbonyloxy, $NR^6R^7$, —C(=O)—$NR^6R^7$, —$NR^5$—C(=O)—$NR^6R^7$, —S(=O)$_{n1}$—$R^8$ or —$NR^5$—S(=O)$_{n1}$—$R^8$; $C_{1-6}$alkylthio; polyhalo$C_{1-6}$alkylthio; $C_{1-6}$alkyloxycarbonyl; $C_{1-6}$alkylcarbonyloxy; $C_{1-6}$alkylcarbonyl; polyhalo$C_{1-6}$alkylcarbonyl; cyano; carboxyl; aryloxy; arylthio; arylcarbonyl; aryl$C_{1-4}$alkyl; aryl$C_{1-4}$alkyloxy; $NR^6R^7$; C(=O)$NR^6R^7$; —$NR^5$—C(=O)—$NR^6R^7$; —$NR^5$—C(=O)—$R^5$; —S(=O)$_{n1}$—$R^8$; —$NR^5$—S(=O)$_{n1}$—$R^8$; —S—CN; —$NR^5$—CN; oxazolyl optionally substituted with $C_{1-4}$alkyl; imidazolyl optionally substituted with $C_{1-4}$alkyl; or

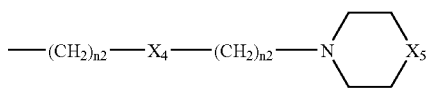

with n2 representing an integer with value 0, 1, 2, 3 or 4;
with $X_4$ representing O, $NR^5$ or a direct bond;
with $X_5$ representing O, $CH_2$, CHOH, CH—N($R_5$)$_2$, $NR^5$ or N—C(=O)—$C_{1-4}$alkyl;
$X_2$ represents a direct bond; —$NR^1$—; —$NR^1$—(CH$_2$)$_{n3}$—; —O—; —O—(CH$_2$)$_{n3}$—; —C(=O)—(CH$_2$)$_{n3}$—; —C(=O)—$NR^5$—(CH$_2$)$_{n3}$—; —C(=S)—; —S—; —S(=O)$_{n1}$—(CH$_2$)$_{n3}$—; —(CH$_2$)$_{n4}$—$X_{1a}$—$X_{1b}$—; —$X_{1a}$—$X_{1b}$—(CH$_2$)$_{n4}$—; —S(=O)$_{n1}$—$NR^5$—(CH$_2$)$_{n3}$—$NR^5$—; or —S(=O)$_{n1}$—$NR^5$—(CH$_2$)$_{n3}$—;
$R^3$ represents a 5- or 6-membered monocyclic heterocycle containing at least one heteroatom selected from O, S or N, or a 9- or 10-membered bicyclic heterocycle containing at least one heteroatom selected from O, S or N, wherein said $R^3$ substituent, where possible, may optionally be substituted with at least one substituent selected from halo; hydroxy; $C_{1-6}$alkyl optionally substituted with at least one substituent selected from hydroxy, cyano, carboxyl, $C_{1-4}$alkyloxy, $C_{1-4}$alkyloxy$C_{1-4}$alkyloxy, $C_{1-4}$alkylcarbonyl, $C_{1-4}$alkyloxycarbonyl, $C_{1-4}$alkylcarbonyloxy, $NR^6R^7$, —C(=O)—$NR^6R^7$, —$NR^5$—C(=O)—$NR^6R^7$, —S(=O)$_{n1}$—$R^8$ or —$NR^5$—S(=O)$_{n1}$—$R^8$; $C_{2-6}$alkenyl or $C_{2-6}$alkynyl, each optionally substituted with at least one substituent selected from hydroxy, cyano, carboxyl, $C_{1-4}$alkyloxy, $C_{1-4}$alkylcarbonyl, $C_{1-4}$alkyloxycarbonyl, $C_{1-4}$alkylcarbonyloxy, $NR^6R^7$, —C(=O)—$NR^6R^7$, —$NR^5$—C(=O)—$NR^6R^7$, —S(=O)$_{n1}$—$R^8$ or —$NR^5$—S(=O)$_{n1}$—$R^8$; polyhalo$C_{1-6}$alkyl; $C_{1-6}$alkyloxy optionally substituted with at least one substituent selected from hydroxy, cyano, carboxyl, $C_{1-4}$alkyloxy, $C_{1-4}$alkylcarbonyl, $C_{1-4}$alkyloxycarbonyl, $C_{1-4}$alkylcarbonyloxy, $NR^6R^7$, —C(=O)—$NR^6R^7$, —$NR^5$—C(=O)—$NR^6R^7$, —S(=O)$_{n1}$—$R^8$ or —$NR^5$—S(=O)$_{n1}$—$R^8$; polyhalo$C_{1-6}$alkyloxy; $C_{1-6}$alkylthio; polyhalo$C_{1-6}$alkylthio; $C_{1-6}$alkyloxycarbonyl; $C_{1-6}$alkylcarbonyloxy; $C_{1-6}$alkylcarbonyl; polyhalo$C_{1-6}$alkylcarbonyl; cyano; carboxyl; $NR^6R^7$; C(=O)$NR^6R^7$; —$NR^5$—C(=O)—$NR^6R^7$; —$NR^5$—C(=O)—$R^5$; —S(=O)$_{n1}$—$R^8$; —$NR^5$—S(=O)$_{n1}$—$R^8$; —S—CN; —$NR^5$—CN; or

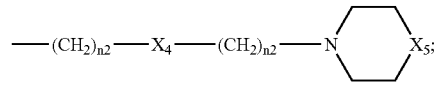

and in case $R^3$ represents a saturated or a partially saturated 5- or 6-membered monocyclic heterocycle containing at least one heteroatom selected from O, S or N, said $R^3$ may also be substituted with at least one oxo;
$R^4$ represents hydrogen; halo; hydroxy; $C_{1-4}$alkyl optionally substituted with at least one substituent selected from hydroxy, cyano, carboxyl, $C_{1-4}$alkyloxy, $C_{1-4}$alkylcarbonyl, $C_{1-4}$alkyloxycarbonyl, $C_{1-4}$alkylcarbonyloxy, $NR^9R^{10}$, —C(=O)—$NR^9R^{10}$, —$NR^5$—C(=O)—$NR^9R^{10}$, —S(=O)$_{n1}$—$R^{11}$ or —$NR^5$—S(=O)$_{n1}$—$R^{11}$; $C_{2-4}$alkenyl or $C_{2-4}$alkynyl, each optionally substituted with at least one substituent selected from hydroxy, cyano, carboxyl, $C_{1-4}$alkyloxy, $C_{1-4}$alkylcarbonyl, $C_{1-4}$alkyloxycarbonyl, $C_{1-4}$alkylcarbonyloxy, $NR^9R^{10}$, —C(=O)—$NR^9R^{10}$, —$NR^5$—C(=O)—$NR^9R^{10}$, —S(=O)$_{n1}$—$R^{11}$ or —$NR^5$—S(=O)$_{n1}$—$R^{11}$; polyhalo$C_{1-3}$alkyl; $C_{1-4}$alkyloxy optionally substituted with carboxyl; polyhalo$C_{1-3}$alkyloxy; $C_{1-4}$alkylthio; polyhalo$C_{1-3}$alkylthio; $C_{1-4}$alkyloxycarbonyl; $C_{1-4}$alkylcarbonyloxy; $C_{1-4}$alkylcarbonyl; polyhalo$C_{1-4}$alkylcarbonyl; nitro; cyano; carboxyl; $NR^9R^{10}$; C(=O)$NR^9R^{10}$; —$NR^5$—C(=O)—$NR^9R^{10}$; —$NR^5$—C(=O)—$R^5$; —S(=O)$_{n1}$—$R^{11}$; —$NR^5$—S(=O)$_{n1}$—$R^{11}$; —S—CN; or —$NR^5$—CN;
$R^5$ represents hydrogen, $C_{1-4}$alkyl or $C_{2-4}$alkenyl;
$R^6$ and $R^7$ each independently represent hydrogen; cyano; $C_{1-6}$alkylcarbonyl optionally substituted with $C_{1-4}$alkyloxy or carboxyl; $C_{1-6}$alkyloxycarbonyl; $C_{3-7}$cycloalkylcarbonyl; adamantanylcarbonyl; $C_{1-4}$alkyloxy$C_{1-4}$alkyl; $C_{1-4}$alkyl substituted with $C_{1-4}$alkyl-$NR^5$—; $C_{1-6}$alkyl optionally substituted with at least one substituent selected from halo, hydroxy, cyano, carboxyl, $C_{1-4}$alkyloxy, polyhalo$C_{1-4}$alkyl, $C_{1-4}$alkyloxy$C_{1-4}$alkyloxy, $NR^{6a}R^{7a}$, C(=O)$NR^{6a}R^{7a}$ or

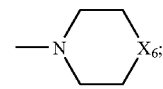

with $X_6$ representing O, $CH_2$, CHOH, CH—N($R_5$)$_2$, $NR^5$ or N—C(=O)—$C_{1-4}$alkyl;
$R^{6a}$ and $R^{7a}$ each independently represent hydrogen; $C_{1-4}$alkyl or $C_{1-4}$alkylcarbonyl;
$R^8$ represents $C_{1-4}$alkyl optionally substituted with hydroxy; polyhalo$C_{1-4}$alkyl or $NR^6R^7$;

$R^9$ and $R^{10}$ each independently represent hydrogen; $C_{1-6}$alkyl; cyano; $C_{1-6}$alkylcarbonyl; $C_{1-4}$alkyloxy$C_{1-4}$alkyl; or $C_{1-4}$alkyl substituted with $C_{1-4}$alkyl-NR$^5$—;

$R^{11}$ represents $C_{1-4}$alkyl or NR$^9$R$^{10}$;

n1 represents an integer with value 1 or 2;

aryl represents phenyl or phenyl substituted with at least one substituent selected from halo, $C_{1-6}$alkyl, $C_{3-7}$cycloalkyl, $C_{1-6}$alkyloxy, cyano, nitro, polyhalo$C_{1-6}$alkyl or polyhalo$C_{1-6}$alkyloxy.

2. A compound according to claim 1 wherein $R^2$ represents $C_{3-7}$cycloalkyl; phenyl or a 4, 5, 6- or 7-membered monocyclic heterocycle containing at least one heteroatom selected from O, S or N; or a radical of formula

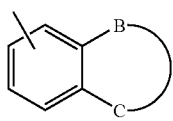

(a-1)

wherein —B—C— represents a bivalent radical of formula

—CH$_2$—CH$_2$—CH$_2$—  (b-1);

—CH$_2$—CH$_2$—CH$_2$—CH$_2$—  (b-2);

—X$_3$—CH$_2$—CH$_2$—(CH$_2$)$_n$—  (b-3);

—X$_3$—CH$_2$—(CH$_2$)$_n$—X$_3$—  (b-4);

—X$_3$—(CH$_2$)$_{n'}$—CH=CH—  (b-5);

with X$_3$ representing O or NR$^5$;

n representing an integer with value 0, 1, 2 or 3;

n' representing an integer with value 0 or 1;

wherein said $R^2$ substituent, where possible, may optionally be substituted with at least one substituent selected from halo; hydroxy; $C_{1-6}$alkyl optionally substituted with at least one substituent selected from hydroxy, cyano, carboxyl, $C_{1-4}$alkyloxy, $C_{1-4}$alkylcarbonyl, $C_{1-4}$alkyloxycarbonyl, $C_{1-4}$alkylcarbonyloxy, NR$^6$R$^7$, —C(=O)—NR$^6$R$^7$, —NR$^5$—C(=O)—NR$^6$R$^7$, —S(=O)$_{n1}$—R$^8$ or —NR$^5$—S(=O)$_{n1}$—R$^8$; $C_{2-6}$alkenyl or $C_{2-6}$alkynyl, each optionally substituted with at least one substituent selected from hydroxy, cyano, carboxyl, $C_{1-4}$alkyloxy, $C_{1-4}$alkylcarbonyl, $C_{1-4}$alkyloxycarbonyl, $C_{1-4}$alkylcarbonyloxy, NR$^6$R$^7$, —C(=O)—NR$^6$R$^7$, —NR$^5$—C(=O)—NR$^6$R$^7$, —S(=O)$_{n1}$—R$^8$ or —NR$^5$—S(=O)$_{n1}$—R$^8$; polyhalo$C_{1-6}$alkyl; $C_{1-6}$alkyloxy optionally substituted with carboxyl; polyhalo$C_{1-6}$alkyloxy; $C_{1-6}$alkylthio; polyhalo$C_{1-6}$alkylthio; $C_{1-6}$alkyloxycarbonyl; $C_{1-6}$alkylcarbonyloxy; $C_{1-6}$alkylcarbonyl; polyhalo$C_{1-6}$alkylcarbonyl; cyano; carboxyl; NR$^6$R$^7$; C(=O)NR$^6$R$^7$; —NR$^5$—C(=O)—NR$^6$R$^7$; —NR$^5$—C(=O)—R$^5$; —S(=O)$_{n1}$—R$^8$; —NR$^5$—S(=O)$_{n1}$—R$^8$; —S—CN; —NR$^5$—CN; or

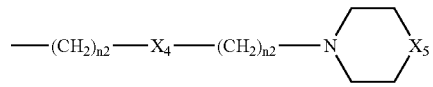

with n2 representing an integer with value 0, 1, 2, 3 or 4;

with X$_4$ representing O, NR$^5$ or a direct bond;

with X$_5$ representing O or NR$^5$;

X$_2$ represents a direct bond; —NR$^1$—; —O—; —C(=O)—; —C(=S)—; —S—; —S(=O)$_{n1}$—; —(CH$_2$)$_{n3}$—; or —(CH$_2$)$_{n4}$—X$_{1a}$—X$_{1b}$—;

$R^3$ represents a 5- or 6-membered monocyclic heterocycle containing at least one heteroatom selected from O, S or N, wherein said $R^3$ substituent, where possible, may optionally be substituted with at least one substituent selected from halo; hydroxy; $C_{1-6}$alkyl optionally substituted with at least one substituent selected from hydroxy, cyano, carboxyl, $C_{1-4}$alkyloxy, $C_{1-4}$alkylcarbonyl, $C_{1-4}$alkyloxycarbonyl, $C_{1-4}$alkylcarbonyloxy, NR$^6$R$^7$, —C(=O)—NR$^6$R$^7$, —NR$^5$—C(=O)—NR$^6$R$^7$, —S(=O)$_{n1}$—R$^8$ or —NR$^5$—S(=O)$_{n1}$—R$^8$; $C_{2-6}$alkenyl or $C_{2-6}$alkynyl, each optionally substituted with at least one substituent selected from hydroxy, cyano, carboxyl, $C_{1-4}$alkyloxy, $C_{1-4}$alkylcarbonyl, $C_{1-4}$alkyloxycarbonyl, $C_{1-4}$alkylcarbonyloxy, NR$^6$R$^7$, —C(=O)—NR$^6$R$^7$, —NR$^5$—C(=O)—NR$^6$R$^7$, —S(=O)$^{n1}$—R$^8$ or —NR$^5$—S(=O)$_{n1}$—R$^8$; polyhalo$C_{1-6}$alkyl; $C_{1-6}$alkyloxy optionally substituted with carboxyl; polyhalo$C_{1-6}$alkyloxy; $C_{1-6}$alkylthio; polyhalo$C_{1-6}$alkylthio; $C_{1-6}$alkyloxycarbonyl; $C_{1-6}$alkylcarbonyloxy; $C_{1-6}$alkylcarbonyl; polyhalo$C_{1-6}$alkylcarbonyl; cyano; carboxyl; NR$^6$R$^7$; C(=O)NR$^6$R$^7$; —NR$^5$—C(=O)—NR$^6$R$^7$; —NR$^5$—C(=O)—R$^5$; —S(=O)$_{n1}$—R$^8$; —NR$^5$—S(=O)$_{n1}$—R$^8$; —S—CN; —NR$^5$—CN; or

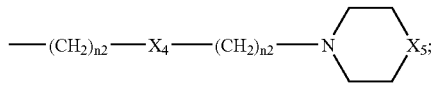

and in case $R^3$ represents a saturated 5- or 6-membered monocyclic heterocycle containing at least one heteroatom selected from O, S or N, said $R^3$ may also be substituted with at least one oxo;

$R^5$ represents hydrogen or $C_{1-4}$alkyl;

$R^6$ and $R^7$ each independently represent hydrogen; cyano; $C_{1-6}$alkylcarbonyl; $C_{1-4}$alkyloxy$C_{1-4}$alkyl; $C_{1-4}$alkyl substituted with $C_{1-4}$alkyl-NR$^5$—; $C_{1-6}$alkyl optionally substituted with hydroxy, $C_{1-4}$alkyloxy, $C_{1-4}$alkyloxy$C_{1-4}$alkyloxy, NR$^{6a}$R$^{7a}$, C(=O)NR$^{6a}$R$^{7a}$ or

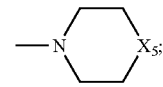

$R^8$ represents $C_{1-4}$alkyl, polyhalo$C_{1-4}$alkyl or NR$^6$R$^7$.

3. A compound as claimed in claim 1 wherein ring A represents phenyl; $R^1$ represents hydrogen or $C_{1-6}$alkyl; $X_1$ represents a direct bond or —(CH$_2$)$_{n3}$—; $R^2$ represents $C_{3-7}$cycloalkyl; phenyl; a 6-membered monocyclic heterocycle containing at least one heteroatom selected from O, S or N; benzoxazolyl; or a radical of formula

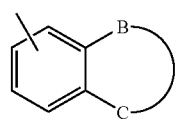

(a-1)

wherein —B—C— represents ambivalent radical of formula

$-CH_2-CH_2-CH_2-$ (b-1);

$-X_3-CH_2-(CH_2)_n-X_3-$ (b-4);

$-CH=N-X_3-$ (b-6);

with $X_3$ representing O or $NR^5$;
n representing an integer with value 1;

wherein said $R^2$ substituent, where possible, may optionally be substituted with at least one substituent, in particular with 1 or 2 substituents selected from halo; $C_{1-6}$alkyl optionally substituted with at least one substituent selected from hydroxy, cyano, $C_{1-4}$alkyloxy, $C_{1-4}$alkyloxy$C_{1-4}$alkyloxy, $NR^6R$ or $-C(=O)-NR^6R^7$; polyhalo$C_{1-6}$alkyl; $C_{1-6}$alkyloxy optionally substituted with $C_{1-4}$alkyloxy; $C_{1-6}$alkylthio; $C_{1-6}$alkyloxycarbonyl; cyano; arylthio; aryloxy; arylcarbonyl; $NR^6R^7$; $C(=O)NR^6R^7$; $-S(=O)_{n1}-R^8$; or imidazolyl optionally substituted with $C_{1-4}$alkyl;

$X_2$ represents a direct bond; $-NR^1-$; $-O-(CH_2)_{n3}-$; $-C(=O)-$; $-C(=O)-NR^5-(CH_2)_{n3}-$; $-(CH_2)_{n3}-$; or $-S(=O)_{n1}-NR^5-(CH_2)_{n3}-NR^5-$; $R^3$ represents a 5- or 6-membered monocyclic heterocycle containing at least one heteroatom selected from O, S or N; wherein said $R^3$ substituent, where possible, may optionally be substituted with at least one substituent selected from halo; hydroxy; $C_{1-6}$alkyl; or $NR^6R^7$; and in case $R^3$ represents a saturated or a partially saturated 5- or 6-membered monocyclic heterocycle containing at least one heteroatom selected from O, S or N, said $R^3$ may also be substituted with at least one oxo; $R^4$ represents hydrogen; nitro or carboxyl; $R^5$ represents hydrogen; $R^6$ and $R^7$ each independently represent hydrogen; cyano; $C_{1-6}$alkylcarbonyl optionally substituted with $C_{1-4}$alkyloxy; $C_{1-6}$alkyloxycarbonyl; $C_{3-7}$cycloalkylcarbonyl; adamantanylcarbonyl; or $C_{1-6}$alkyl; $R^8$ represents $NR^6R^7$; n1 represents an integer with value 2; aryl represents phenyl.

4. A compound as claimed in claim 1 wherein ring A is phenyl; $R^1$ is hydrogen; $X_1$ is a direct bond or $-(CH_2)_{n3}-$; $R^2$ is indanyl; 2,3-dihydro-1,4-benzodioxanyl; phenyl optionally being substituted with 1 or 2 substituents each independently being selected from $C_{1-4}$alkyl which may optionally be substituted with hydroxy, cyano, $C_{1-4}$alkyloxy, $C_{1-4}$alkyloxy$C_{1-4}$alkyloxy, $NR^6R^7$ or $C(=O)NR^6R^7$; $C_{1-6}$alkyloxy; halo; polyhalo$C_{1-6}$alkyl which may optionally be substituted with hydroxy, cyano, $C_{1-4}$alkyloxy, $C_{1-4}$alkyloxy$C_{1-4}$alkyloxy, $NR^6R^7$ or $C(=O)NR^6R^7$; cyano; $NR^6R^7$; $C(=O)NR^6R^7$; $-S(=O)_{n1}-R^8$; $X_2$ is direct bond; $-NR^1-$; $-O-(CH_2)_{n3}-$; $-C(=O)-$; $-C(=O)-NR^5-(CH_2)_{n3}-$; or $-(CH_2)_{n3}-$; $R^3$ is tetrazolyl; piperazinyl; imidazolyl; oxazolyl; pyrimidinyl; thiazolyl; triazolyl; pyridyl; piperidinyl, pyrazinyl; pyrazolyl or morpholinyl; said rings representing $R^3$ may optionally be substituted with one substitutent selected from $C_{1-6}$alkyl; $NR^6R^7$; hydroxy; halo; and in case $R^3$ represents a saturated or a partially saturated ring system, said $R^3$ may also be substituted with at least one oxo; $R^4$ is hydrogen; $R^6$ and $R^7$ each independently represent hydrogen; cyano; $C_{1-6}$alkylcarbonyl optionally substituted with $C_{1-4}$alkyloxy; $C_{1-6}$alkyloxycarbonyl; $C_{3-7}$cycloalkylcarbonyl; or $C_{1-6}$alkyl; $R^8$ represents $NR^6R^7$.

5. A compound as claimed in claim 1 wherein the $R^3$ substituent is linked to ring A in meta position compared to the $NR^1$ linker.

6. A compound as claimed in claim 1 wherein the $R^3$ substituent is linked to ring A in para position compared to the $NR^1$ linker.

7. A compound as claimed in claim 1 wherein the $R^3$ substituent is an optionally substituted saturated 6-membered monocyclic heterocycle containing at least one heteroatom selected from O, S or N.

8. A compound as claimed in claim 1 wherein $X_1$ represents a direct bond.

9. A compound as claimed in claim 1 wherein $R^2$ represents $C_{3-7}$cycloalkyl; phenyl; a 4, 5, 6- or 7-membered monocyclic heterocycle containing at least one heteroatom selected from O, S or N; benzoxazolyl or a radical of formula (a-1) wherein said $R^2$ substituent is substituted with at least one substituent selected from $C_{1-6}$alkyl substituted with $NR^6R^7$; $C_{2-6}$alkenyl or $C_{2-6}$alkynyl, each substituted with $NR^6R^7$; polyhalo $C_{1-6}$alkyl substituted with $NR^6R^7$; $C_{1-6}$alkyloxy substituted with $NR^6R^7$; polyhalo$C_{1-6}$alkyloxy substituted with $NR^6R^7$; or $NR^6R^7$.

10. A compound as claimed in claim 1 wherein $R^3$ represents a 5- or 6-membered monocyclic heterocycle containing at least one heteroatom selected from O, S or N, or a 9- or 10-membered bicyclic heterocycle containing at least one heteroatom selected from O, S or N, wherein said $R^3$ substituent is substituted with at least one substituent selected from $C_{1-6}$alkyl substituted with $NR^6R^7$; $C_{2-6}$alkenyl or $C_{2-6}$alkynyl, each substituted with $NR^6R^7$; $C_{1-6}$alkyloxy substituted with $NR^6R^7$; or $NR^{67}$.

11. A compound as claimed in claim 1 wherein $R^2$ represents $C_{3-7}$cycloalkyl; phenyl; a 4, 5, 6- or 7-membered monocyclic heterocycle containing at least one heteroatom selected from O, S or N; benzoxazolyl or a radical of formula (a-1), wherein said $R^2$ substituent is substituted with at least one substituent selected from halo; polyhalo$C_{1-6}$alkyl optionally substituted with at least one substituent selected from hydroxy, cyano, carboxyl, $C_{1-4}$alkyloxy, $C_{1-4}$alkyloxy-$C_{1-4}$alkyloxy, $C_{1-4}$alkylcarbonyl, $C_{1-4}$alkyloxycarbonyl, $C_{1-4}$alkylcarbonyloxy, $NR^6R^7$, $-C(=O)-NR^6R^7$, $-NR^5-C(=O)-NR^6R^7$, $-S(=O)_{n1}-R^8$ or $-NR^5-S(=O)_{n1}-R^8$; polyhalo-$C_{1-6}$alkyloxy optionally substituted with at least one substituent selected from hydroxy, cyano, carboxyl, $C_{1-4}$alkyloxy, $C_{1-4}$alkyloxy$C_{1-4}$alkyloxy, $C_{1-4}$alkylcarbonyl, $C_{1-4}$alkyloxycarbonyl, $C_{1-4}$alkylcarbonyloxy, $NR^6R^7$, $-C(=O)-NR^6R^7$, $-NR^5-C(=O)-NR^6R^7$, $-S(=O)^{n1}-R^8$ or $-NR^5-S(=O)_{n1}-R^8$.

12. A compound as claimed in claim 1 wherein the compound is selected from

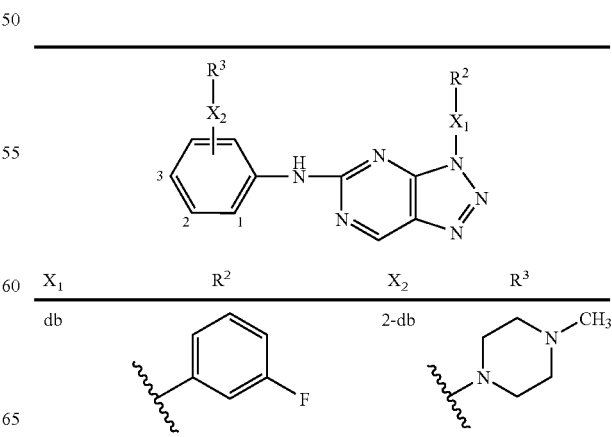

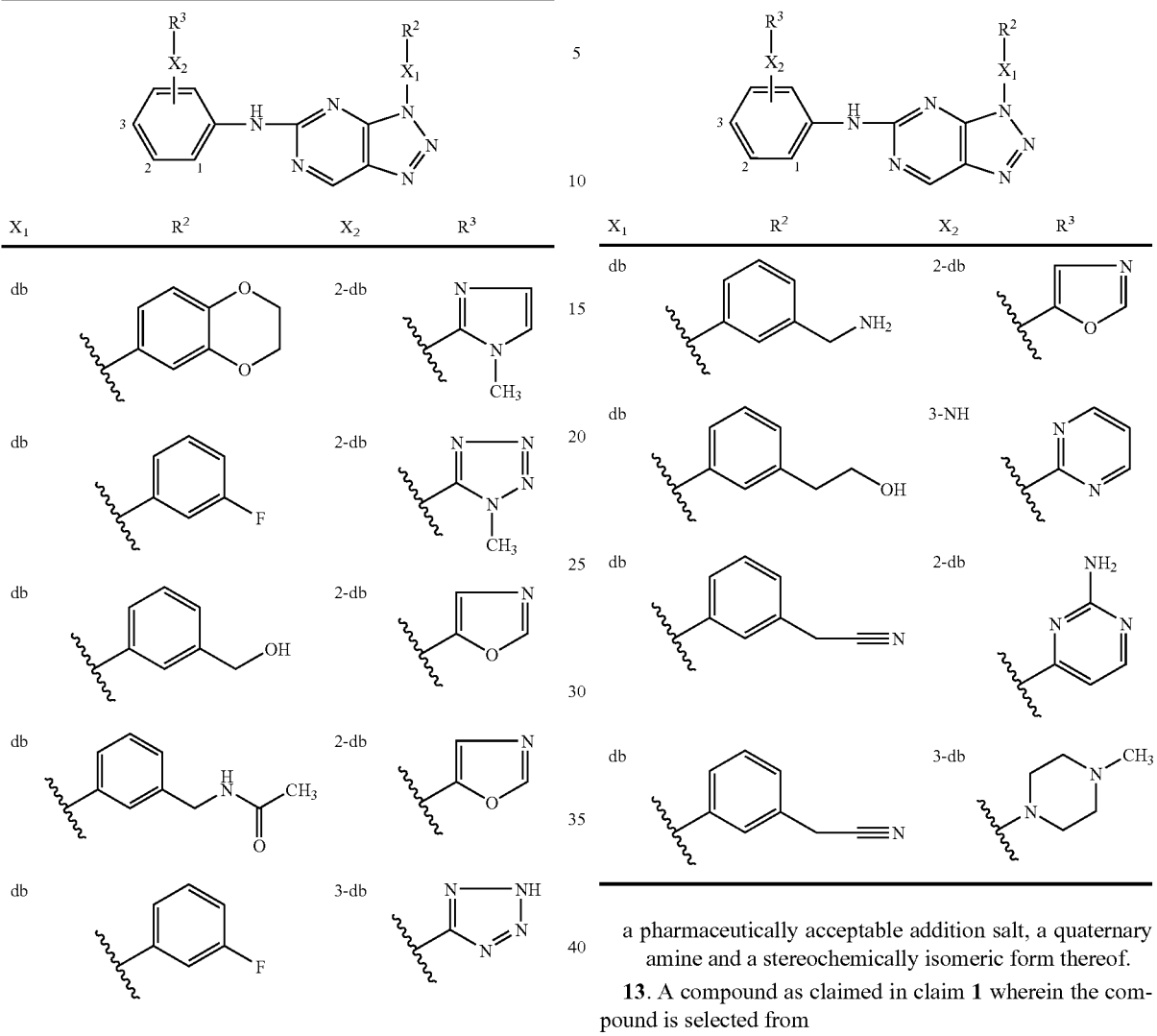
a pharmaceutically acceptable addition salt, a quaternary amine and a stereochemically isomeric form thereof.
13. A compound as claimed in claim 1 wherein the compound is selected from
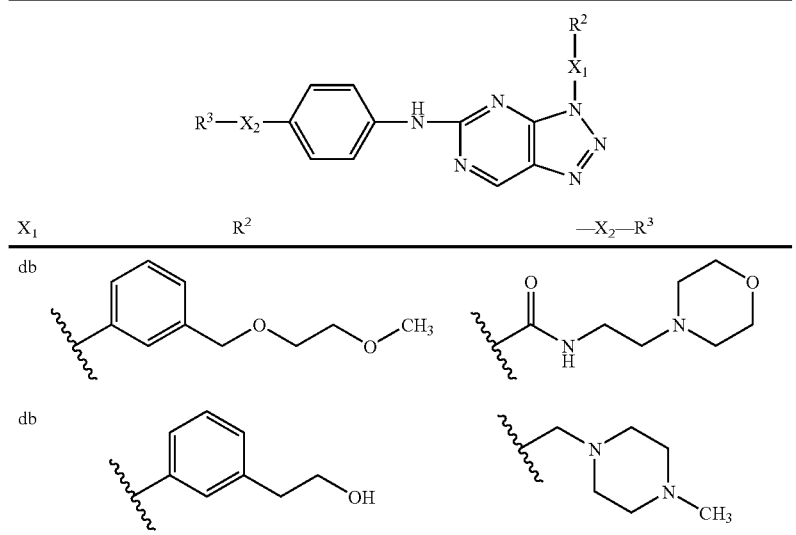

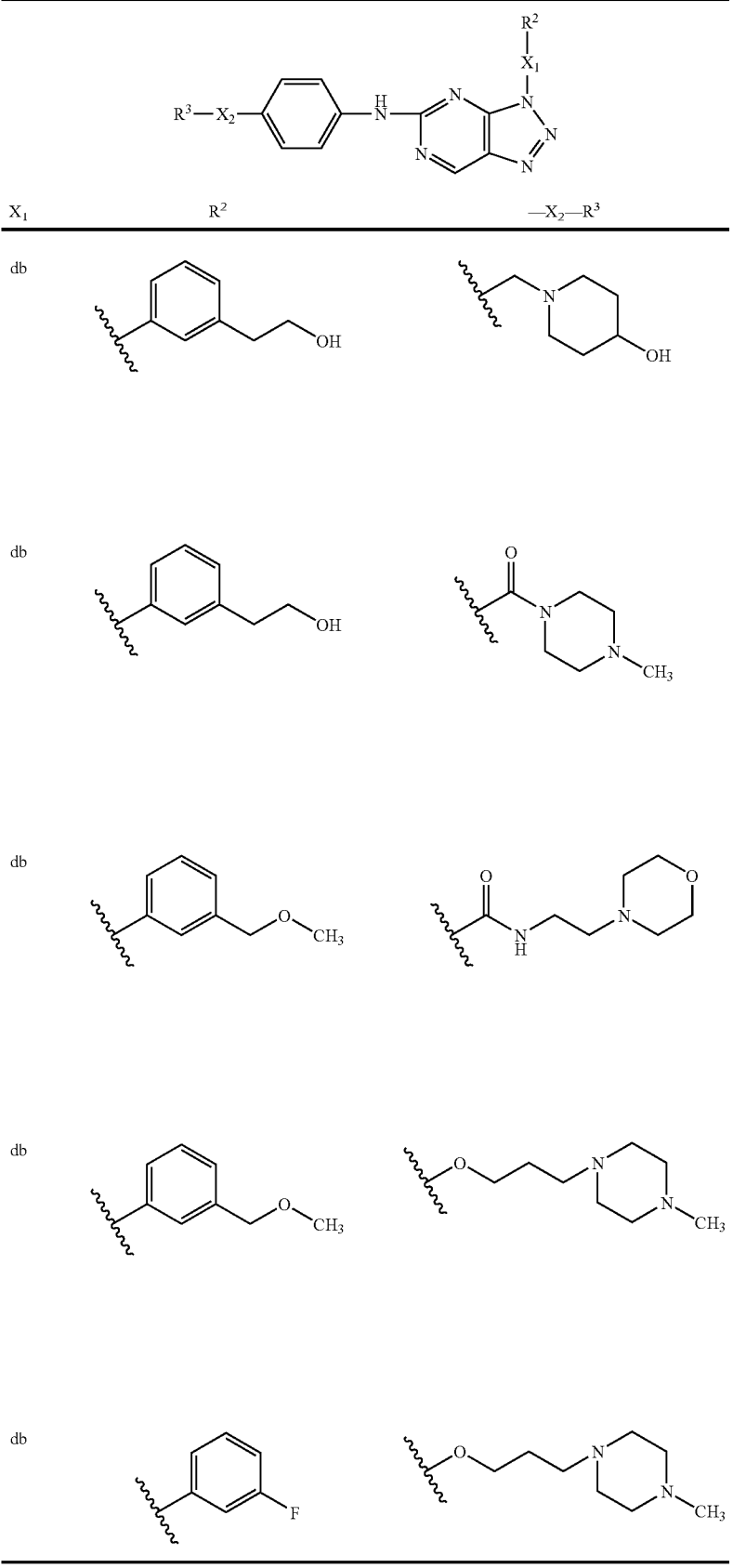

a pharmaceutically acceptable addition salt, a quaternary amine and a stereochemically isomeric form thereof.

14. A pharmaceutical composition comprising a compound as claimed in claim 1 and a pharmaceutical excipient.

15. A pharmaceutical composition comprising a pharmaceutically acceptable carrier and as active ingredient a compound as claimed in claim 1.

16. A process for preparing a pharmaceutical composition comprising mixing a compound as claimed in claim 1 with a pharmaceutically acceptable carrier.

17. A process for preparing a compound as claimed in claim 1, comprising
   a) cyclizing an intermediate of formula (H) in the presence of a nitrite salt, a suitable solvent, and a suitable acid,

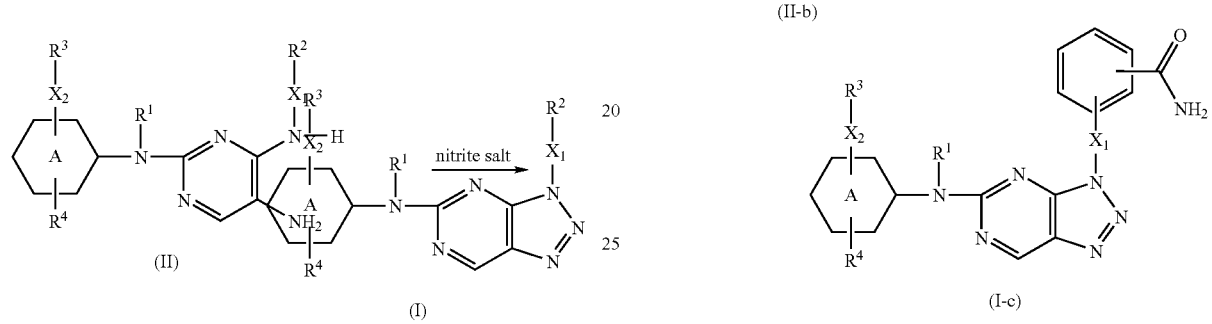

wherein ring A, $R^1$ to $R^4$, $X_1$ and $X_2$ are as defined in claim 1;

b) cyclizing an intermediate of formula (II-a) in the presence of a nitrite salt, a suitable solvent, and a suitable acid,

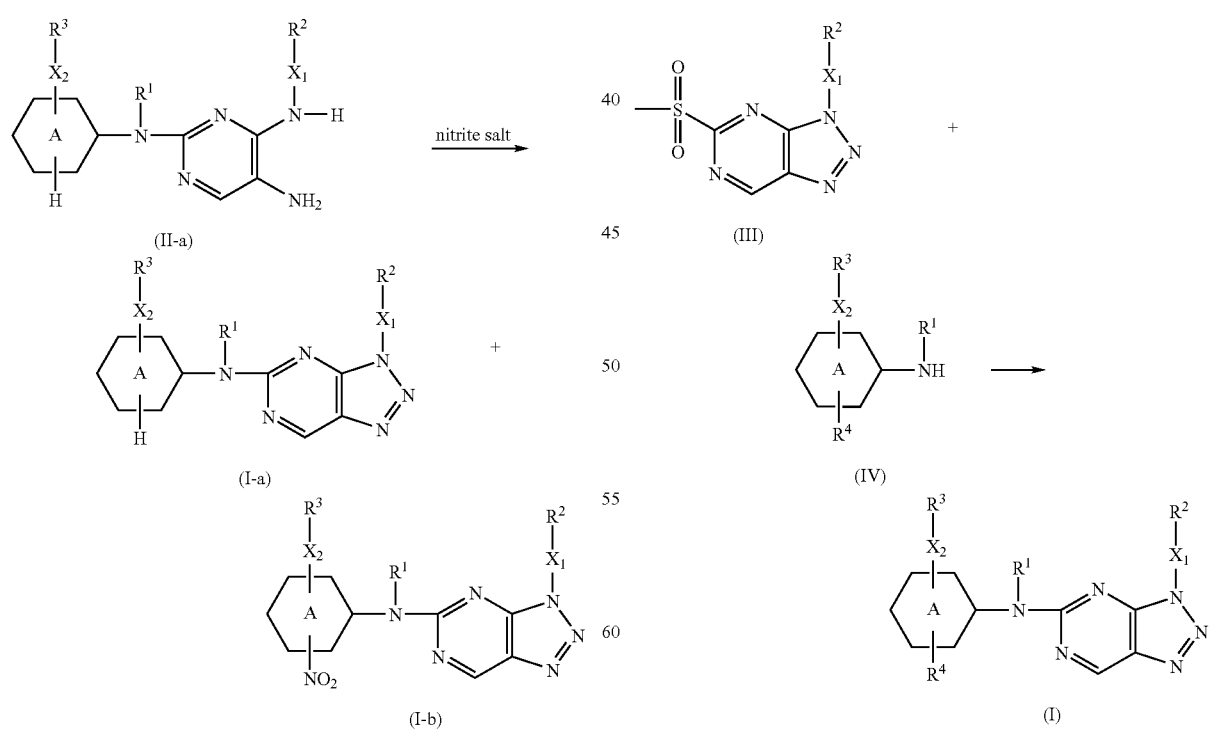

wherein ring A, $R^1$ to $R^3$, $X_1$ and $X_2$ are as defined in claim 1;

c) cyclizing an intermediate of formula (II-b) in the presence of a nitrite salt, a suitable solvent, and a suitable acid,

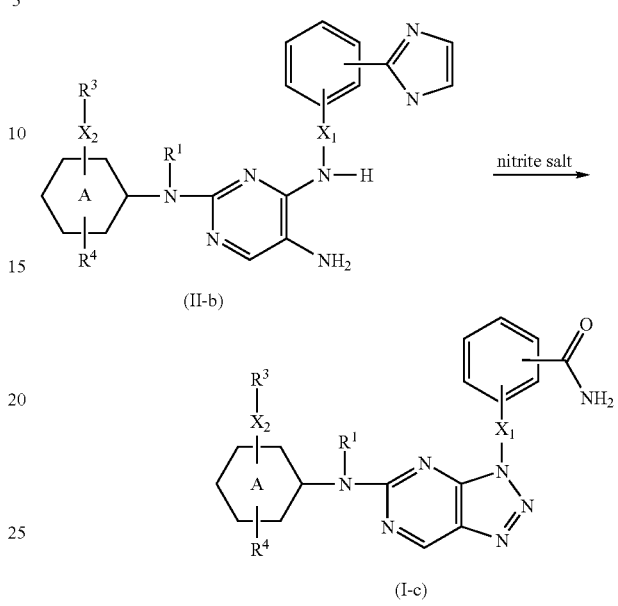

wherein ring A, $R^1$, $R^3$ and $R^4$, $X_1$ and $X_2$ are as defined in claim 1;

d) reacting an intermediate of formula (III) with an intermediate of formula (IV) in the presence of a suitable solvent,

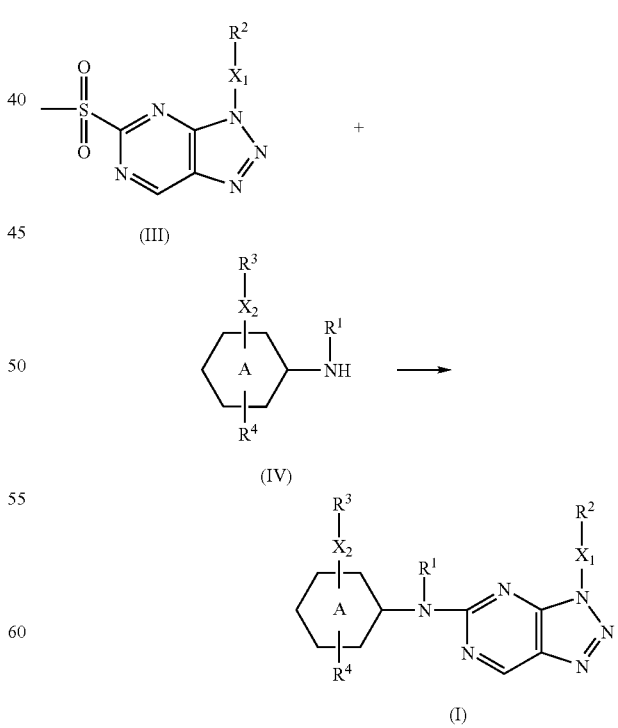

wherein ring A, $R^1$ to $R^4$, $X_1$ and $X_2$ are as defined in claim 1;

e) reacting an intermediate of formula (XV) with an intermediate of formula (XVI), wherein $R^b$ represents hydrogen, $C_{1-4}$alkyl or cyano, and $R^c$ represents hydrogen or $C_{1-4}$alkyl, in the presence of a suitable solvent and a suitable salt

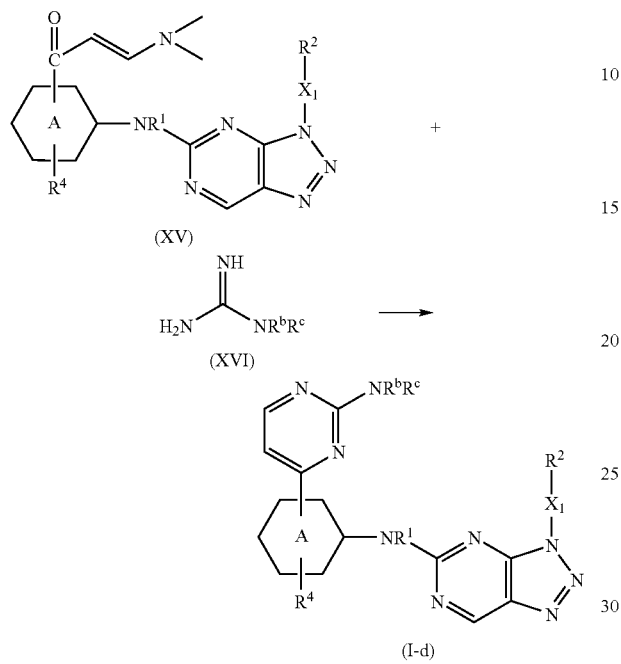

wherein ring A, $R^1$ $R^2$, $R^4$ and $X_1$ are as defined in claim 1;

f) reacting an intermediate of formula (XV) with hydrazine in the presence of a suitable solvent,

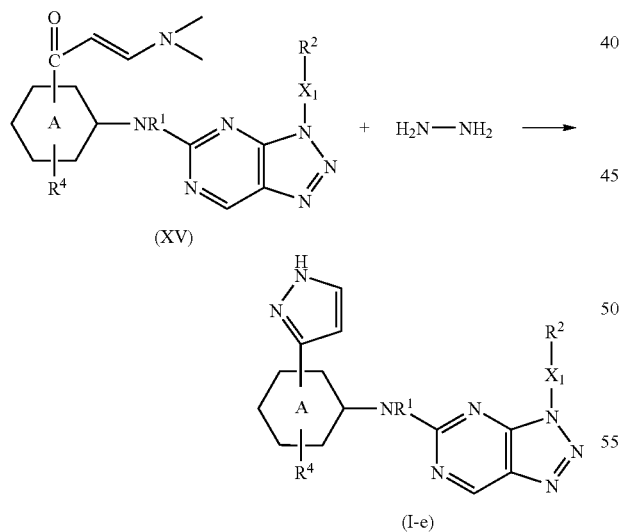

wherein ring A, $R^1$ $R^2$, $R^4$ and $X_1$ are as defined in claim 1;

g) reacting an intermediate of formula (III') with an intermediate of formula (IV) in the presence of a suitable solvent, and optionally in the presence of a suitable base,

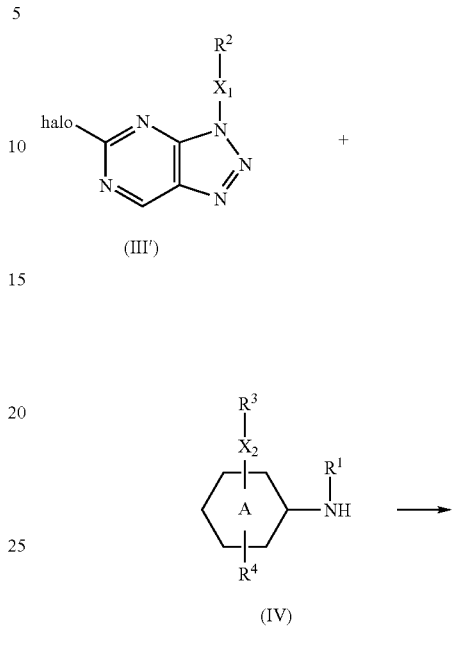

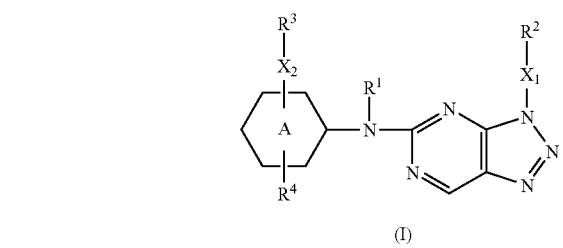

wherein ring A, $R^1$ $R^2$, $R^3$, $R^4$, $X_1$ and $X_2$ are as defined in claim 1;

and optionally converting compounds of formula (I) into each other following art-known transformations, and further, optionally converting the compounds of formula (I), into a therapeutically active non-toxic acid addition salt by treatment with an acid, or into a therapeutically active non-toxic base addition salt by treatment with a base, or conversely, converting the acid addition salt form into the free base by treatment with alkali, or converting the base addition salt into the free acid by treatment with acid; and, optionally preparing stereochemically isomeric forms, quaternary amines or N-oxide forms thereof.

* * * * *

UNITED STATES PATENT AND TRADEMARK OFFICE
CERTIFICATE OF CORRECTION

PATENT NO.      : 7,449,465 B2                                    Page 1 of 3
APPLICATION NO. : 10/565065
DATED           : November 11, 2008
INVENTOR(S)     : Eddy Jean Edgard Freyne et al.

It is certified that error appears in the above-identified patent and that said Letters Patent is hereby corrected as shown below:

Column 5,
Line 29, delete "c-electrons" and insert -- π-electrons --.

Column 8,
Line 52, delete "–NR$^5$–;" and insert -- –NR$^1$–; --.

Column 10,
Line 56, delete "R" and insert -- R$^3$ --.

Column 11,
Line 10, delete "R" and insert -- R$^4$ --.
Line 52, delete "–C(=O)–NR$^6$R$^7$," and insert -- –NR$^5$–C(=O)-NR$^6$R$^7$, --.

Column 13,
Line 21, delete "R" and insert -- R$^2$ --.

Column 19,
Line 26, delete "R" and insert -- R$^2$ --.

Column 20,
Line 10, delete "R" and insert -- R$^2$ --.

Column 25,
Lines 5-15, delete

"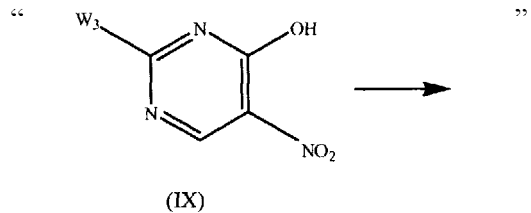"

(IX)

Signed and Sealed this

Tenth Day of August, 2010

David J. Kappos
*Director of the United States Patent and Trademark Office* and insert

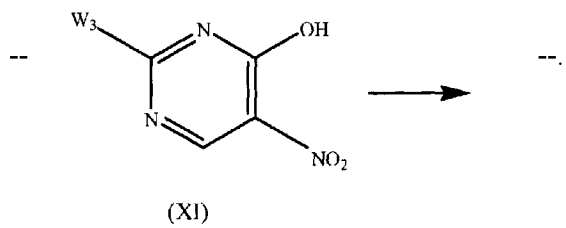

(XI)

Column 30,
Line 22, delete "(XIVI" and insert -- (XIV) --.

Column 112,
Line 57, delete "R" and insert -- $R^2$ --.

Column 116,
Lines 53-54, delete "ring A represents phenyl;".

Column 117,
Line 1, delete "ambivalent" and insert -- a bivalent --.
Line 16, delete "$NR^6R$" and insert -- $NR^6R^7$ --.
Lines 42-43, delete "ring A is phenyl;".

Column 118,
Line 29, delete "$NR^{67}$." and insert -- $NR^6R^7$. --.

Column 123,
Line 14, delete "formula (H)" and insert -- formula II --.
Lines 16-28, delete "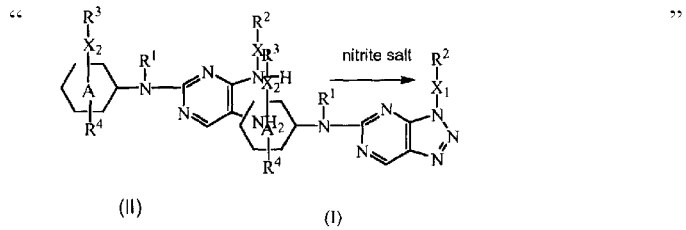"

and insert

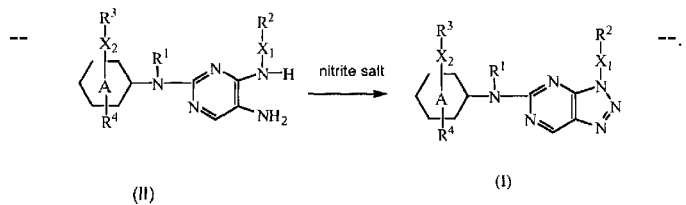

Column 126,
Lines 57-58, delete "forms, quaternary amines or N-oxide forms thereof."
and insert -- forms or quaternary amines thereof. --.